US011111498B2

(12) United States Patent
Jenkins et al.

(10) Patent No.: US 11,111,498 B2
(45) Date of Patent: Sep. 7, 2021

(54) HIGH FRUCTAN CEREAL PLANTS

(71) Applicants: Colin Leslie Dow Jenkins, Evatt (AU); Bryan Charles Clarke, Pearce (AU); Zhongyi Li, Kaleen (AU); Matthew Kennedy Morell, Aranda (AU)

(72) Inventors: Colin Leslie Dow Jenkins, Evatt (AU); Bryan Charles Clarke, Pearce (AU); Zhongyi Li, Kaleen (AU); Matthew Kennedy Morell, Aranda (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 157 days.

(21) Appl. No.: 15/671,970

(22) Filed: Aug. 8, 2017

(65) Prior Publication Data

US 2018/0171349 A1    Jun. 21, 2018

Related U.S. Application Data

(60) Division of application No. 13/008,746, filed on Jan. 18, 2011, now Pat. No. 9,752,157, which is a (Continued)

(30) Foreign Application Priority Data

Feb. 13, 2009  (AU) ............................... 2009200577

(51) Int. Cl.
  *C12N 15/82*   (2006.01)
  *G01N 33/50*   (2006.01)

(52) U.S. Cl.
  CPC ......... *C12N 15/8245* (2013.01); *G01N 33/50* (2013.01); *G01N 2400/38* (2013.01)

(58) Field of Classification Search
  CPC .................................................. C12N 15/8245
  See application file for complete search history.

(56) References Cited

U.S. PATENT DOCUMENTS

| 3,690,896 A | 9/1972 | Maxwell et al. |
| 4,770,710 A | 9/1988 | Friedman et al. |

(Continued)

FOREIGN PATENT DOCUMENTS

| GB | 2 360 521 | 9/2001 |
| WO | WO 1997/022703 | 6/1997 |

(Continued)

OTHER PUBLICATIONS

Henry, J. Sci. Food Agric. 1985, 36, 1243-1253.*

(Continued)

*Primary Examiner* — Amber R Orlando
*Assistant Examiner* — Philip A Dubois
(74) *Attorney, Agent, or Firm* — Gary J. Gershik

(57) ABSTRACT

The invention provides cereal plants having a high level of fructan useful for the production of a range of food, beverage, nutraceutical and pharmaceutical products. The invention provides methods of producing high-fructan products from plants modified to comprise a reduced level of an endogenous polypeptide with starch synthase activity, and products so produced. In some embodiments, plants are modified by introduction of an agent such as a nucleic acid molecule which down regulates endogenous starch synthase II gene expression.

1 Claim, 3 Drawing Sheets

Specification includes a Sequence Listing.

Related U.S. Application Data continuation-in-part of application No. PCT/AU2009/000911, filed on Jul. 16, 2009.

(60) Provisional application No. 61/135,111, filed on Jul. 17, 2008, provisional application No. 61/135,361, filed on Jul. 18, 2008.

(56) References Cited

U.S. PATENT DOCUMENTS

| | | | |
|---|---|---|---|
| 5,051,271 | A | 9/1991 | Iyengar et al. |
| 5,792,920 | A | 8/1998 | Bridges et al. |
| 6,013,861 | A | 1/2000 | Bird et al. |
| 6,083,547 | A | 7/2000 | Katta et al. |
| 6,303,174 | B1 | 10/2001 | McNaught et al. |
| 6,307,125 | B1 | 10/2001 | Block et al. |
| 6,376,749 | B1 | 4/2002 | Broglie et al. |
| 6,483,009 | B1 | 11/2002 | Poulsen et al. |
| 6,664,444 | B1 * | 12/2003 | Koops ............ C12N 9/1051 435/101 |
| 6,730,825 | B1 | 5/2004 | Goldsbrough et al. |
| 6,734,339 | B2 | 5/2004 | Block et al. |
| 6,897,354 | B1 | 5/2005 | Yamamori et al. |
| 6,903,255 | B2 | 6/2005 | Yamamori et al. |
| 6,916,976 | B1 | 7/2005 | Li et al. |
| 7,001,771 | B1 | 2/2006 | Morell et al. |
| 7,009,092 | B1 | 3/2006 | Jane et al. |
| 7,091,484 | B2 | 5/2006 | Baga et al. |
| 7,135,619 | B1 * | 11/2006 | Visser ............ C12N 15/8245 800/284 |
| 7,521,593 | B2 | 4/2009 | Regina et al. |
| 7,667,114 | B2 | 2/2010 | Morell et al. |
| 7,700,139 | B2 | 4/2010 | Bird et al. |
| 7,700,826 | B2 | 9/2010 | Morell et al. |
| 7,790,955 | B2 | 10/2010 | Li et al. |
| 7,812,221 | B2 | 10/2010 | Regina et al. |
| 7,888,499 | B2 | 4/2011 | Morell et al. |
| 7,919,132 | B2 | 8/2011 | Regina et al. |
| 7,993,686 | B2 | 8/2011 | Bird et al. |
| 8,115,087 | B2 | 5/2012 | Regina et al. |
| 8,178,759 | B2 | 5/2012 | Morell et al. |
| 8,188,336 | B2 | 5/2012 | Li et al. |
| 8,501,262 | B2 | 8/2013 | Bird et al. |
| 8,829,315 | B2 | 9/2014 | Regina et al. |
| 2003/0035857 | A1 | 2/2003 | Sroka et al. |
| 2003/0213013 | A1 | 11/2003 | Caimi et al. |
| 2003/0221220 | A1 * | 11/2003 | Broglie ............ C08B 30/00 800/284 |
| 2004/0060083 | A1 | 3/2004 | Regina et al. |
| 2004/0204579 | A1 | 10/2004 | Block et al. |
| 2005/0164178 | A1 | 7/2005 | Morell et al. |
| 2006/0010517 | A1 | 1/2006 | Li et al. |
| 2007/0300319 | A1 | 12/2007 | Li et al. |
| 2011/0045127 | A1 | 2/2011 | Ral et al. |
| 2011/0010807 | A1 | 3/2011 | Morell et al. |
| 2011/0059225 | A1 | 9/2011 | Li et al. |
| 2011/0212916 | A1 | 9/2011 | Bird et al. |
| 2011/0281818 | A1 | 11/2011 | Jenkins et al. |
| 2012/0074247 | A1 | 3/2012 | Regina et al. |
| 2012/0114770 | A1 | 5/2012 | Regina et al. |
| 2012/0266267 | A1 | 10/2012 | Li et al. |
| 2013/0115362 | A1 | 5/2013 | Regina et al. |
| 2013/0156924 | A1 | 6/2013 | Morell et al. |
| 2014/0044826 | A1 | 2/2014 | Regina et al. |
| 2014/0205709 | A1 | 7/2014 | Li et al. |

FOREIGN PATENT DOCUMENTS

| | | |
|---|---|---|
| WO | WO 1999/014314 | 3/1999 |
| WO | WO 99/46395 A1 | 9/1999 |
| WO | WO 1999/066050 | 12/1999 |
| WO | WO 2000/015810 | 4/2000 |
| WO | WO 2000/066745 | 9/2000 |
| WO | WO 2001/032886 | 5/2001 |
| WO | WO 2001/062934 | 8/2001 |
| WO | WO 2002/037955 | 5/2002 |
| WO | WO 2002/101059 | 12/2002 |
| WO | WO 2003/023024 | 3/2003 |
| WO | WO 2003/094600 | 11/2003 |
| WO | WO 2005/001098 | 1/2005 |
| WO | WO 2005/040381 | 5/2005 |
| WO | WO 2006/069422 | 7/2006 |
| WO | WO 2010/006373 | 1/2010 |
| WO | WO 2011/011833 | 2/2011 |
| WO | WO 2012/058730 | 5/2012 |
| WO | WO 2012/103594 | 8/2012 |

OTHER PUBLICATIONS

Karppinen et al. (2003). Fructan content of rye and rye products. Cereal Chem., 80(2), 168-171.
Gebbing (2003). The enclosed and exposed part of the peduncle of wheat (Triticum aestivum)—spatial separation of fructan storage. New Phytologist, 159, 245-252.
Smart et al. (1994). The influence of elevated CO2 on non-structural carbohydrate distribution and fructan accumulation in wheat canopies. Plant, Cell and Environment, 17, 435-442.
Huynh et al. (2008). Genotypic variation in wheat grain fructan content revealed by a simplified HPLC method. Journal of Cereal Science, 48, 369-378.
Heyer et al. (1999). Production of modified polymeric carbohydrates. Current Opinion in Biotechnology, 10, 169-174.
Cairns (Jan. 2003). Fructan biosynthesis in transgenic plants. Journal of Experimental Botany, 54(382), 549-567.
International Search Report, dated Sep. 2, 2009 in connection with PCT International Application No. PCT/AU2009/000911, filed Jul. 16, 2009.
Written Opinion of the International Searching Authority, dated Sep. 2, 2009 in connection with PCT International Application No. PCT/AU2009/000911, filed Jul. 16, 2009.
Notification Concerning Transmittal of International Preliminary Report on Patentability (Chapter I of the Patent Cooperation Treaty), including International Preliminary Report on Patentability and Written Opinion of the International Searching Authority, dated Jan. 27, 2011 in connection with PCT International Application No. PCT/AU2009/000911, filed Jul. 16, 2009.
Sep. 28, 2012 First Official Communication from the Examining Division, issued in connection with European Patent Application No. 09797271.5.
Supplementary European Search Report, completed Oct. 5, 2011, and European Search Opinion in connection with European patent Application No. 09797271.5.
Bird et al., "A novel high-amylose barley cultivar (Hordeum vulgare var. Himalaya 292) lowers plasma cholesterol and alters indices of large-bowel fermentation in pigs" British Journal of Nutrition 92, 607-615, 2004.
Clarke et al., "Gene expression in a starch synthase IIa mutant of barley: changes in the level of gene transcription and grain composition" Funct Integr Genomics 8:211-221, 2008.
Livingston et al., "Fructan Precipitation from a Water/Ethanol Extract of Oats and Barley" Plant Physiol. 92. 767-769, 1990.
Morell et al., "Barley sex6 mutants lack starch synthase IIa activity and contain a starch with novel properties" The Plant Journal 34, 173-185, 2003.
Ritsema and Smeekens "Fructans: beneficial for plants and humans" Current Opinion in Plant Biology 6:223-230, 2003.
Tsai et al., "A Study on the Analytical Methods for Total Dietary Fiber in Fructan-Containing Foods" Journal of Food and Drug Analysis, vol. 15, No. 3, 325-331, 2007.
Tungland and Meyer "Nondigestible Oligo—and Polysaccharides (Dietary Fiber): Their Physiology and Role in Human Health and Food" Comprehensive Reviews in Food Science and Food Safety, 3, 90-109, 2002.
Dec. 21, 2012 First Examination Report, issued in connection with Australian Patent Application No. 2009200577.
Adams et al., "Simultaneous determination by capillary gas chromatography of organic acids, sugars, and sugar alcohols in plant tissue extracts as their trimethylsilyl derivatives" Anal. Biochem., 266: 77-84, 1999.

(56) References Cited

OTHER PUBLICATIONS

Almeida and Allshire, "RNA silencing and genome regulation" Trends Cell Biol. 15:251-258, 2005.

Altschul et al., "Gapped BLAST and PSI-BLAST: a new generation of protein database search programs" Nucleic Acids Res. 25:3389, 1997.

Appels and Dvorak, "The wheat ribosomal DNA spacer region: its structure and variation in populations and among species" Theoretical and Applied Genetics, 63: 337-348, 1982.

Batey et al., "Contribution of the Chemical Structure of Wheat Starch to Japanese Noodle Quality" J. Sci. Food Agric. 74: 503-508, 1997.

Bechtold et al., "In planta Agrobacterium mediated gene transfer by infiltration of adult *Arabidopsis thaliana* plants" C.R. Acad. Sci. Paris, 316: 1194-99, 1993.

Bernfeld, In: Colowick S, Kaplan N (eds), "Amylases, α and β" Methods in enzymology. Academic, NY, p. 149-158, 1955.

Bevan et al., "Structure and transcription of the nopaline synthase gene region of T-DNA" Nucl. Acid Res., 11: 369, 1983.

Birch, "Plant Transformation: Problems and Strategies for Practical Application".Ann Rev Plant Physiol Plant Mol. Biol. 48: 297-326, 1997.

Bourque, "Antisense strategies for genetic manipulations in plants" Plant Sci. 105: 125-149, 1995.

Boyer and Preiss, "Multiple forms of (1 → 4)-α-d-glucan, (1 → 4)-α-d- glucan-6-glycosyl transferase from developing *Zea mays* L. Kernels" Carbohydrate Research, 61: 321-334, 1978.

Buleon et al., "Starch granules: structure and biosynthesis" International Journal of Biological Macromulecules, 23: 85-112, 1998.

Campbell et al., "Cost-effective colorimetric microtiter plate enzymatic assays for sucrose, glucose and fructose in sugarcane tissue extracts" Journal of the science of food and agriculture 79: 232-236, 1999.

Cao et al., "Purification and characterization of soluble starch syntheses from maize endosperm" Archives of Biochemistry and Biophysics, 373: 135-146, 2000.

Cao et al., "Identification of the soluble starch synthase activities of maize endosperm" Plant Physiol. 120: 205-215, 1999.

Clarke and Rahman, "A microarray analysis of wheat grain hardness" Theoretical and Applied Genetics, 110: 1259-1267, 2005.

Comai et al., Efficient discovery of DNA polymorphisms in natural populations by Ecotilling Plant J. 37: 778-786, 2004.

Craig et al., Mutations in the gene encoding starch synthase II profoundly alter amylopectin structure in pea embryos Plant Cell 10: 413-426, 1998.

Deijman et al., "Interaction of a DNA binding factor with the 5'-flanking region of an ethylene-responsive fruit ripening gene from tomato" EMBO J., 2: 3315-3320, 1998.

Eagles et al., "Implementation of markers in Australian wheat breeding" Aust. J. Agric. Res. 52:1 349-356, 2001.

Fromm et al., "Expression of genes transferred into monocot and dicot plant cells by electroporation" Proc. Natl. Acad. Sci. U.S.A. 82: 5824, 1985.

Geo and Chibbar, "Isolation, characterization, and expression analysis of starch synthase IIa cDNA from wheat (Triticum aestivum L.)" Genome 43: 768-775, 2000.

Gao et al., "Characterization of dulli, a maize gene coding for a novel starch synthase" Plant Cell, 10: 399-412, 1998.

Garfinkel et al., "Genetic Analysis of Crown Galli: Fine structure Map of the T-DNA by Site-DirectedMutagenesis" Cell, 27: 143-153, 1983.

Guerin et al., "Release and activation of barley beta-amylase by malt endopeptidases" Journal of Cereal Science, 15: 5-14, 1992.

Harayama, "Artificial evolution by DNA shuffling" Trends Biotechnol. 16: 76-82, 1998.

Harvey et al., "Regulation of genes encoding beta-D-glucan glucohydrolases in barley (Hordeum vulgare)" Physiologia Plantarum 113: 108-120, 2001.

Haseloff and Gerlach, "Simple RNA enzymes with new and highly specific endoribonuclease activities" Nature 334: 585-591, 1988.

Hedman and Boyer, "Gene dosage at the amylose-extender locus of maize: effects on the levels of starch branching enzymes" Biochemical Genetics, 20: 483-492, 1982.

Hellwege et al., "Transgenic potato (Solanum tuberosum) tubers synthesize the full spectrum of inulin molecules naturally occurring in globe artichoke (Cynara scolymus) roots" Proc. Natl. Acad. Sci. U.S.A. 97: 8699-8704, 2000.

Hendrix et al., "Isobemisiose: an unusual trisaccharide abundant in the silverleaf whitefly, Bemisia argentifolii" J. Insect Physiol., 47: 423-432, 2001.

Henikoff et al., "Tilling. Traditional mutagenesis meets functional genomics" Plant Physiol. 135: 630-636,2004.

Henry and Saini "Characterization of Cereal Sugars and Oligozaccharides" Cereal Chem. 66(5):362-365.

Hinchee et al., "Production of Transgenic Soybean Plants Using Agrobacterium-Mediated DNA Transfer" Biotech. 6: 915, 1988.

Hoekema et al., "A binary plant vector strategy based on separation of vir- and T-region of the Agrobacterium tumefaciens Ti-plasmid" Nature, 303: 179, 1983.

Hrmova and Fincher, "Structure-function relationships of beta-D-glucan endo- and exohydrolases from higher plants" Plant Molecular Biology, 47: 73-91, 2001.

James et al., "Characterization of the maize gene sugaryl, a determinant of starch composition in kernels" Plant Cell, 7: 417-429, 1995.

Joshi, "An inspection of the domain between putative TATA box and translation start site in 79 plant genes" Nucl. Acid Res. 15: 6643, 1987.

Kaur and Gupta, "Applications of inulin and oligofructose in health and nutrition" J. Biosci. 27: 703-714, 2002.

Klein et al., "High-velocity microprojectiles for delivering nucleic acids into living cells" Nature, 327: 70, 1987.

Konik-Rose et al., "Evaluation of the 40 mg Swelling Test for Measuring Starch Functionality" Starch/die Starke 53,:14-20, 2001.

Kubo et al., "The Starch-Debranching Enzymes Isoamylase and Pullulanase Are Both Involved in Amylopectin Biosynthesis in Rice Endosperm" Plant Physiology, 121: 399-409, 1999.

Lai et al., "Characterization of the maize endosperm transcriptome and its comparison to the rice genome" Genome Res. 14: 1932-1937, 2004.

Langridge et al., "Trends in genetic and genome analysis of wheat: a review" Aust. J. Agric. Res. 52: 1043-1077, 2001.

Li et al. , "The Localization and Expression of the Class II Starch Synthases of Wheat," Plant Physiology 120:1147-1155 (1999).

Li et al., "The structure and expression of the wheat starch synthase III gene: motifs in the expressed gene define the lineage of the starch synthase III gene family" Plant Physiology, 123: 613-624, 2000.

Li et al. , "Cloning and Characterization of a Gene Encoding Wheat Starch Synthase I," Theor. Applied Genet. 98: 1208-1216 (1999).

Libessart et al., "Storage, Photosynthesis, and Growth: The Conditional Nature of Mutations Affecting Starch Synthesis and Structure in Chlamydomonas" Plant Cell 7(8): 1117-1127, 1995.

Lunn and Hatch, "Primary partitioning and storage of photosynthate in sucrose and starch in leaves of C4 plants" Planta 197: 385-391, 1995.

MacGregor et al., "Changes in barley kernels during growth and maturation" Cereal Chemistry, 48: 255-269, 1971.

Medberry et al., "The Commelina yellow mottle virus promoter is a strong promoter in vascular and reproductive tissues" Plant Cell, 4: 185-192, 1992.

Medberry et al., "Identification of cis elements involved in Conunelina yellow mottle virus promoter activity" Plant J. 3: 619-626, 1993.

Millar and Waterhouse, "Plant and animal microRNAs: similarities and differences" Funct Integr Genomics, 5:129-135, 2005.

Mizuno et al., "Starch branching enzymes from immature rice seeds" Journal of Biochemistry, 112: 643-651, 1992.

Morell et al., "Analysis of starch structure using fluorophore-assisted carbohydrate electrophoresis" Electrophoresis, 19: 2603-2611, 1998.

Moshfegh et al., "Presence of inulin and oligofructose in the diets of Americans" J Nutr 129(Suppl): 1407S-11S, 1999.

Myers et al. , Recent • Progress toward Understanding Biosynthesis of the Amylopection Crystal, Plant Physiology 122: 989-997 (2000).

(56) References Cited

OTHER PUBLICATIONS

Nakamura et al., "Essential amino acids of starch synthase IIa differentiate amylopectin structure and starch quality between japonica and indica rice varieties" Plant Mol. Bioi, 58: 213-227, 2005.
Needleman and Wunsch, "A general method applicable to the search for similarities in the amino acid sequence of two proteins" J. Mol. Biol. 48: 443-453, 1970.
Niedz et al. "Green Fluorescent Protein: an in vivo reporter of plant gene expression." Plant Cell Reports, 14: 403, 1995.
Ow et al., "Transient and stable expression of the firefly luciferase gene in plant cells and transgenic plants" Science, 234: 856-9, 1986.
Pasquinelli et al., "MicroRNAs: a developing story" Curr Opin Genet Develop 15:200-205, 2005.
Perriman et al., "Extended target-site specificity for a hammerhead ribozyme" Gene, 113: 157-163, 1992.
Prasher et al., "Cloning and expression of the cDNA coding for aequorin, a bioluminescent calcium-binding protein" Biochem. Biophys. Res. Comm. 126:1259-68, 1985.
Prosky et al. "Determination of Total Dietary Fiber in Foods and Food Products: Collaborative Study" J. Assoc. Off. Anal. Chem. 68(4):677-679 , 1985.
Prosky and Hoebregs "Methods to Determine Food Inulin and Oligofructose" J. Nutr. 129(7):1418S-1423s, 1999.
Regina A., (2006) "High-amylose wheat generated by RNA interference improves indices of large-bowel health in rats", PNAS, vol. 103, pp. 3546-3551.
Remington's Pharmaceutical Sciences, 18th Ed. Mack Publishing, Company, Easton, Pa., U.S.A., 1990.
Ruuska et al., "Genotypic variation in water-soluble carbohydrate accumulation in wheat" Functional Plant Biology 33: 799-809, 2006.
Salomon et al., "Genetic identification of functions of TR-DNA transcripts in octopine crown galls" EMBO J., 3: 141-146, 1984.
Sambrook et al., Molecular Cloning: A Laboratory Manual (2nd ed.). Cold Spring Harbour Laboratory, Cold Spring Harbour, N.Y., Plasmid Vectors, 1.101-1.105, 1989.
Sambrook et al., Molecular Cloning: A Laboratory Manual (2nd ed.). Cold Spring Harbour Laboratory, Cold Spring Harbour, N.Y., Expression of Cloned Genes in Cultured Mammalian Cells, 16.-16.81, 1989.
Sambrook et al., Molecular Cloning: A Laboratory Manual (2nd ed.). Cold Spring Harbour Laboratory, Cold Spring Harbour, N.Y., Expression of Cloned Genes in *Escherichia coli*, Chapter 17, 1989.
Schenk et al., "Coordinated plant defense responses in Arabidopsis revealed by microarray analysis" Proc. Natl. Acad. Sci. U.S.A. 97:11655-11660, 2000.
Schnyder, "The role of carbohydrate storage and redistribution in the source-sink relations of wheat and barley during grain filling—a review" New Phytol 123: 233-245, 1993.
Schulman and Kaamtiovirta, Purification of Barley Starch by Protein Extraction. Starch, 1991, 43(10):387-389.
Senior, "Uses of plant gene silencing" Biotech. Genet. Engin. Revs. 15: 79-119, 1998.
Sevenier et al., "High level fructan accumulation in a transgenic sugar beet" Nature Biotechnol. 16: 843-846, 1998.
Sharp et al., "Implementation of markers in Australian wheat breeding" Aust J Agric Res 52: 1357-1366, 2001.
Shimamoto et al., "Fertile transgenic rice plants regenerated from transformed protoplasts" Nature, 338: 274-276, 1989.
Shimbata et al., "Mutations in wheat starch synthase II genes and PCR-based selection of a SGP-1 null line" Theor. Appl. Genet. 111: 1072-1079, 2005.
Shippy et al., "The hairpin ribozyme. Discovery, mechanism, and development for gene therapy" Mol. Biotech, 12: 117-129, 1999.
Slade and Knauf, "TILLING moves beyond functional genomics into crop improvement" Transgenic Res. 14: 109-115, 2005.
Smith et al., "Total silencing by intron-spliced hairpin RNAs" Nature, 407: 319-320, 2000.
Stalker et al., "Herbicide resistance in transgenic plants expressing a bacterial detoxification gene" Science, 242: 419-23, 1988.
Sun et al., Identification of four starch-branching enzymes in barley endosperm: partial purification of forms I, IIa and IIb. New Phytol. 137:215-222 (1997).
Thillet et al., "Site-directed mutagenesis of mouse dihydrofolate reductase. Mutants with increased resistance to methotrexate and trimethoprim" J. Biol. Chem. 263: 12500-8, 1988.
Thompson et al., "Phosphorylation and metabolism of sucrose and its five linkage-isomeric alpha-D-glucosyl-D-fructoses by Klebsiella pneumoniae" Carbohydrate Res., 331: 149-161, 2001.
Tingay et al., "Agrobacterium tumefaciens-mediated barley transformation" Plant J. 11: 1369-1376, 1997.
Topping et al., "Resistant Starch and Health—Himalaya 292, a Novel Barley Cultivar to Deliver Benefits to Consumers" Starch/Starke 55: 539-545, 2003.
Tsuchiya et al., "Biosynthesis of $(1 \rightarrow 3)$, $(1 \rightarrow 4)$-$\beta$-glucan in developing endosperms of barley (Hordeum vulgare) Physiologia Plantarum" Physiologia Plantarum 125: 181-191, 2005.
Van den Ende et al., "Fructan 1-exohydrolases. beta-(2,1)-trimmers during graminan biosynthesis in stems of wheat? Purification, characterization, mass mapping, and cloning of two fructan 1-exchydrolase isoforms" Plant Physiol. 131 (2): 621-631, 2003.
Veronese et al., "Mechanism of sucrose conversion by the sucrose isomerase of Serratia plymuthica ATCC 15928" Enz. Microbial Tech., 24: 263-269, 1999.
Wan and Lemaux, "Generation of Large Numbers of Independently Transformed Fertile Barley Plants" Plant Physiol. 104: 37-48, 1994.
Waterhouse et al. "Virus resistance and gene silencing in plants can be induced by simultaneous expression of sense and antisense RNA" Proc. Natl. Acad. Sci. U.S.A. 95:13959-13964, 1998.
White and Secor, "Chromatographic evidence for the occurrence of a fructosyl raffinose in wheat flour and wheat" Arch Biochem Biophys. 44: 244-5, 1953.
Wilson et al., "New normalization methods for cDNA microarray data" Bioinformatics 19: 1325-1332, 2003.
Winter and Huber, "Regulation of Sucrose Metabolism in Higher Plants: Localization and Regulation of Activity of Key Enzymes" Critical Reviews in Plant Sciences 19: 31-67, 2000.
Yamakawa et al., "Comprehensive expression profiling of rice grain filling-related genes under high temperature using DNA microarray" Plant Physiol 144: 258-277, 2007.
Yamamori et al. , "Genetic Elimination of a Starch Granule Protein, SGP-1, of Wheat Generates an Altered Starch with Apparent High Amylase, " TAG Theoretical and Applied Genetics 101: 21-29 (2000).
Zwar and Chandler, $\alpha$-Amylose production and leave protein synthesis in a gibberellin-responsive dwarf mutant of 'Himalaya' barley (Hordeum vulgare L.). Planta, 1995, 197:39-48.
International Report on Patentability, dated Aug. 6, 2013 in connection with PCT International Patent Application No. PCT/AU2012/000098.
International Search Report, dated May 14, 2012 in connection with PCT International Patent Application No. PCT/AU2012/000098.
Fujita et al., Characterization of SSIIIa-Deficient Mutants of Rice: The Function of SSIIIa and Pleiotropic Effects by SSIIIa Deficiency in the Rice Endosperm. Plant Physiology, 144: 2009-2023 (2007).
Li et al., The barley amo1 locus is tightly linked to the starch synthase IIIa gene and negatively regulates expression of granule-bound starch synthetic genes. Journal of Experimental Botany 62: 5217-5231 (2011).
Newman et al., Comparative Nutritive Value of Glacier and High Amylose Glacier Barleys. Journal of Animal Science, 47:448-456 (1978).
Zhang et al., Overlapping functions of the starch synthases SSII and SSIII in amylopectin biosynthesis in Arabidopsis. BMC Plant Biology 8:96 (2008).
File History of U.S. Pat. No. 7,812,221, Regina et al., issued Oct. 12, 2010 (U.S. Appl. No. 10/881,808, filed Jun. 20, 2004).
File History of U.S. Patent Application Publication No. 2011-0070352, Regina et al., published Mar. 24, 2011 (U.S. Appl. No. 12/881,040, filed Sep. 13, 2010).
File History of U.S. Pat. No. 7,700,139, Bird et al., issued Apr. 20, 2010 (U.S. Appl. No. 11/324,063, filed Dec. 30, 2005).

(56) References Cited

OTHER PUBLICATIONS

File History of U.S. Patent Application Publication No. 2006-0286186, Bird et al., published Dec. 21, 2006 (U.S. Appl. No. 11/417,330, filed May 2, 2006).
File History of U.S. Patent Application Publication No. US 2011-0212916, Bird et al., published Sep. 1, 2011 (U.S. Appl. No. 12/799,013, filed Apr. 16, 2010).
File History of U.S. Pat. No. 7,790,955, Li et al., issued Sep. 7, 2010 (U.S. Appl. No. 10/577,564, filed Apr. 27, 2006.
File History of U.S. Patent Application Publication No. 2011-0059225, Li et al., published Mar. 10, 2011 (U.S. Appl. No. 12/806,167, filed Aug. 6, 2010).
File History of U.S. Pat. No. 7,888,499, Morell et al., issued Feb. 15, 2011 (U.S. Appl. No. 10/416,439, filed Dec. 5, 3003).
File History of U.S. Pat. No. 7,001,771, Morell et al., issued Feb. 21, 2006 (U.S. Appl. No. 10/018,418, filed May 9, 2002).
File History of U.S. Pat. No. 7,700,826, Morell et al., issued Apr. 20, 2010 (U.S. Appl. No. 11/231,599, filed Sep. 21, 2005).
File History of U.S. Pat. No. 7,521,593, Regina et al., issued Apr. 21, 2009 (U.S. Appl. No. 10/434,893, filed May 9, 2003).
File History of U.S. Pat. No. 7,919,132, Regina et al., issued Apr. 5, 2011 (U.S. Appl. No. 12/384,823, filed Apr. 9, 2009).
File History of U.S. Pat. No. 7,667,114, Morell et al., issued Feb. 23, 2010 (U.S. Appl. No. 10/204,347, filed Feb. 20, 2002).
File History of U.S. Patent Application Publication No. 2011-0010807, Morell et al., published Jan. 13, 2011 (U.S. Appl. No. 12/707,437, filed Feb. 17, 2010).
File History of U.S. Patent Application Publication No. 2010-0330253, Morell et al., published Dec. 20, 2010 (U.S. Appl. No. 12/800,143, filed May 10, 2010).
File History of U.S. Patent Application Publication No. 2012-0074247, Regina et al., published Mar. 29, 2012 (U.S. Appl. No. 13/243,220).
File History of U.S. Patent Application Publication No. 2013-0156924, Morell et al., published Jun. 20, 2013.
File History of U.S. Patent Application Publication No. 2012-0129805, Li et al., published May 24, 2012.
File History of U.S. Patent Application Publication No. 2012-0114770, Regina at el., published May 10, 2012.
File History of U.S. Patent Application Publication No. 2012-0266267, Li et al., published Oct. 18, 2012.
Abel et al., GenBank Accession #Y10416 (Jan. 1997) S. Tuberosum mRNA for Soluble Starch Synthase.
Abel, G.J.W. et al., Cloning and functional analysis of a cDNA encoding a novel 139 kDa Starch Synthase from Potato (solanum tuberosum L.). Plant J. 10(6): 981-991 (1996).
Ainsworth, C. et al., Expression, organization and structure of the genes encoding the waxy protein (granule-bound starch synthase) in wheat. Plant Mol. Biol. 22:67-82 (1993).
Anchikhorova, Methods for crying out port experiements with granulated fertilizers. Doklady Vsesoyuznoi Akademii Sel'skokhozyaistvennykh Nauk V.I. Lenina (1971), vol. 8, pp. 20-22). (Abstract in English).
Baba, T. et al., Identification, cDNA cloning and gene expression of soluble starch synthase in rice (oryza stativa L.) Immature Seeds. Plant Physiol. 103:565-573 (1993).
Banks et al., Studies on Starches of High Amylose Content. Starch 26: 289-300 (1974).
Batey and Curtin, Measurement of Amylose/Amylopectin Ratio by High-Performance Liquid Chromatography. Starch 48: 338-344 (1996).
Bhullar et al., GenBank Accession #CAB40374 (Apr. 1999) Starch synthase isoform SS III [Vigna unguiculate].
Blauth et al., Identification of Mutator Insertional Mutants of Starch-Branching Enzyme 2a in Corn. Plant Physiology 125:1396-1405 (2001).
Block et al., GenBank Accession #U48227 (Jun. 1996) Triticum aestivum soublé starch synthase mRNA, partial cds.

Boyer and Preiss, Evidence for Independent Genetic Control of the Multiple Forms of Maize Endosperm Branching Enzymes and Starch Synthases. Plant Physiology 67: 1141-1145 (1981).
Calvert et al., High Amylose Glacier Barley in Swine Diets. Nutritional Reports International. 23:29-36 (1981).
Clarke et al., Gene expression in a starch synthase IIa mutant of barley: changes in the level of gene transcription and grain composition. Functional Integrated Genomics (2008) 8:211-221.
Craig et al., Mutations in the Gene Encoding Starch Synthase II Profoundly Alter Amylopectin Structure in Pea Embryos. The Plant Cell 10:413-426 (1998).
Denyer, K. et al., Identification of Multiple Isoforms of Soluble and Granule Bound Starch Synthase in Developing Wheat Endosperm. Planta 196: 256-265 (1995).
D'Hulst et al., GenBank Accession #AAC17969 (Nov. 2001) Granule-bound starch synthase I precursor [Chlamydomonas reinhardtii].
Dry, I. et al., Characterization of cDNAs encoding two isoforms of granule-bound synthase which show differential expression in developing storage organs of pea and potato. Plant J. 2 (2): 193-202 (1992).
Edwards et al., Biochemical and Molecular Characterization of a Novel Starch Synthase from Potato Tubers. Plant J. 8 (2): 283-294 (1995).
Flipse et al., Introduction of Sense and Antisense cDNAfor Branching Enzyme in the Amylose-Free Potato Mutant Leads to Physico-Chemicai Changes in the Starch. Plant a 198: 340-347 (1996).
Fujita et al., Grain and Starch Characteristics of the Double Recessive Lines for Amylose-free and High Amylose Gene in Barley. Breeding Science 49: 217-219 (1999).
Fujita et al., Antisense Inhibition of Isoamylase Alters the Structure of Amylopectin and the Physiochemical Properties of Starch in Rice Endosperm. Plant Coll Physiol. 44(6):607-618 (2003).
Gao et al., GenBank Accession #AAC14014 (Apr. 1998) Starch synthase DULL 1 [Zea mays].
Gao et al., GenBank Accession #AAC14015 (Apr. 1998) Starch synthase DULL 1 [Zea mays].
Gao et al., Triticum aestivum mRNA for Starch Synthase IIa-2 (wSs2a-2). EMBL Abstract Accession No. AJ269503, Jul. 6, 2000.
Gao et al., GenBank Accession #AJ26502 (Apr. 2002) Triticum aestivum mRNA for starch synthase Iia-1 (wSs2a-1 gene).
Gao et al., GenBank Accession #CAB86618 (Apr. 2002) Starch synthase Iia-1 [Triticum aestivum].
Gillespie, K., Type 1 diabetes: pathogenesis and prevention. CMAJ, vol. 175, pp. 165-170 (2006).
Goering and DeHass, A Comparison of the Properties of Large- and Small-Granule Starch Isolated from Several Isogenic Lines of Barley. Cereal Chemistry 51:573-578 (1974).
Harn et al., Isolation and Characterization of the zSSIIA and zSSIIb Starch Synthase cDNA Clones from Maize Endosperm. Plant Mol. Biol. 37:639-649 (1998).
Holmes et al., Henderson's Dictionary of Biological Terms, 9th Ed., Van Nostrand Reinhold Co., New York, p. 218 (1979).
Jansson et al., Cloning, Characterization and Modification of Genes Encoding Starch Branching Enzymers in Barley. Starch: Structure and Functionality. Royal Society of Chemistry, London, pp. 196-203 (1997).
Jarvi and Eslick, Shrunken Endosperm Mutants in Barley. Crop Science 15:363-366 (1975).
Klosgen, et al., Molecular Analysis of the Waxy Locus of Zea mays, Mol. Gen. Genet. 203: 237-244 (1986).
Knight, et al., Molecular Cloning of Starch Synthase I from Maize (w64) Endosperm and Expression in Escherichia coli. Plant J. 14 (5) : 613-622 (1998).
Kull et al., Genetic Engineering of Potato Starch Composition: Inhibition of Amylose Biosynthesis in Tubers from Transgentic Potato Lines by the Expression of Antisense Sequences of the Gene for Granule-bound Starch Synthase. J. Genet. Breed. 49: 69-76 (1995).
Li et al., Triticum aestivum Starch Synthase IIA mRNA, Complete cds. EMBL Abstract Accession No. AF155217 (1999).

(56) References Cited

OTHER PUBLICATIONS

Li et al., The structural organisation of the gene encoding class II starch synthase of wheat and barley and the evolution of the genes encoding starch synthases in plants. Funct Integr Genomics 3:76-85 (2003).

Liu et al., Stable Inheritance of the Antisense Waxy Gene in Transgenic Rice with Reduced Amylose Level and Improved Quality. Transgenic Research, 12:71-82, (2003).

Lorberth et al., Inhibition of a starch-granule-bound protein leads to modified starch and repression of cold sweetening. Nature Biotechnology, 16(1):473-477 (1998).

Mazzolini et al., Assaying synthetic ribozymes in plants: high-level expression of a functional hammerhead structure fails to inhibit target gene activity in transiently transformed protoplasts. Plant Mol. Biol. 20: 715-731 (1992).

Miao, Hongmei et al., Evaluation and Characterization of an Endosperm-Specific sbella Promoter in Wheat II Chinese Science Bulletin. vol. 49, No. 6, pp. 579-585 (2004).

Mizuno et al., Alteration of the Structural Properties of Starch Components by the Lack of an Isoform of Starch Branching Enzyme in Rice Seeds. J. Biol. Chern. 268 (25): 19084-19091 (1993).

Morell et al., The Biochemistry and Molecular Biology of Starch Synthesis in Cereals. Aust. J. Plant. Physiol. 22: 647-660 (1995).

Nakamura Y., Towards a Better Understanding of the Metabolic System for Amylopectin Biosynthesis in Plants: Rice Endosperm as s Model Tissue. Plant Cell Physiology 43 (7): 718-725 (2002).

Nishi et al., Biochemical and Genetic Analysis of the Effects of Amylose-Extender Mutation in Rice Endosperm. Plant Physiology 127:459-472 (2001).

Okagaki R. J., Nucleotide Sequence of a Long cDNA from the Rice Waxy Gene. Plant Molecular Biology 19: 513-516 (1992).

Puchta, Gene Replacement by Homologous Recombination in Plants. Plant Mol. Biol. 48: 173-182 (2002).

Rahman et al., GenBank Accession #AF076680 (May 1999) Aegilops tauschii starch branching enzyme-I (SBE-1) gene, complete cds.

Rahman, S. et al., The Major Proteins of Wheat Endosperm Starch Granules. Aust. J. Plant Physiol. 22:793-803 (1995).

Rahman, S. et al., A Complex Arrangement of Genes at a Starch Branching Enzyme I Locus in the D-genome Donor of wheat. Genome 40: 465-474 (1997).

Rahman, S. et al., Characterisation of a Gene Encoding Wheat Endosperm Starch Branching Enzyme-I. Theor. Appl. Genet. 98: 156-163 (1999).

Rahman, S. et al., Comparison of Starch-Branching Enzyme Genes Reveals Evolutionary Relationships Among Isoforms. Characterization of a Gene for StarchBranching Enzyme IIa from the Wheat D Genome Donor Aegilops tauschii II Plant Physiology, vol. 125, pp. 1314-1324 (2001).

Regina A., High-amylose wheat generated by RNA interference improves indices of large-bowel health in rats. PNAS, vol. 103, pp. 3546-3551 (2006).

Safford, et al., Consequences of Antisense RNA Inhibition of Starch Branching Enzyme Activity on Properties of Potato Starch. Carbohydrate Polymers 35: 155-168 (1998).

Sathish et al., Cloning and Anti-Sense RNA Constructs of a Starch Branching Enzyme Gene From Barley Endosperm. Photosynthesis: from Light to Biosphere vol. V. P. Mathis (ed.) pp. 313-316 (1995).

Schondelmaier et al., Genetical Studies in the Mode of Inheritance and Localization of the amol (High Amylose) Gene in Barley. Plant Breeding 109: 274-280 (1992).

Schulman et al., Structural analysis of starch from normal and shx (shrunken endosperm) barley (Hordeum vulgare L.). Carbohydrate Research, 275:361-369 (1995).

Schulman and Kammiovirta, Purification of Barley Starch by Protein Extraction. Starch, 43(10):387-389 (1991).

Schwall, et al., Production of Very-High-Amylose Potato Starch by Inhibition of SBE A and B. Nature Biotechnology 18: 551-554 (2000).

Sestili et al., Increasing the amylose content of durum wheat through silencing of the SBEIIa genes. BMC Plant Biol. 10:144 (2010).

Shannon and Garwood, In Starch: Chemistry and Technology. Whistler et al., eds, Academic Press, Orlando, FL, 25-86 (1984).

Sidebottom et al., Characterization of the Difference of Starch Branching Enzyme Activities in Normal and Low-Amylopectin Maize during Kernel Development. Journal of Cereal Science 27: 279-287 (1998).

Slade et al., Development of High Amylose Wheat Through TILLING. BMC Plant Biology, 12:69-100 (2012).

Sun et al., Identification of Four Starch-Branching Enzymes in Barley Endosperm: Partial Purification of forms I, IIa and IIb. New Phytol. 137:215-222 (1997).

Sun et al., The Two Genes Encoding Starch-Branching Enzymes IIa and IIb Are Differentially Expressed in Barley. Plant Physiology 118:37-49 (1998).

Sundberg et al., Glycaemic Responses and Hyopcholesterolaemic Effects of High-Amylose Barley Diets on Broiler Chicks. J. Sci. Food Agric. 76:457-463 (1998).

Takaoka, M. et al., Structural characterization of high molecular weight starch granule-bound proteins in wheat (Triticum aestivum L.). J. Agric. Food Chem. 45: 2929-2934 (1997).

Terada at al., Efficient Gene Targeting by Homologous Recombination in Rice. Nature Biotech. 20: 1030-1034 (1997).

Tester, R.F. The effects of ambient temperature during the Grain-filling period on the composition and properties of starch and four barley genotypes. Journal of Cereal Science 13:113-127 (1991).

Tester, T.F. Influence of growth conditions on barley starch properties. Biological Macromolecules 21:37-45 (1997).

Tetlow et al., Recent developments in understanding the regulation of starch metabolism in higher plants. Journal of Experimental Botany 55(406):2131-2145 (2004).

Thomas et al., Size Constraints for Targeting Post-Transcriptional Gene Silencing and for RNA-directed Methylation in Nicotiana benthamiana Using a Potato Virus X Vector. Plant J. 25 : 417-425 (2001).

USDA, ARS, National Genetic Resources Program. Germplasm Resources Information Network (GRIN) [Online Database] National Germplasm Resources Laboratory, Beltsville, Maryland (www.ars-grin.gov/npgs/), GRIN System [Accession No. GSHO 2476, Jun. 23, 1997).

Van der Leij et al., Sequence of the Structural Gene for Granule-Bound Starch Synthase of Potato (Solanum Tuberosum L.) and Evidence for a Single Point Deletion in the amf allele. Mol. Gen. Genet. 228: 240-248 (1991).

Vrinten and Nakamura, Wheat Granule-Bound Starch Synthase I and II Are Encoded by Separate Genes That Are Expressed in Different Tissues. Plant Physiology 122:255-263 (2000).

Walker and Meritt, Genetic Control of Abnormal Starch Granules and High Amylose Content in a Mutant of Glacier Barley. Nature 221:482-484 (1969).

Walter et al., GenBank Accession #AAB17085 (Oct. 1996) Starch Synthase.

Walter et al., GenBank Accession #U66377 (Oct. 1996) Triticum aestivum soluble starch synthase mRNA; partial cds.

Wasserman et al., Microstructure, Thermal properties and susceptibility of the high amylose wheat starch to enzymatic hydrolysis: A new material for resistant starch (SRIII) production. Polish Journal of Food and Nutrition Sciences vol. 13-54, No. 2, pp. 151-156 (2004).

Wei et al., C-Type Starch from High-Amylose Rice Resistant Starch Granules Modified by Antisense RNA Inhibition of Starch Branching Enzyme. Journal of Agricultural and Food Chemistry, 58: 7383-7388 (2010).

Yamamori and Endo, Variation of Starch Granule Proteins and Chromosome Mapping of Their Coding Genes in Common Wheat. Theor. Appl. Genet. 93: 275-181 (1996).

Yamamori et al., Genetic Elimination of a Starch Granule Protein, SGP-1, of Wheat Generates an Altered Starch with Apparent High Amylose. TAG Theoretical and Applied Genetics 101: 21-29 (2000).

(56) References Cited

OTHER PUBLICATIONS

Yamamori, Selection of a Wheat Lacking a Putative Enzyme for Starch Synthesis, SGP-1. Proc. 9th in Wheat Gen. Symp. 4:300-302 (1998).
Yoshimoto et al., Molecular Structure and Some Physiochemical Properties of High-Amylose Barley Starches. Cereal Chem, 77(3):279-285 (2000).
Zcbel et al., Starch Gelatinization: An X-ray Diffraction Study. Cereal Chem, 65(6):443-446 (1988).
Zobel, H. F., Starch Crystal Transformations and Their Industrial Importance. Starch, 40(1): 1-7 (1988).
Tang et al. Physicochemical properties and structure of large, medium and small granule starches in fractions of normal barley endosperm. Carbohydrate Research 330: 241-248 (2001).
Apr. 9, 2013 Response to First Examination Report, filed in connection with Australian Patent Application No. 2009200577.
May 10, 2013 Second Examination Report, issued in connection with Australian Patent Application No. 2009200577.
May 21, 2013 Response to Second Examination Report filed in connection with Australian Patent Application No. 2009200577.
Jul. 17, 2018 Regina Notice of Filing Priority Statement, filed in connection with Interference No. 106,094.
Jul. 17, 2018 Regina Motion 2 (for Judgment Denying Slade The Benefit of U.S. Appl. Nos. 14/825,369, 13/633,588 and/or U.S. Appl No. 61/542,953), filed in connection with Interference No. 106,094.
Jul. 17, 2018 Regina Exhibit List, filed in connection with Interference No. 106,094.
Jul. 17, 2018 Regina Reply 1 (For Judgment That Slade's Involved Claims are Unpatentable Under 35 U.S.C. §112, First Paragraph), filed in connection with Interference No. 106,094.
Jul. 17, 2018 Slade Notice of Filing of Slade Priority Statement, filed in connection with Interference No. 106,094.
Jul. 17, 2018 Slade Substantive Motion 2 (for judgment for lack of enablement), filed in connection with Interference No. 106,094.
Jul. 17, 2018 Slade Substantive Motion 3 (for judgment for lack of written description), filed in connection with Interference No. 106,094.
Jul. 17, 2018 Slade Exhibit List 2, filed in connection with Interference No. 106,094.
Jul. 17, 2018 Slade Substantive Motion 1 (for judgment attacking accorded benefit), filed in connection with Interference No. 106,094.
Regina Exhibit No. 2028, The Gregg Reference Manual: *A Manual of Style, Grammar Usage and Formatting*, by William A. Sabin, p. 257 (10th ed. 2005), filed in connection with Interference No. 106,094.
Regina Exhibit No. 2029, Interview Summary filed in U.S. Appl. No. 13/668,177 dated Dec. 31, 2015, filed in connection with Interference No. 106,094.
Slade Exhibit No. 1025, Second Declaration of Michael J. Giroux, Ph.D., filed in connection with Interference No. 106,094.
Slade Exhibit No. 1027, Redline Comparison of U.S. Pat. No. 9,357,722 to U.S. Appl. No. 61/645,530, filed connection with Interference No. 106,094.
Slade Exhibit No. 1028, Redline Comparison of U.S. Appl. No. 61/645,530 to U.S. Appl. No. 61/556,051, filed in connection with Interference No. 106,094.
Slade Exhibit No. 1029, Second Declaration of Carla M. Ford, filed in connection with Interference No. 106,094.
Slade Exhibit No. 1030, Transcript of the Jul. 11, 2018 Deposition of Michael Giroux, Ph.D., filed in connection with Interference No. 106,094.
Slade Exhibit No. 1031, Trictium aestivum SBEIIa gene for starch branching enzyme IIa, cultivar Chinese Spring, allele SBEIIa-A, exons 1-22, filed in connection with Interference No. 106,094.

\* cited by examiner

HIGH FRUCTAN CEREAL PLANTS

This application is a divisional of U.S. Ser. No. 13/008,746, filed Jan. 18, 2011, now allowed, which is a continuation-in-part of PCT International Application No. PCT/AU2009/000911, filed Jul. 16, 2009, which claims the benefit of U.S. Provisional Applications Nos. 61/135,111, filed Jul. 17, 2008 and 61/135,361, filed Jul. 18, 2008, and claims priority of Australian Patent Application No. 2009200577, filed Feb. 13, 2009, the contents of each of which are hereby incorporated by reference in their entirety into this application.

This application incorporates-by-reference nucleotide and/or amino acid sequences which are present in the file named "170808_79593-BZ_Substitute_Sequence_Listing_REL_txt" which is 114 kilobytes in size, and which was created Aug. 8, 2017 in the IBM-PCT machine format, having an operating system compatability with MS-Windows, which is contained in the text file filed Aug. 8, 2017 as part of this application.

FIELD

The present specification describes cereal plants having a high level of fructans useful for the production of a range of food, beverage, nutraceutical and pharmaceutical products.

BACKGROUND

Fructans are polymers of fructose which are synthesized from sucrose and used as storage or reserve carbohydrates by many plants. They consist of fructosyl residues polymerized to sucrose, and therefore comprise fructosyl units in addition to one glucose unit. In view of this composition, they are highly soluble in water. The linkages between the fructosyl-residues are either exclusively of the β(1-2) type forming a linear molecule (inulin) in which the fructosyl residues are attached to the fructosyl residue of the sucrose starter, or of the β(2-6) type (levan), or both linkage types occur in branched fructans (graminans). Inulins are present in plants belonging to the Asterales (e.g. chicory) or the Liliaceae (e.g. onion). All fructans found in the dicotyledons, as well as some monocotyledons are of this type. The inulin in onion is termed neo-series inulin and has two linear β(1-2)-linked fructosyl chains, one attached to the C1 of the fructosyl residue of the sucrose and one attached to the C6 of the glucosyl residue of the sucrose. Levans are typically found in monocotyledons such as the Poaceae (e.g. grasses) and in almost all bacterial fructans. Graminans which consist of β(2-6)-linked fructose units with β(1-2) branches and are therefore more complex structures can also be present in cereals, and can be mixed with levans.

The degree of polymerization (DP) and distribution of linkage types are characteristic of different plant species. Since a range of DP are often seen in any one species, fructans typically show a disperse molecular weight. In contrast to the high molecular weight of fructan (levan, $1-5 \times 10^6$ Da) elaborated as an extracellular polysaccharide by some bacteria, plant fructans are much smaller by 2-3 orders of magnitude.

Fructans, rather than starch, occur naturally as the primary reserve carbohydrate in about 10-15% of higher plants including chicory, artichoke, asparagus, dahlia and the onion family, primarily in the perennating organs. Fructans are mostly stored in taproots (e.g. chicory) or tubers (e.g. dahlia, Jerusalem artichoke) or bulbs (e.g. onion). In grasses and cereals, fructans are mainly stored in the stems and leaf bases and used as a reserve carbohydrate for growth and seed production. Fructan also occurs as a temporary storage form in the vegetative tissues of forage grasses and cereals, but only at low levels in cereal grain. Despite this, wheat products are the primary source of fructan in the Western diet. Onions are the second largest source of naturally occurring fructans in the American diet, accounting for about 25% of total consumption (Moshfegh et al., *J Nutr.* 129 (Suppl): 1407S-11S, 1999).

Cereals such as wheat and barley accumulate, mainly in vegetative tissues, branched graminan-type fructans containing both β-(2,1) and β-(2,6) fructosyl linkages. These mostly have a low DP, such as 1-6-kestotetraose (bifurcose) which is the major fructan oligosaccharide accumulating in crown tissues and leaves of cereals exposed to chilling. Fructans are naturally present in various cereal grains (White and Secor, *Arch Biochem Biophys.* 44: 244-5, 1953; Henry and Saini, *Cereal Chem.* 66: 362-365, 1989; Schnyder, *New Phytol* 123: 233-245, 1993). Wheat grain has been reported to contain 0.6-2.6% (w/w) fructan.

Fructan is synthesized directly from sucrose as the sole precursor, without any known involvement of phosphorylated sugars or nucleotide co-factors, by the activity of specific fructosyltransferases (FTs). Synthesis generally occurs in vacuoles, outside of the plastid, and accumulation of fructan occurs in vacuoles of both photosynthetic and storage cells. Fructan synthesis in plants is initiated by a sucrose:sucrose 1-fructosyltransferase (1-SST, EC 2.4.1.99) using sucrose both as fructosyl donor and acceptor to produce 1-kestose, the shortest β(1-2) linked fructan) and glucose. 1-SST is found in all fructan-producing plants. Longer chain inulins are formed by the action of a second enzyme, fructan:fructan 6-fructosyltransferase (1-FFT, EC 2.4.1.100) which adds fructosyl residues by β(1-2) linkages. 1-FFT can use 1-kestose or fructans as fructose donors and therefore can transfer fructosyl residues from one fructan chain to another. Synthesis of the neo-series fructans requires fructan:fructan 6G-fructosyltransferases (6G-FFT). In the case of cereals such as wheat and barley, the next step of fructan synthesis is mediated by a sucrose:fructan 6-fructosyltransferase (6-SFT, EC 2.4.1.10) which transfers a fructosyl unit from a further sucrose molecule to fructan with a β(2-6) linkages, to extend the fructan polymer. Fructosyl transfer to 1-kestose, the smallest branched fructan, forms the tetrasaccharide bifurcose. It remains to be shown whether or not additional FTs are involved in fructan synthesis of grasses or cereals, but the combined action of 1-SST, 1-FFT, 6-FFT and 6G-FFT may be involved in graminan synthesis.

Many plant fructosyltransferases have been sequenced during the last few years, and the data clearly indicate a high homology to the vacuolar, acid invertases (β-fructosidases). These enzymes are all members of the glycoside hydrolase family 32 (GH32) and share three highly conserved regions characterized by the motifs (N/S)DPNG (also called β-fructosidase motif), RDP, and EC. The aspartate of the (N/S)DPNG motif provides a nucleophile in the catalysis, the glutamate of the EC-motif as a proton donor, and the aspartate of the RDP motif as transition state stabilizer in the transfructosylation reaction.

Fructans are catabolised by fructan exohydrolases (FEH; EC 3.2.1.80) which are specialized for fructans, and invertases such as acid invertase (EC 3.2.1.26) which hydrolyse sucrose. Genes encoding fructan exohydrolase have been isolated from wheat (Van den Ende et al., *Plant Physiol.* 131(2): 621-631, 2003). Other enzymes such as sucrose phosphate synthase (SPS; EC 2.4.1.14) and sucrose synthase (EC 2.4.1.13) are associated with fructan remobilization from the stems.

Fructans are non-starch carbohydrates with potentially beneficial effects as a food ingredient on human health (Tungland and Meyer, *Comprehensive Reviews in Food Science and Food Safety*, 2: 73-77, 2002; Ritsema and Smeekens, *Curr. Opin. Plant Biol.* 6: 223-230, 2003). The human digestive enzymes α-glucosidase, maltase, isomaltase and sucrase are not able to hydrolyse fructans because of the β-configuration of the fructan linkages. Furthermore, humans and other mammals lack the fructan exohydrolase enzymes that break down fructans and therefore dietary fructans avoid digestion in the small intestine and reach the large intestine intact. However, bacteria there are able to ferment fructans and thereby utilize them as, for example, an energy or carbon source for growth and production of short-chain fatty acids (SCFA). Dietary fructans therefore are able to stimulate the growth of beneficial bacteria such as bifidobacteria in the colon, which aids in prevention of bowel disorders such as constipation and infection by pathogenic gut bacteria. Dietary fructan also enhances nutrient absorption from diets, particularly calcium and iron, possibly via production of SCFA which in turn reduce luminal pH and modify calcium speciation and hence solubility, or exert a direct effect on the mucosal transport pathway, thereby improving the mineralization of bone and reducing the risk of iron deficiency anaemia. In addition, a high-fructan diet can improve the health of patients with diabetes and reduce the risk of colonic cancers by suppressing aberrant crypt foci which are precursors of colon cancer (Kaur and Gupta, *J. Biosci.* 27: 703-714, 2002).

Attempts have been made to enhance fructan production in transgenic plants by introduction and expression of genes encoding 1-SST and 1-FFT. Generally, fructan accumulation levels were less than 2% (w/w) for plants transformed with bacterial genes and less than 1% (w/w) using plant genes. In some exceptions, concentrations of 6-16% on a fresh weight basis were achieved and compare favourably with naturally occurring maximal starch and fructan content in leaves and tubers (Sevenier et al., *Nature Biotechnol.* 16: 843-846, 1998; Hellwege et al., *Proc. Natl. Acad. Sci. U.S.A.* 97: 8699-8704, 2000). Transformants expressing bacterial fructan synthesis genes sometimes exhibited aberrant phenotypes such as stunting, leaf bleaching, necrosis, reduced tuber number and mass, tuber cortex discoloration, reduction in starch accumulation, and chloroplast agglutination.

There is therefore a need for efficient production of fructan from plant sources at low cost.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

As used herein the singular forms "a", "an" and "the" include plural aspects unless the context clearly dictates otherwise. Thus, for example, reference to "a mutation" includes a single mutation, as well as two or more mutations; reference to "an agent" includes one agent, as well as two or more agents; and so forth.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of sequence identifiers is provided in Table 7. A sequence listing is provided after the claims.

Genes and other genetic material (e.g. mRNA, nucleic acid constructs etc) are represented herein in italics while their proteinaceous expression products are represented in non-italicised form. Thus, for example starch synthase II (SSII) polypeptide is the expression product of SSII nucleic acid sequences.

Representative examples of the nucleic acid and amino acid sequences of SSII molecules are provided in the sequence listing further described in Table 7. The terms SSII or SSII encompass all functional homologs in any plant species including cereal plants and including SSII molecules such as SSIIa, SSIIb, SSIIa-2, SSIIa-B, SSIIa-D and SSII-2 etc. In a particular embodiment, the SSII is SSIIa.

Bibliographic details of the publications referred to by author in this specification are collected at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Each embodiments described herein is to be applied mutatis mutandis to each any every embodiment unless specifically stated otherwise.

Accordingly in one embodiment, the present specification describes a method of producing a high-fructan product, wherein the method comprises: (i) obtaining or producing a cereal plant or grain or flour therefrom wherein the cereal grain or flour comprises at least 3%, preferably at least 4%, fructan as a percentage of the cereal grain or flour weight; and (ii) processing the plant, grain or flour to produce the product.

In particular embodiments, the grain is characterized by a combination of two parameters: the percent fructan in the grain by weight, and the starch content of the grain by weight. For the first parameter, the percentage fructan of the cereal grain by weight is at least 3%, preferably at least 4%, at least 5%, at least 6%, at least 7%, at least 8%, at least 9% or at least 10% as shown herein For the second parameter, the starch content of the grain by weight, is at least 30%, preferably at least 35%, at least 36%, at least 37%, at least 38%, at least 39% or at least 40% as a percentage of the total grain weight. The invention includes each and every specific combination of these two parameters with respect to the grain, products obtained therefrom, methods of obtaining and using the grain, and uses of the grain and products therefrom. Reference herein to "high fructan" is used merely to indicate that the product is produced from the herein disclosed modified grain having an elevated level of fructan compared to an unmodified or control form of the grain.

In another embodiment, the method comprises: (i) obtaining or producing a cereal plant or grain or flour therefrom wherein wherein the cereal plant or grain is modified to comprise a reduced level of an endogenous polypeptide with starch synthase II (SSII) activity relative to an unmodified control; and (ii) processing the plant, grain or flour to produce the product. Various forms of this aspect of the invention are described in the Examples. Methods for reducing the level of an endogenous polypeptide with starch synthase II (SSII) activity in cereal plants relative to an unmodified or control plant are known in the art as described herein and in the common general knowledge. In particular embodiments, the grain is characterized by the same combination of two parameters as described in paragraph 0021.

In some embodiments, the methods further comprise: (iii) assessing the level or type of fructan in the cereal plant or grain or flour therefrom, or the product therefrom.

In several embodiments, the cereal grain is wholegrain which may be cracked, ground, polished, milled, kibbled, rolled or pearled grain. In some embodiments, the present invention extends to monocotyledonous cereal plants selected from the group consisting of barley, wheat, rice, maize, rye, oat and sorghum. In further embodiments, the plant is tetraploid wheat, maize, rye, rice, oat or sorghum, or hexaploid wheat or barley.

In a particular embodiment, the plant is a barley shrunken grain mutant designated M292 or M342 described in International Publication No. WO 02/37955.

As illustrated in the Examples, the fructan of the present invention in some embodiments comprises a degree of polymerization from about 3 to about 12.

In one application of the present invention, the product is a food or beverage product or a pharmaceutical composition. In a particular embodiment, the product is isolated fructan. non-limiting examples of food or beverage products include, grain, flour, breakfast cereal, biscuit, muffin, muesli bar, noodle, corn, a sweetening agent, a low calorie additive, a bulking agent, a dietary fibre, a texturizing agent, a preservative, a probiotic agent or the like or any combination of these.

In some further embodiments, the cereal plant or grain of the present invention is modified to comprise a reduced level of an endogenous polypeptide with starch synthase II (SSII) activity relative to an unmodified control. As known to those of skill in the art a wide range of methods are available for reducing the level of an endogenous polypeptide in a plant. In some embodiments, the plant comprises a mutation in an endogenous gene encoding a polypeptide with SSII activity wherein the mutation reduces the expression of the gene encoding SSII in the plant or leads to the expression of SSII with reduced level or activity. In other embodiments, the level of SSII activity is reduced by introducing into said plant a nucleic acid molecule which down-regulates the expression of a gene encoding SSII in the plant. In some embodiments, the nucleic acid molecule comprises a gene-silencing chimeric gene, an antisense, ribozyme, co-expression dsRNA molecule, or other exogenous nucleic acid molecule that down-regulates endogenous SSII expression. In preferred embodiments, the grain is characterized by the same combination of two parameters as described in paragraph 0021.

In another aspect the present invention provides a method of producing a cereal plant or grain therefrom which has increased levels of fructan compared to a control plant, wherein the method comprises: (i) introducing into said plant an agent which down-regulates the level or activity of endogenous starch synthase II (SSII) in the plant relative to a control plant, or a mutation in an endogenous gene encoding SSII in the plant. As described further herein in some embodiments, the agent comprises a nucleic acid molecule which down-regulates endogenous SSII gene expression. Illustrative nucleic acid molecules include a gene-silencing chimeric gene, an antisense, ribozyme, co-expression dsRNA molecule, or other exogenous nucleic acid molecule that down-regulates endogenous SSII expression.

In a further embodiment of this aspect of the invention the method comprises assessing the level, activity or type of fructan in the plant or grain therefrom. In some embodiments, the increased level of fructan is at least twice, preferably at least 3×, at least 4×, at least 5×, at least 6×, at least 7×, at least 8×, at least 9× or at least 10×, that of a control plant or the plant prior to the introduction of the agent or mutation.

In another aspect, the present specification provides an isolated or genetically modified cereal plant or grain or flour therefrom wherein the grain or flour comprises at least 3%, preferably at least 4% fructan as a percentage of the cereal grain or flour weight. Preferably, the plant or grain or flour is used, or is for use, in the production of a product to increase the level of fructan or non-starch carbohydrate in said product. In some embodiments, the percentage fructan of the cereal grain or flour by weight is at least 5%, at least 6%, at least 7%, at least 8%, at least 9% or at least 10% as shown herein. In preferred embodiments, the grain is characterized by the same combination of two parameters as described in paragraph 0021. As is readily apparent, the invention includes the flour, fructan and food products produced from each of these preferred embodiments of grain.

Accordingly, the present invention contemplates, cereal grain, flour or fructan produced from the plant or grain as described herein. In some embodiments, the cereal grain or flour comprises a starch content of at least 30%, preferably at least 35%, at least 36%, at least 37%, at least 38%, at least 39% or at least 40% as a percentage of the total grain weight.

In some embodiments, the cereal plant is not barley or hexaploid wheat.

In particular embodiments, the cereal grain or flour as described herein comprising a reduced level or activity of a polypeptide having SSII activity.

In some embodiments, the present invention provides fructan, grain or flour produced from the plant or grain or flour as described herein. The inventors contemplate, for example, the use of fructan isolated from the subject plant, grain or flour in a food as a sweetening agent, a low calorie additive, a bulking agent, a dietary fibre, a texturizing agent, a preservative, a probiotic agent or the like or any combination of these. In some embodiments, the inventors contemplate the use of a grain or flour or frunctan isolated from a plant, grain or flour as described herein in the production of a food product to increase the level of frunctan in said food product. In preferred embodiments, the grain is characterized by the same combination of two parameters as described in paragraph 0021.

In some embodiments, the food product comprises a food ingredient at a level of at least 10% on a dry weight basis, wherein the food ingredient is a cereal grain comprising at least 3%, preferably at least 4%, fructan on a weight basis or wholemeal or flour obtained therefrom wherein the wholemeal or flour comprises at least 3%, preferably at least 4% fructan on a weight basis. In preferred embodiments, the grain is characterized by the same combination of two parameters as described in paragraph 0021.

In yet another aspect, the present invention provides a method of identifying a variety of cereal grain which has increased levels of fructan comprising: (i) obtaining cereal grain which is altered in starch via synthesis or catabolism; (ii) determining the amount of fructan in the grain, (iii) comparing the level of fructan to that in wild-type grain which is not altered in starch via synthesis or catabolism, and (iv) if the fructan level is increased in the altered grain, selecting the grain. In some embodiments, the method further comprises mutagenesis or plant cell transformation prior to step (i).

In another embodiments, a method is provided for determining the amount of fructan in cereal grain, comprising the steps of (i) obtaining grain comprising at least 3%, preferably at least 4% fructan on a weight basis, processing the grain so as to extract the fructan, and measuring the amount of extracted fructan so as to determine the amount of fructan in the grain.

In a further embodiment, the present invention contemplates a method for preparing a food or beverage, comprising mixing a high-fructan product obtained by the herein disclosed methods with another food or beverage ingredient.

In another embodiment, the present invention provides a method for providing fructan to improve one or more indicators of health in a subject in need thereof, wherein the method comprises administering, to the subject, a composition comprising cereal grain or flour therefrom comprising at least 3%, preferably at least 4%, fructan on a weight basis or fructan obtained therefrom. In some embodiments, the grain, flour or fructan is in the form of a food product, a beverage or a pharmaceutical composition. In other embodiments, the one or more indicators of health is an increased number of beneficial intestinal bacteria, reduced number of aberrant crypt foci, increased mineral absorption, reduced level of insulin, reduced glycaemic index, reduced glycaemic load, reduced blood glucose, reduced blood pressure, reduced body weight, reduced blood cholesterol level, increased HDL cholesterol level, increased bone density, increased calcium levels, more frequent bowel movement, or improved blood serum cardiovascular profile. In preferred embodiments, the grain is characterized by the same combination of two parameters as described in paragraph 0021.

The present invention provides a method for ameliorating one or more symptoms of a condition associated with low levels of dietary fructan in a subject in need thereof, said method comprising administering orally to the subject grain comprising at least 3%, preferably at least 4%, fructan as a percentage of the cereal grain weight or a processed product comprising the fructan obtained therefrom for a time and under conditions sufficient to ameliorate one or more symptoms. The condition, in some embodiments, is selected from the group consisting of diabetes, obesity, heart disease, hypertension, constipation, osteoporesis and cancer. The method may comprise the step of determining that the subject may benefit from increased intake of dietary fructan. In preferred embodiments, the grain is characterized by the same combination of two parameters as described in paragraph 0021.

Any subject who could benefit from the present methods or compositions is encompassed. The term "subject" includes, without limitation, humans and non-human primates, livestock animals, companion animals, laboratory test animals, captive wild animals, reptiles and amphibians, fish, birds and any other organism. A subject, regardless of whether it is a human or non-human organism may be referred to as a patient, individual, subject, animal, host or recipient. In a particular embodiment the subject is a human.

The above summary is not and should not be seen in any way as an exhaustive recitation of all embodiments of the present invention.

DETAILED DESCRIPTION

Figure 1:
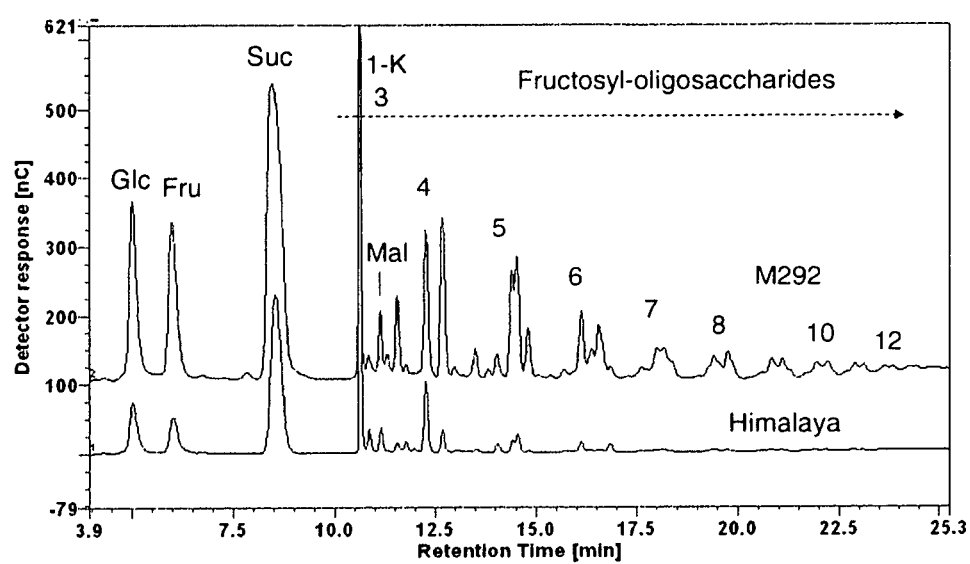
FIG. 1 is a graphical representation showing the soluble carbohydrate profile of mutant 'M292' and wild type 'Himalaya' mature barley grains. HPAE chromatographic elution profile of grain extracts indicating increased levels of hexose, sucrose, maltose and fructo-oligosaccharides in the mutant M292 compared to wild type Himalaya grain. Glc, glucose; Fru, fructose; Suc, sucrose; Mal, maltose; 1-K, 1-kestose; numerals indicate tentative degree of polymerization (DP) of fructo-oligosaccharides.

The present specification was based at least in part upon the discovery that cereal barley plants having reduced levels of synthesis of amylopectin through down regulation of starch synthase II gene expression also exhibit low levels of amylopectin, a relatively high proportion of amylose in the total starch of the grain, enhanced levels of sugars and surprisingly high levels of non-starch polysaccharide (NSP) and particularly fructan on a weight basis (see Table 1 and Table 3). Transcriptional profiles of plants comprising a loss of function mutation in SSII or SSII and exhibiting high fructan levels are shown in Table 2.

Accordingly, in one embodiment, the specification provides a method of producing a high-fructan product, wherein the method comprises: (i) obtaining or producing a cereal plant or grain or flour therefrom wherein the cereal grain or flour comprises at least 3%, preferably at least 4%, fructan as a percentage of the cereal grain or flour weight; (ii) processing the plant, grain or flour to produce the product, and optionally (iii) assessing the level or type of fructan in the cereal plant or grain or flour therefrom, or the product therefrom. It is believed that the presence of 3% or 4% fructan in the grain of cereal distinguishes the present invention from the prior art. However, illustrative levels of at least about 10% fructan are described and accordingly, the percentage fructan of the cereal grain or flour by weight in some embodiments, is at least 5%, at least 6%, at least 7%, at least 8%, at least 9% or at least 10%. If the product is isolated fructan, the product may comprise at least 50%, or at least 60% or at least 70% or preferably at least 80% fructan by weight.

In another embodiment, the method comprises: (i) obtaining or producing a cereal plant or grain or flour therefrom wherein wherein the cereal plant or grain is modified to comprise a reduced level of an endogenous polypeptide with starch synthase II (SSII) activity relative to an unmodified control; (ii) processing the plant, grain or flour to produce the product, and optionally (iii) assessing the level or type of fructan in the cereal plant or grain or flour therefrom, or the product therefrom.

It is unexpected that reduction in starch synthase activity which reduces the formation of amylopectin, also increases fructan production in the plant. Starch serves as the primary carbohydrate component in the diet of humans, in particular from cereals. Starch is the major storage carbohydrate in cereals, making up approximately 45-65% of the weight of the mature grain. However, cereal grains also contain non-starch polysaccharides such as β-glucans or low levels of fructans. In wild-type wheat grain, the level of fructan is only 0.6%-2.6% by weight.

Starch is composed only of glucosidic residues and is found as two types of molecules, amylose and amylopectin, which can be distinguished on the basis of molecular size or other properties. Amylose molecules are essentially linear polymers composed of α-1,4 linked glucosidic units, while amylopectin is a highly branched molecule with α-1,6 glucosidic bonds linking many linear chains of α-1,4 linked glucosidic units. Amylopectin is made of large molecules ranging in size between several tens of thousands to hundreds of thousands of glucose units with around 5 percent α-1,6 branches. Amylose on the other hand is composed of molecules ranging in size between several hundreds to several thousand glucosidic residues with less than one percent branches (for review see Buléon et al., *International Journal of Biological Macromolecules*, 23: 85-112, 1998). Wild-type cereal starches typically contain 20-30% amylose while the remainder is amylopectin.

The synthesis of starch in the endosperm of higher plants is carried out by a suite of enzymes that catalyse four key steps. Firstly, ADP-glucose pyrophosphorylase activates the monomer precursor of starch through the synthesis of ADP-glucose from G-1-P and ATP. Secondly, the activated glucosyl donor, ADP-glucose, is transferred to the non-reducing end of a pre-existing α1-4 linkage by starch synthases. Thirdly, starch branching enzymes introduce branch points through the cleavage of a region of α-1,4 linked glucan followed by transfer of the cleaved chain to an acceptor chain, forming a new α-1,6 linkage. Starch branching enzymes are the only enzymes that can introduce the α-1,6 linkages into α-polyglucans and therefore play an essential role in the formation of amylopectin. Finally, starch debranching enzymes remove some of the branch linkages although the mechanism through which they act is unresolved.

While it is clear that at least these four activities are required for normal starch granule synthesis in higher plants, multiple isoforms of each of the four activities are found in the endosperm of higher plants and specific roles have been proposed for individual isoforms on the basis of mutational analysis or through the modification of gene expression levels using transgenic approaches. In the cereal endosperm, four classes of starch synthase are found in the cereal endosperm, an isoform exclusively localised within the starch granule, granule-bound starch synthase (GBSS) which is essential for amylose synthesis, two forms that are partitioned between the granule and the soluble fraction (SSI, Li et al., *Plant Physiology*, 120: 1147-1155, 1999a, SSII, Li et al., *Theoretical and Applied Genetics*, 98: 1208-1216, 1999b) and a fourth form that is entirely located in the soluble fraction, SSIII (Cao et al., *Archives of Biochemistry and Biophysics*, 373: 135-146, 2000; Li et al., 1999b (supra); Li et al., *Plant Physiology*, 123: 613-624, 2000). Mutations in SSII and SSIII have been shown to alter amylopectin structure (Gao et al., *Plant Cell*, 10: 399-412, 1998; Craig et al., *Plant Cell* 10: 413-426, 1998). No mutations defining a role for SSI activity have been described.

Three forms of branching enzyme are expressed in the cereal endosperm, branching enzyme I (SBEI), branching enzyme IIa (SBEIIa) and branching enzyme IIb (SBEIIb) (Hedman and Boyer, *Biochemical Genetics*, 20: 483-492, 1982; Boyer and Preiss, *Carbohydrate Research*, 61: 321-334, 1978; Mizuno et al., *Journal of Biochemistry*, 112: 643-651, 1992; Sun et al., *The New Phytologist*, 137: 215-215, 1997). Alignment of SBE sequences has revealed a high degree of sequence similarity at both the nucleotide and amino acid levels and allows the grouping into the SBEI, SBEIIa and SBEIIb classes.

Two types of debranching enzymes are present in higher plants and are defined on the basis of their substrate specificities, isoamylase type debranching enzymes, and pullulanase type debranching enzymes (Myers et al., *Plant Physiology*, 122: 989-997, 2000). Sugary-1 mutations in maize and rice are associated with deficiency of both debranching enzymes (James et al., *Plant Cell*, 7: 417-429, 1995; Kubo et al., *Plant Physiology*, 121: 399-409, 1999) however the causal mutation maps to the same location as the isoamylase-type debranching enzyme gene.

A mutant form of barley, designated M292 or M342, has been shown to have an elevated amylose starch phenotype and a reduced amylopectin starch phenotype. This phenotype has suspected benefits for human health (Morell et al., *Plant J.* 34: 173-185, 2003; Topping et al., *Starch/Stärke* 55: 539-545, 2003; Bird et al., *J. Nutr.* 134: 831-835, 2004a; Bird et al. *Br. J. Nutr.* 92: 607-615, 2004b). It is caused by a mutation in the starch synthase IIa gene (SSIIa) located on chromosome 7H of barley, as described in international patent application PCT/AU01/01452 (Publication No. WO 02/37955) the disclosure of which is incorporated herein by reference.

The barley sex6 mutation resulted from the presence of a stop codon within the starch synthase IIa (SSIIa) gene. The stop codon lead to premature termination of translation of the transcript. The SSIIa protein was not detectable in the endosperm of this mutant (Morell et al. 2003 (supra)). The loss of SSIIa activity lead to an 80% decrease in amylopectin synthesis, and the remaining amylopectin polymers in general have altered chain length distribution, and consequently an altered amylose:amylopectin ratio so that the starch of the grain contained about 70% amylose.

SSII mutants of wheat have also been produced (Yamamori et al., *Theor. Appl. Genet.* 101: 21-29, 2000) although the amylose level was not as high as in the barley mutant, reaching about 38% in the wheat. In contrast, down-regulation of the genes encoding SBEIIa in wheat resulted in a high amylose phenotype, with about 80% amylose in the starch of the grain (Regina et al., *Proc. Natl. Acad. Sci. U.S.A.* 103: 3546-3551, 2006).

In some embodiments, the present invention provides for improvements in cereal plant utility by increasing the level of fructan in grain. The modification may be limited to grain or alternatively, the modification may be thoughout the plant in various of its tissues and parts. As used herein, "modifying" or "modified" means a change in the plant or grain, which may be an increase or decrease in amount, activity, rate of production, rate of inactivation, rate of breakdown, delay of onset, earlier onset, addition or removal of material, mutation, or any combination of these, so long as there is a reduced level or activity of starch synthase II. The terms include either an increase or decrease in the functional level of a gene or protein of interest. "Functional level" should be understood to refer to the level of active protein. The functional level is a combination of the actual level of protein present in the host cell and the specific activity of the protein. Accordingly, the functional level may e.g. be modified by increasing or decreasing the actual protein concentration in the host cell, which may readily be achieved by altering expression of a gene encoding the protein. The functional level may also be modified by modulating the specific activity of the protein. Such increase or decrease of the specific activity may be achieved by expressing a variant protein with higher or lower specific activity or by replacing the endogenous gene encoding the relevant protein with an allele encoding such a variant. Increase or decrease of the specific activity may also be achieved by expression of an effector molecule. In certain embodiments, the expression level of an appropriate coding sequence or activity or amount of an enzyme is chosen such that it is at least about 10%, at least 20%, at least 30%, at least 40%, at least 50%, at least 60%, at least 80% or even at least about 100%, at least 200%, at least 500%, or at least 1000% higher, or at least about 10%, at least 20%, at least 30%, at least 40%, at least 50%, at least 60%, at least 70%, at least 80%, at least 90%, at least 92%, at least 94%, at least 96%, at least 97%, at least 98% or at least 99% lower than a reference expression level, or reduced to an undetectable level.

Another way of distinguishing the required reduction in SSII level or activity is by quantifying the increase level or the increase in various forms of fuctan in a modified plant or grain therefrom. As used herein, the terms "modifying", "altering", "increasing", "increased", "reducing", "reduced", "inhibited", "mutant" or the like are considered relative terms, i.e. in comparison with the wild-type or unaltered or control state. In some embodiments, a wild-type plant is an appropriate "control plant" however in many situations the control plant must be determined by the skilled addressee using their ordinary skill in the art. The "level of a protein" refers to the amount of a particular protein, for example SSII, which may be measured by any means known in the art such as, for example, Western blot analysis or other immunological means. The "level of an enzyme activity" refers to the amount of a particular enzyme measured in an enzyme assay.

It would be appreciated that the level of activity of an enzyme might be altered in a mutant if a more or less active protein is produced, but not the expression level (amount) of the protein itself. Conversely, the amount of protein might be altered but the activity (per unit protein) remain the same. Reductions in both amount and activity are also possible such as, for example, when the expression of a gene encoding the enzyme is reduced transcriptionally or post-transcriptionally. In certain embodiments, the reduction in the level of protein or activity of SSII is by at least 40% or by at least 60% compared to the level of protein or activity in the grain of unmodified cereal, for example wheat or barley, or by at least 75%, at least 90% or at least 95%. The reduction in the level of the protein or enzyme activity or gene expression may occur at any stage in the development of the leaf, seed or grain, particularly during the daytime when photosynthesis is occurring, or during the grain filling stage while starch is being synthesized in the developing endosperm, or at all stages of grain development through to maturity. The term "wild-type" as used herein has its normal meaning in the field of genetics and includes plant, preferably cereal, cultivars or genotypes which are not modified as taught herein. Some preferred "wild-type" cereal plant varieties are described herein.

The modified phenotype may be achieved by partial or full inhibition of the expression of an SSII gene. Techniques well known in the art such as SDS-PAGE and immunoblotting are carried out on hydrolysed and unhydrolysed grains and fractions thereof to identify the plants or grain where modifications have occurred to starch forming enzymes, carbohydrate related genes, defense related genes, stress protein related genes or genes identified as differentially expressed in the subject modified plants or grain thereform (such as those listed in Table 2). These methods include analysis of plants by methods described herein or further by methods such as such as microarray analysis, electrophoresis, chromatography (including paper chromatography, thin layer chromatography, gas chromatography, gas-liquid chromatography and high-performance liquid chromatography) techniques. Separated components are typically identified by comparison of separation profiles with standards of known identity, or by analytical techniques such as mass spectrometry and nuclear magnetic resonance spectroscopy. For example, reference may be made to Example 9, Robinson, *The Organic Constituents of Higher Plants*, Cordus Press, North Amherst, USA, 1980; Adams et al., *Anal. Biochem.*, 266: 77-84, 1999; Veronese et al., *Enz. Microbial Tech.*, 24: 263-269, 1999; Hendrix et al., *J. Insect Physiol.*, 47: 423-432, 2001; Thompson et al., *Carbohydrate Res.*, 331: 149-161, 2001; and references cited therein. Carbohydrates can be assayed using standard protocols known to persons skilled in the art.

Alteration in SSII activities may be achieved by the introduction of one or more genetic variations into the cereal plant. That is, the genetic variations lead, directly or indirectly, to the alteration in enzyme activity in the plant part during growth or development and consequently to the enzyme and fructan modifications described herein. The genetic variation may be a heterologous polynucleotide which is introduced into the plant or a progenitor cell, for example by transformation or mutagenesis. The genetic variation may subsequently be introduced into different genetic backgrounds by crossing, as known in the art of plant breeding. In some embodiments, the level or functional activity of SSII is down regulated to a level less than about 80%, less than 70%, less than 60%, less than 50%, less than 40%, less than 30%, less than 20% or less than 15%, and suitably less than about 10%, less than 9%, less than 8%, less than 7%, less than 6%, less than 5%, less than 4%, less than 3%, less than 2% or less than 1% relative to a corresponding control plant to achieve elevated levels of fructan. In a preferred embodiment, elevated levels are at least twice that of controls. Preferably, in this embodiment, this reduction results in a substantial enhancement of non-starch polysaccharide such as fructan levels which is generally at least about 50% or 55% and more especially at least about 60%, at least 65%, at least 70%, at least 75%, at least 80%, at least 85%, at least 90%, at least 95% or greater increase in fructan level relative to a corresponding control plant grown under the same environmental conditions. The amount of reduced SSII level or activity required may depend upon other factors such as the plant species or strain environmental factors. However, it is considered that any optimisation, which may be required in such an event is achievable using routine methods including those described herein.

Reduced SSII levels may be accomplished in tissues throughout the plant, for example using a constitutive promoter to drive expression of a heterologous polynucleotide that down regulates SSII. Alternatively, it may be accomplished in source tissues (leaves), in transport tissues or in sink tissues (endosperm) using a tissue-specific or developmentally regulated promoter. "Sink cell" and "sink tissue" as used herein, refer to cells, tissues or organs which comprise a net inflow of organic carbon that has entered the cells in a form other than fixation of carbon dioxide ie. as sugars or other carbohydrates. In plants, sink tissues include all non-photosynthetic tissues, as well as photosynthetic tissues with a net inflow of organic carbon fixed by other photosynthetic cells or otherwise obtained from the surrounding medium or environment by means other than direct fixation of carbon dioxide.

In certain embodiments, the level fructan in grain is increased at least about 10%, at least 20%, at least 30%, at least 40%, at least 50%, at least 60%, at least 70%, at least 80% or at least 90%, or even at least about 100%, at least 200%, at least 300%, at least 400%, at least 500%, at least 600%, at least 700%, at least 800%, at least 900% or at least 1000% higher relative to controls.

Genes

In some embodiments, the present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

The "starch synthase II gene" "SSII" or the like as used herein refers to a nucleotide sequence encoding starch synthase II (SSII) in cereals such as barley or wheat, which can readily be distinguished from other starch synthases or other proteins by those skilled in the art. Wheat SSII genes include the naturally occurring variants existing in wheat, including those encoded by the A, B and D genomes of breadwheat, as well as non-naturally occurring variants which may be produced by those skilled in the art of gene modification. In a preferred embodiment, a barley SSII gene refers to a nucleic acid molecule, which may be present in or isolated from barley or derived therefrom, comprising nucleotides having a sequence having at least 80% identity to the cDNA sequence shown in SEQ ID NO: 1. In another preferred embodiment, a wheat SSII gene refers to a nucleic acid molecule, which may be present in or isolated from wheat or derived therefrom, comprising nucleotides having a sequence having at least 80% identity to the cDNA shown in SEQ ID NO: 3, 5, 7, 9 or 18. In a preferred embodiment, the SSII gene is an SSIIa gene, or the SSII protein is an SSIIa protein, each of which may be applied to any or all of the aspects of the invention disclosed herein.

A genomic form or clone of a gene containing the transcribed region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or for integration into the host genome.

As used herein, a "chimeric gene" refers to any gene that is not a native gene in its native location. Typically a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule" refers to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. These include gene sequences found in that cell so long as the introduced gene contains some modification (e.g. a mutation, the presence of a selectable marker gene, etc.) relative to the naturally-occurring gene. Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Polynucleotides

The present invention including the description, tables and sequence listing, refers to various polynucleotides. As used herein, a "polynucleotide" or "nucleic acid" or "nucleic acid molecule" means a polymer of nucleotides, which may be DNA or RNA or a combination thereof, and includes mRNA, cRNA, cDNA, tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid".

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state. For example, an "isolated polynucleotide" includes a polynucleotide which has been purified or separated from the sequences which flank it in a naturally occurring state, e.g., a DNA fragment which has been removed from the sequences which are normally adjacent to the fragment. Preferably, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence.

The present invention refers to use of oligonucleotides. As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Polynucleotides used as a probe are typically conjugated with a detectable label such as a radioisotope, hapten, an enzyme, biotin, a fluorescent molecule or a chemiluminescent molecule. Oligonucleotides of the invention are useful in methods of detecting an allele of an SSII or other gene linked to a trait of interest, for example modified starch or fructan levels. Such methods, for example, employ nucleic acid hybridization and in many instances include oligonucleotide primer extension by a suitable polymerase (as used in PCR).

A variant of an oligonucleotide of the invention includes molecules of varying sizes of, and/or are capable of hybridising, for example, to the cereal genome close to that of, the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without negatively influencing the ability of the oligonucleotide to hybridise to the target region. In addition, variants may readily be designed which hybridise close to, for example to within 50 nucleotides, the region of the plant genome where the specific oligonucleotides defined herein hybridise. Probes, oligonucleotides and the like are based upon the herein described sequences or corrected versions thereof or variants thereof or functional homologs from other cereal plants.

The terms "polynucleotide variant" and "variant" and the like refer to polynucleotides or their complementary forms displaying substantial sequence identity with a reference polynucleotide sequence. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridising agents. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

By "corresponds to" or "corresponding to" is meant a polynucleotide (a) having a nucleotide sequence that is substantially identical or complementary to all or most of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a minimum number of nucleotides or amino acid residues or over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The % identity of a polynucleotide can be determined by GAP (Needleman and Wunsch, *J. Mol. Biol.* 48: 443-453, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides, or at least 400, at least 500 or at least 600 nucleotides in each case. Reference also may be made to the BLAST family of programs as for example disclosed by Altschul et al., *Nucleic Acids Res.* 25: 3389, 1997. A detailed discussion of sequence analysis can be found in Unit 19.3 of Ausubel et al., "*Current Protocols in Molecular Biology*", John Wiley & Sons Inc, 1994-1998, Chapter 15.

Nucleotide or amino acid sequences are indicated as "essentially similar" when such sequences have a sequence identity of at least 80%, particularly at least 85%, quite particularly at least 90%, especially at least 95%, more especially are identical. It is clear that when RNA sequences are described as essentially similar to, correspond to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Preferably, a polynucleotide of the invention which encodes a polypeptide with SSII activity is greater than 800, preferably greater than 900, and even more preferably greater than 1,000 or 2000 nucleotides in length.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

The present invention refers to the stringency of hybridization conditions to define the extent of complementarity of two polynucleotides. "Stringency" as used herein, refers to the temperature and ionic strength conditions, and presence or absence of certain organic solvents, during hybridization and washing. The higher the stringency, the higher will be the degree of complementarity between a target nucleotide sequence and the labelled polynucleotide sequence (probe). "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Ausubel et al., (eds.), *Current Protocols in Molecular Biology*, John Wiley & Sons, NY, 6.3.1-6.3.6., 1989. Aqueous and nonaqueous methods are described in that reference and either can be used. Specific hybridization conditions referred to herein are as follows: 1) low stringency hybridization conditions are for hybridization in 6× sodium chloride/sodium citrate (SSC) at 45° C., followed by two washes in 0.2×SSC, 0.1% SDS at 50-55° C.; 2) medium stringency hybridization conditions are for hybridization in 6×SSC at about 45° C., followed by one or more washes in 0.2×SSC, 0.1% SDS at 60° C.; 3) high stringency hybridization conditions are for hybridization in 6×SSC at 45° C., followed by one or more washes in 0.2×SSC, 0.1% SDS at 65° C.; and 4) very high stringency hybridization conditions are for hybridization in 0.5 M sodium phosphate buffer, 7% SDS at 65° C., followed by one or more washes at 0.2×SSC, 1% SDS at 65° C.

Polypeptides

The terms "polypeptide" and "protein" are generally used interchangeably. The terms "proteins" and "polypeptides" as used herein also include variants, mutants, modifications, analogs and/or derivatives of the polypeptides of the invention as described herein. As used herein, "substantially purified polypeptide" refers to a polypeptide that has been separated from the lipids, nucleic acids, other peptides and other molecules with which it is associated in its native state. Preferably, the substantially purified polypeptide is at least 90% free from other components with which it is naturally associated. By "recombinant polypeptide" is meant a polypeptide made using recombinant techniques, i.e., through the expression of a recombinant polynucleotide in a cell, preferably a plant cell and more preferably a cereal plant cell.

Illustrative polypeptides having SSII activity are set out in the sequence listing and described in Table 7. Accordingly, the present invention proposes without limitation the modification of SSII polypeptides having the amino acid sequences set forth in SEQ ID NO: 2, 4, 6, 8, 11, 13, 17, 19, 21, and 23 and naturally occurring variants, corrected versions thereof and variants as described herein such as variants having about 80% sequence identity.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

The % identity of a polypeptide relative to another polypeptide can be determined by GAP (Needleman and Wunsch, 1970 (supra)) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids.

As used herein a "biologically active" fragment of a polypeptide is a portion of a polypeptide of the invention, less than full length, which maintains a defined activity of the full-length polypeptide. In a particularly preferred embodiment, the biologically active fragment is able to synthesize starch to produce amylose chains having a DP of at least 15. Biologically active fragments can be any size as long as they maintain the defined activity, but are preferably at least 200 or at least 250 amino acid residues long.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics.

Mutant (altered) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama, *Trends Biotechnol.* 16: 76-82, 1998. These DNA shuffling techniques may include genes related to those of the present invention, such as SSII genes from plant species other than wheat or barley, and/or include different genes from the same plant encoding similar proteins, such as the wheat or barley starch synthase I or III genes. Products derived from mutated/altered DNA can readily be screened using techniques described herein to determine if they possess, for example, starch synthase activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 9 under the heading of "exemplary substitutions".

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In certain embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, including a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of the plant, such as, for example, endosperm, embryo, leaves, fruit, tubers or root. In one embodiment, a promoter is expressed in all photosynthetic tissue, which may correspond to all aerial parts of the plant, for example a promoter that is involved in expressing a gene required for photosynthesis such as rubisco small subunit promoters. The term may also refer to expression at specific developmental stages in an organ, such as in early or late embryogenesis or different stages of maturity; or to expression that is inducible by certain environmental conditions or treatments. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the endosperm, cytosol, vacuole, or apoplastic space may be achieved by the inclusion in the structure of the gene product of appropriate signals for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in a plant. Typically, the promoter is expressed at a level 10-fold higher in the specific tissue or organ than in other tissues or organs. An illustrative tissue specific promoter is the promoter for high molecular weight (HMW) glutenin gene, Bx17 which is expressed preferentially in the developing endosperm of cereal plants. Further endosperm specific promoters include the high molecular weight glutenin promoter, the wheat SSI promoter, and the wheat BEII promoter.

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters; promoters from plants, such as ubiquitin promoters such as the Ubi promoter from the maize ubi-1 gene, Christensen et al., *Transgen. Res.,* 5: 213-218, 1996 (see, e.g., U.S. Pat. No. 4,962,028) or actin promoters; tissue specific promoters (see, e.g., U.S. Pat. No. 5,459,252 to Conkling et al.; WO 91/13992 to Advanced Technologies); promoters from viruses (including host specific viruses), or partially or wholly synthetic promoters. Numerous promoters that are functional in mono- and dicotyledonous plants are well known in the art (see, for example, Greve, *J. Mol. Appl. Genet.,* 1: 499-511, 1983; Salomon et al., *EMBO* 1, 3: 141-146, 1984; Garfinkel et al., *Cell,* 27: 143-153, 1983; Barker et al., *Plant Mol. Biol.,* 2: 235-350, 1983; including various promoters isolated from plants and viruses such as the cauliflower mosaic virus promoter (CaMV 35S, 19S). Many tissue specific promoter regions are known. Other transcriptional initiation regions which preferentially provide for transcription in certain tissues or under certain growth conditions, include those from genes encoding napin, seed ACP, zein, or other seed storage proteins. Fruit specific promoters are also known, one such promoter is the E8 promoter, described by Deikman et al., *EMBO J.,* 2: 3315-3320, 1998 and DellaPenna et al., *Plant Cell,* 1: 53-63, 1989. Non-limiting methods for assessing promoter activity are disclosed by Medberry et al., *Plant Cell,* 4: 185-192, 1992; Medberry et al., *Plant J.* 3: 619-626, 1993, Sambrook et al., *Molecular Cloning: A Laboratory Manual* (2nd ed.). Cold Spring Harbour Laboratory, Cold Spring Harbour, N Y, 1989, and McPherson et al. (U.S. Pat. No. 5,164,316).

Alternatively or additionally, the promoter may be an inducible promoter or a developmentally regulated promoter which is capable of driving expression of the introduced polynucleotide at an appropriate developmental stage of the plant. Other cis-acting sequences which may be employed include transcriptional and/or translational enhancers. Enhancer regions are well known to persons skilled in the art, and can include an ATG translational initiation codon and adjacent sequences. The initiation codon must be in phase with the reading frame of the coding sequence relating to the foreign or exogenous polynucleotide to ensure translation of the entire sequence. The translation control signals and initiation codons can be of a variety of origins, both natural and synthetic. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention typically comprises a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal is characterized by effecting the addition of polyadenylic acid tracts to the 3' end of the mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from the nopaline synthase (nos) gene of *Agrobacterium tumefaciens* (Bevan et al., *Nucl. Acid Res.*, 11: 369, 1983) and the terminator for the T7 transcript from the octopine synthase gene of *Agrobacterium tumefaciens*. Alternatively, suitable 3' non-translated sequences may be derived from plant genes such as the 3' end of the protease inhibitor I or II genes from potato or tomato, the soybean storage protein genes and the small subunit of the ribulose-1,5-bisphosphate carboxylase (ssRUBISCO) gene, although other 3' elements known to those of skill in the art can also be employed. Alternatively, 3' non-translated regulatory sequences can be obtained de novo as, for example, described by An, *Methods in Enzymology,* 153: 292, 1987, which is incorporated herein by reference.

As the DNA sequence inserted between the transcription initiation site and the start of the coding sequence, i.e., the untranslated 5' leader sequence (5'UTR), can influence gene expression, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi, *Nucl. Acid Res.* 15: 6643, 1987.

Additionally, targeting sequences may be employed to target the enzyme encoded by the foreign or exogenous polynucleotide to an intracellular compartment, for example to the chloroplast, within plant cells or to the extracellular environment. For example, a nucleic acid sequence encoding a transit or signal peptide sequence may be operably linked to a sequence that encodes a chosen enzyme of the subject invention such that, when translated, the transit or signal peptide can transport the enzyme to a particular intracellular or extracellular destination, and can then be optionally post-translationally removed. Transit or signal peptides act by facilitating the transport of proteins through intracellular membranes, e.g., endoplasmic reticulum, vacuole, vesicle, plastid, mitochondrial and plasmalemma membranes. For example, the targeting sequence can direct a desired protein to a particular organelle such as a vacuole or a plastid (e.g., a chloroplast), rather than to the cytosol. Thus, the nucleic acid construct of the invention can further comprise a plastid transit peptide-encoding nucleic acid sequence operably linked between a promoter region and the foreign or exogenous polynucleotide.

Vectors

The present invention includes use of vectors for manipulation or transfer of genetic constructs. By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, or pBS-derived vectors. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, kanamycin, erythromycin, chloramphenicol or tetracycline resistance. Exemplary selectable markers for selection of plant transformants include, but are not limited to, a hyg gene which encodes hygromycin B resistance; a neomycin phosphotransferase (npt) gene conferring resistance to kanamycin, paromomycin, G418 and the like as, for example, described by Potrykus et al., *Mol. Gen. Genet.* 199: 183, 1985; a glutathione-S-transferase gene from rat liver conferring resistance to glutathione derived herbicides as, for example, described in EP-A 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP-A 275957, a gene encoding a 5-enolshikimate-3-phosphate synthase (EPSPS) conferring tolerance to N-phosphonomethylglycine as, for example, described by Hinchee et al., *Biotech.* 6: 915, 1988, a bar gene conferring resistance against bialaphos as, for example, described in WO 91/02071; a nitrilase gene such as bxn from *Klebsiella ozaenae* which confers resistance to bromoxynil (Stalker et al., *Science,* 242: 419, 1988); a dihydrofolate reductase (DHFR) gene conferring resistance to methotrexate (Thillet et al., *J. Biol. Chem.* 263: 12500, 1988); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., *Biochem. Biophys. Res. Comm.* 126: 1259-68, 1985), which may be employed in calcium-sensitive bioluminescence detection; a green fluorescent protein gene (Niedz et al., *Plant Cell Reports,* 14: 403, 1995); a luciferase (luc) gene (Ow et al., *Science,* 234: 856, 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Methods of Modifying Gene Expression

The level of a protein, for example an enzyme involved in starch synthesis in developing endosperm of a cereal plant, may be modulated by increasing the level of expression of a nucleotide sequence that codes for the protein in a plant cell, or decreasing the level of expression of a gene encoding the protein in the plant, leading to altered fructan accumulation in grain. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial increase in fructan levels. This may be detected by simple testing of grain from the transformants. Alternatively, a population of mutagenized grain or a population of plants from a breeding program may be screened for individual lines with altered fructan accumulation.

Reducing gene expression may be achieved through introduction and transcription of a "gene-silencing chimeric gene" introduced into the plant cell. The gene-silencing chimeric gene may be introduced stably into the plant cell's genome, preferably nuclear genome, or it may be introduced transiently, for example on a viral vector. As used herein "gene-silencing effect" refers to the reduction of expression of a target nucleic acid in a a plant cell, which can be achieved by introduction of a silencing RNA. Such reduction may be the result of reduction of transcription, including via methylation of chromatin remodeling, or post-transcriptional modification of the RNA molecules, including via RNA degradation, or both. Gene-silencing includes an abolishing of the expression of the target nucleic acid or gene and a partial effect in either extent or duration. It is sufficient that the level of expression of the target nucleic acid in the presence of the silencing RNA is lower that in the absence thereof. The level of expression may be reduced by at least about 40%, or at least about 50%, or at least about 60%, or at least about 70%, or at least about 80%, or at least about 90%, or at least about 95%, or at least about 99%. The target nucleic acid may be a gene involved in starch synthesis or metabolism, for example starch degradation, but may also include any other endogenous genes, transgenes or exogenous genes such as viral genes which may not be present in the plant cell at the time of introduction of the transgene.

Antisense RNA Molecules

Antisense techniques may be used to reduce gene expression according to the invention. The term "antisense RNA" shall be taken to mean an RNA molecule that is complementary to at least a portion of a specific mRNA molecule and capable of reducing expression of the gene encoding the mRNA. Such reduction typically occurs in a sequence-dependent manner and is thought to occur by interfering with a post-transcriptional event such as mRNA transport from nucleus to cytoplasm, mRNA stability or inhibition of translation. The use of antisense methods is well known in the art (see for example, Hartmann and Endres, *Manual of Antisense Methodology,* Kluwer, 1999). The use of antisense techniques in plants has been reviewed by Bourque, *Plant Sci.* 105: 125-149, 1995 and Senior, *Biotech. Genet. Engin. Revs.* 15: 79-119, 1998. Bourque, 1995 (supra) lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior, 1998 (supra) states that antisense methods are now a very well established technique for manipulating gene expression.

As used herein, the term "an antisense polynucleotide which hybridises under physiological conditions" means that the polynucleotide (which is fully or partially single stranded) is at least capable of forming a double stranded polynucleotide with an RNA product of the gene to be inhibited, typically the mRNA encoding a protein such as those provided herein, under normal conditions in a cell. Antisense molecules may include sequences that correspond to the structural genes or for sequences that effect control over the gene expression or splicing event. For example, the antisense sequence may correspond to the coding region of the targeted gene, or the 5'-untranslated region (UTR) or the 3'-UTR or combination of these. It may be complementary in part to intron sequences, which may be spliced out during or after transcription, but is preferably complementary only to exon sequences of the target gene. In view of the generally greater divergence of the UTRs, targeting these regions provides greater specificity of gene inhibition.

The length of the antisense sequence should be at least 19 contiguous nucleotides, preferably at least 25 or 30 or 50 nucleotides, and more preferably at least 100, 200, 500 or 1000 nucleotides, to a maximum of the full length of the gene to be inhibited. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Genetic constructs to express an antisense RNA may be readily made by joining a promoter sequence to a region of the target gene in an "antisense" orientation, which as used herein refers to the reverse orientation relative to the orientation of transcription and translation (if it occurs) of the sequence in the target gene in the plant cell. Accordingly, also provided by this invention is a nucleic acid molecule such as a chimeric DNA coding for an antisense RNA of the invention, including cells, tissues, organs, plants, grain and the like comprising the nucleic acid molecule.

Ribozymes

The term "ribozyme" as used herein refers to an RNA molecule which specifically recognizes a distinct substrate RNA and catalyzes its cleavage. Typically, the ribozyme contains a region of nucleotides which are complementary to a region of the target RNA, enabling the ribozyme to specifically hybridize to the target RNA under physiological conditions, for example in the cell in which the ribozyme acts, and an enzymatic region referred to herein as the "catalytic domain". The types of ribozymes that are particularly useful in this invention are the hammerhead ribozyme (Haseloff and Gerlach, *Nature* 334: 585-591, 1988; Perriman et al., *Gene,* 113: 157-163, 1992) and the hairpin ribozyme (Shippy et al., *Mol. Biotech.* 12: 117-129, 1999). DNA encoding the ribozymes can be synthesized using methods well known in the art and may be incorporated into a genetic construct or expression vector for expression in the cell of interest. Accordingly, also provided by this invention is a nucleic acid molecule such as a chimeric DNA coding for a ribozyme of the invention, including cells, tissues, organs, plants, grain and the like comprising the nucleic acid molecule. Typically, the DNA encoding the ribozyme is inserted into an expression cassette under control of a promoter and a transcription termination signal that function in the cell. Specific ribozyme cleavage sites within any potential RNA target may be identified by scanning the target molecule for ribozyme cleavage sites which include the trinucleotide sequences GUA, GUU and GUC. Once identified, short RNA sequences of between about 5 and 20 ribonucleotides corresponding to the region of the target gene 5' and 3' of the cleavage site may be evaluated for predicted structural features such as secondary structure that may render the oligonucleotide sequence less suitable. When employed, ribozymes may be selected from the group consisting of hammerhead ribozymes, hairpin ribozymes, axehead ribozymes, newt satellite ribozymes, Tetrahymena ribozymes and RNAse P ribozymes, and are designed according to methods known in the art based on the sequence of the target gene (for instance, see U.S. Pat. No. 5,741,679). The suitability of candidate targets may also be evaluated by testing their accessibility to hybridization with complementary oligonucleotides, using ribonuclease protection assays.

As with antisense polynucleotides described herein, ribozymes of the invention should be capable of hybridizing to a target nucleic acid molecule (for example an mRNA encoding a polypeptide provided as SEQ ID NO:2, SEQ ID NO:4) under "physiological conditions", namely those conditions within a cell, especially conditions in a plant cell such as a wheat or barley cell.

RNA Interference/Duplex RNA

As used herein, "artificially introduced dsRNA molecule" refers to the introduction of dsRNA molecule, which may e.g. occur endogenously by transcription from a chimeric gene encoding such dsRNA molecule, however does not refer to the conversion of a single stranded RNA molecule into a dsRNA inside the eukaryotic cell or plant cell. RNA interference (RNAi) is particularly useful for specifically reducing the expression of a gene or inhibiting the production of a particular protein. Although not wishing to be limited by theory, Waterhouse et al., *Proc. Natl. Acad. Sci. U.S.A.* 95: 13959-13964, 1998 have provided a model for the mechanism by which dsRNA can be used to reduce protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are transcribed to produce a hairpin RNA in which the sense and anti-sense sequences hybridize to form the dsRNA region with an intervening sequence or spacer region forming a loop structure, so the hairpin RNA comprises a stem-loop structure. The design and production of suitable dsRNA molecules for the present invention is well within the capacity of a person skilled in the art, particularly considering Waterhouse et al., 1998 (supra), Smith et al., *Nature,* 407: 319-320, 2000, WO 99/53050, WO 99/49029, and WO 01/34815. Accordingly, also provided by this invention is a nucleic acid molecule such as a chimeric DNA coding for a duplex RNA such as a hairpin RNA of the invention, including cells, tissues, organs, plants, grain and the like comprising the nucleic acid molecule.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing (Smith et al., 2000 (supra)). The double-stranded region may comprise one or two RNA molecules, transcribed from either one DNA region or two. The dsRNA may be classified as long hpRNA, having long, sense and antisense regions which can be largely complementary, but need not be entirely complementary (typically forming a basepaired region larger than about 100 bp, preferably ranging between 200-1000 bp). hpRNA can also be smaller with the double-stranded portion ranging in size from about 30 to about 50 bp, or from 30 to about 100 bp (see WO 04/073390, herein incorporated by reference). The presence of the double stranded RNA region is thought to trigger a response from an endogenous plant system that processes the double stranded RNA to oligonucleotides of 21-24 nucleotides long, and also uses these oligonucleotides for sequence-specific cleavage of the homologous RNA transcript from the target plant gene, efficiently reducing or eliminating the activity of the target gene.

The length of the sense and antisense sequences that hybridise should each be at least 19 contiguous nucleotides, preferably at least 27 or 30 or 50 nucleotides, and more preferably at least 100, 200, or 500 nucleotides, up to the full-length sequence corresponding to the entire gene transcript. The lengths are most preferably 100-2000 nucleotides. The degree of identity of the sense and antisense sequences to the targeted transcript should be at least 85%, preferably at least 90% and more preferably 95-100%. The longer the sequence, the less stringent the requirement is for overall sequence identity. The RNA molecule may of course comprise unrelated sequences which may function to stabilize the molecule. The RNA molecule may be a hybrid between different sequences targeting different target RNAs, allowing reduction in expression of more than one target gene, or it may be one sequence which corresponds to a family of related target genes such as a multigene family. The sequences used in the dsRNA preferably correspond to exon sequences of the target gene and may correspond to 5' and/or 3' untranslated sequences or protein coding sequences or any combination thereof.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors. Typically, the RNA molecule is expressed under the control of a RNA polymerase II or RNA polymerase III promoter. Examples of the latter include tRNA or snRNA promoters.

Other silencing RNA may be "unpolyadenylated RNA" comprising at least 20 consecutive nucleotides having at least 95% sequence identity to the complement of a nucleotide sequence of an RNA transcript of the target gene, such as described in WO 01/12824 or U.S. Pat. No. 6,423,885 (both documents herein incorporated by reference). Yet another type of silencing RNA is an RNA molecule as described in WO 03/076619 (herein incorporated by reference) comprising at least 20 consecutive nucleotides having at least 95% sequence identity to the sequence of the target nucleic acid or the complement thereof, and further comprising a largely-double stranded region as described in WO 03/076619.

MicroRNA regulation is a specialized branch of the RNA silencing pathway that evolved towards gene regulation, diverging from conventional RNAi/PTGS. MicroRNAs are a specific class of small RNAs that are encoded in gene-like elements organized in a characteristic partial inverted repeat. When transcribed, microRNA genes give rise to partially basepaired stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, *Funct Integr Genomics*, 5: 129-135, 2005; Pasquinelli et al., *Curr Opin Genet Develop* 15: 200-205, 2005; Almeida and Allshire, *Trends Cell Biol.* 15: 251-258, 2005, herein incorporated by reference).

Cosuppression

Another molecular biological approach that may be used for specifically reducing gene expression is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the "sense orientation" with respect to a promoter for its expression, which as used herein refers to the same orientation as transcription and translation (if it occurs) of the sequence relative to the sequence in the target gene. The size of the sense fragment, its correspondence to target gene regions, and its degree of homology to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches. The antisense, co-suppression or double stranded RNA molecules may also comprise a largely double-stranded RNA region, preferably comprising a nuclear localization signal, as described in WO 03/076619.

Any of these technologies for reducing gene expression can be used to coordinately reduce the activity of multiple genes. For example, one RNA molecule can be targeted against a family of related genes by targeting a region of the genes which is in common. Alternatively, unrelated genes may be targeted by including multiple regions in one RNA molecule, each region targeting a different gene. This can readily be done by fusing the multiple regions under the control of a single promoter.

Methods of Introducing Nucleic Acids into Plant Cells/Transformation

A number of techniques are available for the introduction of nucleic acid molecules into a plant host cell, well known to workers in the art. The term "transformation" means alteration of the genotype of an organism, for example a bacterium or a plant, by the introduction of a foreign or exogenous nucleic acid. By "transformant" is meant an organism so altered. As used herein the term "transgenic" refers to a genetically modified plant in which the endogenous genome is supplemented or modified by the integration, or stable maintenance in a replicable non-integrated form, of an introduced foreign or exogenous gene or sequence. By "transgene" is meant a foreign or exogenous gene or sequence that is introduced into the genome of a plant. The nucleic acid molecule may be stably integrated into the genome of the plant, or it may be replicated as an extrachromosomal element. By "genome" is meant the total inherited genetic complement of the cell, plant or plant part, and includes chromosomal DNA, plastid DNA, mitochondrial DNA and extrachromosomal DNA molecules. The term "regeneration" as used herein in relation to plant materials means growing a whole, differentiated plant from a plant cell, a group of plant cells, a plant part such as, for example, from an embryo, scutellum, protoplast, callus, or other tissue, but not including growth of a plant from a seed.

The particular choice of a transformation technology will be determined by its efficiency to transform certain plant species as well as the experience and preference of the person practicing the invention with a particular methodology of choice. It will be apparent to the skilled person that the particular choice of a transformation system to introduce a nucleic acid construct into plant cells is not essential to or a limitation of the invention, provided it achieves an acceptable level of nucleic acid transfer. Guidance in the practical implementation of transformation systems for plant improvement is provided by Birch, *Ann Rev Plant Physiol Plant Mol Biol.* 48: 297-326, 1997.

In principle, both dicotyledonous and monocotyledonous plants that are amenable to transformation can be modified by introducing a nucleic acid construct according to the invention into a recipient cell and growing a new plant that harbors and expresses a polynucleotide according to the invention.

Introduction and expression of foreign or exogenous polynucleotides in dicotyledonous plants such as tobacco, potato and legumes or monocotyledonous plants such as cereals, including wheat, barley, rice, corn, oats, rye and sorghum has been shown to be possible using the T-DNA of the tumor-inducing (Ti) plasmid of *Agrobacterium tumefaciens* (See, for example, Umbeck, U.S. Pat. No. 5,004,863, and International application PCT/US93/02480). A construct of the invention may be introduced into a plant cell utilizing *A. tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is preferred that the *Agrobacterium* harbors a binary Ti plasmid system. Such a binary system comprises (1) a first Ti plasmid having a virulence region essential for the introduction of transfer DNA (T-DNA) into plants, and (2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells as, for example, described by De Framond, *Biotechnology,* 1: 262, 1983 and Hoekema et al., *Nature,* 303: 179, 1983. Such a binary system is preferred inter alia because it does not require integration into the Ti plasmid in *Agrobacterium.*

Methods involving the use of *Agrobacterium* include, but are not limited to: (a) co-cultivation of *Agrobacterium* with cultured isolated protoplasts; (b) transformation of plant cells or tissues with *Agrobacterium*; (c) transformation of seeds, apices or meristems with *Agrobacterium*, or (d) inoculation in planta such as the floral-dip method as described by Bechtold et al., *C.R. Acad. Sci. Paris,* 316: 1194, 1993 or in wheat (as described in WO 00/63398, herein incorporated by reference). This approach is based on the infiltration of a suspension of *Agrobacterium* cells. Alternatively, the chimeric construct may be introduced using root-inducing (Ri) plasmids of *Agrobacterium* as vectors.

Methods for transformation of cereal plants such as wheat and barley for introducing genetic variation into the plant by introduction of an exogenous nucleic acid and for regeneration of plants from protoplasts or immature plant embryos are well known in the art, see for example, Wan and Lemaux, *Plant Physiol.* 104: 37-48, 1994, Tingay et al., *Plant J.* 11: 1369-1376, 1997, Canadian Patent Application No. 2,092,588, Australian Patent Application No. 61781/94, Australian Patent No. 667939, U.S. Pat. No. 6,100,447, International Patent Application PCT/US97/10621, U.S. Pat. Nos. 5,589,617, 6,541,257. Preferably, transgenic wheat, barley or other cereal plants are produced by *Agrobacterium tumefaciens* mediated transformation procedures. Vectors carrying the desired nucleic acid construct may be introduced into regenerable cereal cells of tissue cultured plants or explants. The regenerable cells are preferably from the scutellum of immature embryos, mature embryos, callus derived from these, or the meristematic tissue. Immature embryos are preferably those from inflorescences about 10-15 days after anthesis.

The genetic construct can also be introduced into plant cells by electroporation as, for example, described by Fromm et al., *Proc. Natl. Acad. Sci. U.S.A.* 82: 5824, 1985 and Shimamoto et al., *Nature,* 338: 274-276, 1989. In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus.

Another method for introducing the nucleic acid construct into a plant cell is high velocity ballistic penetration by small particles (also known as particle bombardment or microprojectile bombardment) with the nucleic acid to be introduced contained either within the matrix of small beads or particles, or on the surface thereof as, for example described by Klein et al., *Nature,* 327: 70, 1987.

Alternatively, the nucleic acid construct can be introduced into a plant cell by contacting the plant cell using mechanical or chemical means. For example, a nucleic acid can be mechanically transferred by microinjection directly into plant cells by use of micropipettes. Alternatively, a nucleic acid may be transferred into the plant cell by using polyethylene glycol which forms a precipitation complex with genetic material that is taken up by the cell.

Mutagenesis

The plants of the invention can be produced and identified after mutagenesis. This may provide a plant which is non-transgenic, which is desirable in some markets.

Mutants can be either naturally occurring (that is to say, isolated from a natural source) or synthetic (for example, by performing mutagenesis on the nucleic acid) or induced. Generally, a progenitor plant cell, tissue, seed or plant may be subjected to mutagenesis to produce single or multiple mutations, such as nucleotide substitutions, deletions, additions and/or codon modification. In the context of this application, an "induced mutation" is an artificially induced genetic variation which may be the result of chemical, radiation or biologically-based mutagenesis, for example transposon or T-DNA insertion. Preferred mutations are null mutations such as nonsense mutations, frameshift mutations, insertional mutations or splice-site variants which completely inactivate the gene. Nucleotide insertional derivatives include 5' and 3' terminal fusions as well as intra-sequence insertions of single or multiple nucleotides. Insertional nucleotide sequence variants are those in which one or more nucleotides are introduced into the nucleotide sequence, which may be obtained by random insertion with suitable screening of the resulting products. Deletional variants are characterised by the removal of one or more nucleotides from the sequence. Preferably, a mutant gene has only a single insertion or deletion of a sequence of nucleotides relative to the wild-type gene. Substitutional nucleotide variants are those in which at least one nucleotide in the sequence has been removed and a different nucleotide inserted in its place. The preferred number of nucleotides affected by substitutions in a mutant gene relative to the wild-type gene is a maximum of ten nucleotides, more preferably a maximum of 9, 8, 7, 6, 5, 4, 3, or 2, or only one nucleotide. Such a substitution may be "silent" in that the substitution does not change the amino acid defined by the codon. Alternatively, conservative substituents are designed to alter one amino acid for another similar acting amino acid.

Typical conservative substitutions are those made in accordance with Table 9 "Exemplary substitutions".

The term "mutation" as used herein does not include silent nucleotide substitutions which do not affect the activity of the gene, and therefore includes only alterations in the gene sequence which affect the gene activity. The term "polymorphism" refers to any change in the nucleotide sequence including such silent nucleotide substitutions.

In a preferred embodiment, the plant comprises a deletion of at least part of a SSII gene or a frameshift or splice site variation in such gene.

Mutagenesis can be achieved by chemical or radiation means, for example EMS or sodium azide (Zwar and Chandler, *Planta* 197: 39-48, 1995) treatment of seed, or gamma irradiation, well know in the art. Isolation of mutants may be achieved by screening mutagenised plants or seed. For example, a mutagenized population of cereal plants may be screened for low SSII activity in the leaf or grain starch, mutation of the SSII gene by a PCR or heteroduplex based assay, or loss of the SSII protein by ELISA. In a polyploid plant, screening is preferably done in a genotype that already lacks one or two of the SSII activities, for example in a wheat plant already mutant in the SSII genes on two of the three genomes, so that a mutant entirely lacking the functional activity is sought. Alternatively, the mutation may be identified using techniques such as "tilling" in a population mutagenised with an agent such as EMS (Slade and Knauf, *Transgenic Res.* 14: 109-115, 2005). Such mutations may then be introduced into desirable genetic backgrounds by crossing the mutant with a plant of the desired genetic background and performing a suitable number of backcrosses to cross out the originally undesired parent background.

The mutation may have been introduced into the plant directly by mutagenesis or indirectly by crossing of two parental plants, one of which comprised the introduced mutation. The modified plants such as cereal plants may be transgenic or non-transgenic. Using mutagenesis, a non-transgenic plant lacking the function of interest may be produced. The invention also extends to the grain or other plant parts produced from the plants and any propagating material of the plants that can be used to produce the plants with the desired characteristics, such as cultured tissue or cells. The invention clearly extends to methods of producing or identifying such plants or the grain produced by such plants.

Plants of the invention can be produced using the process known as TILLING (Targeting Induced Local Lesions IN Genomes). In a first step, introduced mutations such as novel single base pair changes are induced in a population of plants by treating cells, seeds, pollen or other plant parts with a chemical mutagen or radiation, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as CelI, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique. TILLING is further described in Slade and Knauf, 2005 (supra), and Henikoff et al., *Plant Physiol.* 135: 630-636, 2004, herein incorporated by reference.

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., *Plant J.* 37: 778-786, 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Genetic Linkage

As used herein, the term "genetically linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart.

As used herein, the "other genetic markers" may be any molecules which are linked to a desired trait of a cereal plant such as wheat or barley. Such markers are well known to those skilled in the art and include molecular markers linked to genes determining traits such disease resistance, yield, plant morphology, grain quality, other dormancy traits such as grain colour, gibberellic acid content in the seed, plant height, flour colour and the like. Examples of such genes in wheat are stem-rust resistance genes Sr2 or Sr38, the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance (Eagles et al., *Aust. J. Agric. Res.* 52: 1 349-1356, 2001; Langridge et al., *Aust. J. Agric. Res.* 52: 1043-1077, 2001; Sharp et al., *Aust J Agric Res* 52: 1357-1366, 2001).

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants.

Any molecular biological technique known in the art which is capable of detecting alleles of an SSII or other gene can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, *Current Genomics,* 1: 301-311, 2000; Langridge et al., 2001 (supra)). The invention also includes the use of molecular marker techniques to detect polymorphisms linked to alleles of (for example) an SSII gene which confers altered fructan accumulation. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., 2001 (supra).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (McPherson and Moller (Ed), BIOS Scientific Publishers Ltd, Oxford, 2000). PCR can be performed on cDNA obtained from reverse transcribing mRNA isolated from plant cells expressing an SSII gene or on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook et al. (supra). Sequencing can be carried out by any suitable method, for example, dideoxy sequencing, chemical sequencing or variations thereof. Direct sequencing has the advantage of determining variation in any base pair of a particular sequence.

Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, endosperm, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are endosperm, scutellum, aleurone layer and embryo. The invention accordingly includes plants and plant parts and products comprising these, particularly grain comprising fructan.

As used herein, the term "grain" refers to mature seed of a plant, such as is typically harvested commercially in the field. Mature cereal grain such as wheat or barley commonly has a moisture content of less than about 18-20%.

A "transgenic plant" as used herein refers to a plant that contains a gene construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes.

The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "corresponding non-transgenic plant" refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein/enzyme defined herein in the desired plant or plant organ. Transgenic plant parts include all parts and cells of said plants comprising the transgene such as, for example, cultured tissues, callus and protoplasts.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers to amplify a specific DNA, the presence of which will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed may also be identified i.e. distinguished from non-transformed or wild-type plants by their phenotype, for example conferred by the presence of a selectable marker gene, or conferred by the phenotype of altered fructan content of the grain of the plant, or related phenotype such as altered starch synthase activity.

As used herein, "germination" refers to the emergence of the root tip from the seed coat after imbibition. "Germination rate" refers to the percentage of seeds in a population which have germinated over a period of time, for example 7 or 10 days, after imbibition. A population of seeds can be assessed daily over several days to determine the germination percentage over time. With regard to seeds of the present invention, as used herein the term "germination rate which is substantially the same" means that the germination rate of the transgenic seeds is at least 90%, that of isogenic wild-type seeds.

Plants provided by or contemplated for use in the practice of the present invention include angiosperms, including both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit. Preferably, the plant is a cereal plant. Examples of cereal plants include, but are not limited to, wheat, barley, rice, maize (corn), sorghum, oats, and rye. In one embodiment, the cereal plant is other than barley mutants M292, M342 or barley plants comprising the same SSII mutation, described in WO 02/37955, herein incorporated by reference, such as wheat, rice, maize or sorghum.

As used herein, the term "wheat" refers to any species of the Genus *Triticum*, including progenitors thereof, as well as progeny thereof produced by crosses with other species. As is understood in the art, hexaploid wheats such as bread wheat comprise three genomes which are commonly designated the A, B and D genomes, while tetraploid wheats such as durum wheat comprise two genomes commonly designated the A and B genomes. Each wheat genome comprises 7 pairs of chromosomes which may be observed by cytological methods during meiosis and thus identified, as is well known in the art. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T macha, T. compactum, T. sphaerococcum, T. vavilovii*, and interspecies cross thereof. Tetraploid wheat includes *T. durum* (also referred to herein as durum wheat or *Triticum turgidum* ssp. *durum*), *T. dicoccoides, T. dicoccum, T. polonicum*, and interspecies cross thereof. In addition, the term "wheat" includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to *Triticale*. Preferably, the wheat plant is suitable for commercial production of grain, such as commercial varieties of hexaploid wheat or durum wheat, having suitable agronomic characteristics which are known to those skilled in the art.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Food Production

In another aspect, the invention provides cereal plants and grain, and products obtained therefrom comprising fructan from the grain, that is useful for food or feed production, the grain having increased levels of fructan compared to corresponding wild-type grain. Preferably the plant from which the grain is obtained has a reduced level of SSII activity in the endosperm during development. The plant of the present invention is useful for food production and in particular for commercial food production. Such food production might include the making of flour, dough or other products that might be an ingredient in commercial food production. In an embodiment which is desirable for use in food production, the seed or grain of the plant has a fructan content that is increased relative to the wild-type plant. The grain may have a level of activity of degradative enzymes, particularly of one or more amylases such as α-amylase or β-amylase, which is reduced by the presence of a transgene or an introduced mutation which reduces expression of a gene encoding such a degradative enzyme in the grain. Flour or dough from such grain has desirable properties for baking or other food production.

The desired genetic background of the plant will include considerations of agronomic yield and other characteristics. Such characteristics might include whether it is desired to have a winter or spring types, agronomic performance, disease resistance and abiotic stress resistance. For Australian use, one might want to cross the altered fructan trait into wheat cultivars such as Baxter, Kennedy, Janz, Frame, Rosella, Cadoux, Diamondbird or other commonly grown varieties. Other varieties will be suited for other growing regions. It is preferred that the plant, preferably wheat, variety of the invention provide a yield not less than 80% of the corresponding wild-type variety in at least some growing regions, more preferably not less than 85% and even more preferably not less than 90%. The yield can readily be measured in controlled field trials.

In further embodiments, other desirable characteristics include the capacity to mill the grain, in particular the grain hardness. Another aspect that might make a plant of higher value is the degree of fructan or starch extraction from the grain, the higher extraction rates being more useful, or the protein content, the ration of amylose to amylopectin, or the content of other non-starch polysaccharides such as β-glucan which also contribute to the dietary fibre content of the grain products. Grain shape is also another feature that can impact on the commercial usefulness of a plant, thus grain shape can have an impact on the ease or otherwise with which the grain can be milled.

Starch is readily isolated from grain of the invention using standard methods, for example the method of Schulman and Kammiovirta, *Starch*, 43: 387-389, 1991. On an industrial scale, wet or dry milling can be used. Starch granule size is important in the starch processing industry where there is separation of the larger A granules from the smaller B granules.

Food Products

The invention also encompasses foods, beverages or pharmaceutical preparations produced with products, preferably those comprising increased fructan, obtained from the plants or grain of the invention. Such food production might include the making of processed grain, wholemeal, flour, dough or other products that might be an ingredient in commercial food production. The grain of the invention or products derived therefrom containing fructan may be used in a variety of food applications for human consumption. As used herein, "humans" refers to *Homo sapiens*. The grain can be used readily in food processing procedures and therefore the invention includes milled, ground, kibbled, pearled or rolled grain or products obtained from the processed or whole grain of the plants of the invention, including flour. These products may be then used in various food products, for example farinaceous products such as breads, cakes, biscuits and the like or food additives such as thickeners or binding agents or to make drinks, noodles, pasta or quick soups. The grain or products derived from the grain of the invention are particularly desired in breakfast cereals or as extruded products. The fructan may be incorporated into fat or oil products such as margarine or shortening, salad dressing, egg products such as mayonnaise, dairy products such as icecream, yogurt or cheese, cereal products such as corn or wheat flour, fruit juices, other foods or food materials, or the fructan may be processed into beverages or foods such as bread, cake, biscuits, breakfast cereals, pasta, noodles or sauces. Fructan is also useful as a low calorie sweetening product.

In bread, the ingredients comprising fructan which may be in the form of flour or wholemeal may substitute for 10% (w/w) or more of unaltered flour or wholemeal, preferably substituting at least 30% and even more preferably at least 50% of the unaltered flour or wholemeal. The formulation might therefore be, for example, flour 70 parts, high-fructan starch 30 parts, fat 2 parts, salt 2 parts, improver 1 part, yeast 2.5 parts. The production of the bread may be by a rapid dough technique or other techniques as is known by those skilled in the art.

Alternatively, the high-fructan product of the invention may be incorporated into a farinaceous based pasta product. The amount of fructan of the invention employed in the pasta composition may be in the range of 5-20% (w/w) based on the total weight of farinaceous material more particularly in the range of 10 to 20%. Suitable other farinaceous materials will readily be chosen by a person skilled in the art. Other material may also be added to the composition for example dry or liquid eggs (yolks, whites, or both) or high protein substances such as milk protein or fish protein. Vitamins, minerals, calcium salts, amino acids, buffering agents such as disodium hydrogen phosphate, seasoning, gum, gluten or glyceryl monostearate may also be added.

Other parts of the plants of the invention that are edible may be used as foods for human consumption or as feed for animal use. For example, leaves, stems, roots, tubers, fruit, pods or extracts or parts of these comprising cells of the invention from any of these may be used for human or animal consumption. Increased fructan content of the plants of the invention and parts thereof may provide advantages for use of these materials as animal feed such as, for example, as feed for pigs, cattle, horses, poultry such as chickens and other animals.

Methods

The products or compounds of the present invention can be formulated in pharmaceutic compositions which are prepared according to conventional pharmaceutical compounding techniques. See, for example, Remington's Pharmaceutical Sciences, 18$^{th}$ Ed. Mack Publishing, Company, Easton, Pa., U.S.A., 1990. The composition may contain the active agent or pharmaceutically acceptable derivative active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration.

For oral administration, the compounds can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques.

The active agent is preferably administered in a therapeutically effective amount. An "effective amount" includes an amount of fructan or fructan containing product to promote an improvement in indicators of intestinal health or an improvement in indicators of severity of the condition such as diabetes, obesity, heart disease, hypertension, constipation, osteoporesis and cancer. The actual amount administered and the rate and time-course of administration will depend on the nature and severity of the condition being treated. Prescription of treatment, e.g. decisions on dosage, timing, etc. is within the responsibility of general practitioners or specialists and typically takes account of the disorder to be treated, the condition of the individual patient, the site of delivery, the method of administration and other factors known to practitioners. Examples of techniques and protocols can be found in Remington's Pharmaceutical Sciences, (supra).

The food or beverage or pharmaceutical preparation may be packaged ready for sale or in bulk form. The invention also provides methods of preparing the food, beverage or pharmaceutical preparation of the invention, and recipes or instructions for preparing such foods or beverages. The methods may comprise the steps of harvesting the plant or plant part, separating grain from other plant parts, crushing, extracting, milling, cooking, canning, packaging or other processing steps known in the art. The methods or recipes or instructions may include the steps of processing the plant product of the invention and/or admixing it with other food ingredients, such as heating or baking the mixture or the product to, for example, at least 100° C. The method may include the step of packaging the product so that it is ready for sale.

In some preferred but not essential embodiments the invention is directed to products and compositions for use in the herein described methods and does not extend to methods for the treatment of the human or animal body by surgery or therapy and diasgnostic methods practiced on the human or animal body.

In some embodiments the invention is directed to the use of the subject products or compositions in the manufacture of a medicament for inter alia increasing intestinal health or, amealiorating one or more symptoms of a condition associated with low levels of dietary fructan, such as diabetes, obesity, heart disease, hypertension, constipation, osteoporesis and cancer.

Industrial Use

The plant products, preferably grain, may be used in production of industrial products such as, for example, ethanol.

The present invention is further described by the following non-limiting Examples.

EXAMPLES

Example 1

Illustrative Methods and Materials

Plant Material

The mutant barley (*Hordeum vulgare*) lines M292 and M342, which were homozygous for a null mutation in the gene encoding SSIIa, were obtained following mutagenesis of grains of the barley variety 'Himalaya' with sodium azide (Morell et al. 2003 (supra)). Mutant seeds were initially selected from progeny grain of the mutagenised population on the basis of a shrunken grain phenotype. This phenotype can be scored readily in a large population of mutagenized seed. The mutant lines were further characterised by their altered starch properties, reduced SSIIa protein level and activity, and genetically by the presence of a premature stop codon in the protein coding region of the gene encoding SSIIa (Morell et al. 2003 (supra)).

Both wild-type Himalaya and the mutant plants were grown in a controlled growth cabinet at day and night temperatures of 18° C. and 12° C. respectively with a 12 hour day-length. Barley spikes were labelled as at anthesis 2 days after the awns first appeared through the top of the flag leaf containing the enclosed spike. Developing seeds were harvested at 20 days post anthesis (DPA) and after removal of the embryo the developing endosperm was extruded through the cut surface and stored at −80° C.

Cereal cultivars and other varieties as described herein were obtained commercially or from the Australian Winter Cereals Collection, Tamworth, NSW, Australia. Crossing of plants such as barley plants was carried out in the greenhouse by standard methods.

Grain Characteristics

Grain was harvested from plants at maturity. Average seed weight was determined by weighing 100 seeds and expressed as an average weight per grain (mg). Seed moisture content of grain was measured by standard nuclear magnetic resonance (NMR) methods using an Oxford 4000 NMR Magnet (Oxford analytical instruments Limited). Grain texture was measured using the Single-Kernel Characterization system 4100 (Perten Instruments Inc. Springfield, Ill. 62707 USA) using the RACI Cereal Chemistry Official testing method 12-01.

Milling of Grain

Grain was ground to wholemeal that would pass through a 0.5 mm sieve, using a cyclonic mill (Cyclotec 1093, Tecator, Sweden). The wholemeal was then used for the analysis below.

β-Glucan Analysis

α-glucan content was assayed as described in Megazyme Method (AACC32.23), using 20 mg of wholemeal for each of three replicate samples.

Total Starch Analysis

Total starch content of grain was assayed as described in Megazyme Method (AACC76.13) using 20 mg of wholemeal for each of three replicate samples.

Wholemeal was obtained by milling grain. Starch was isolated from the wholemeal using the method of Schulman and Kammiovirta, 1991 (supra).

Analysis of Starch Composition and Characteristics

Amylose and amylopectin contents in the starch of the grain, or the ratio of amylose to amylopectin, was determined by Sepharose CL-2B gel filtration as follows (Gel filtration method). Approximately 10 mg of total starch was dissolved in 3.0 ml of 1M NaOH and fractionated on the basis of molecular weight by chromatography on a Sepharose CL-2B column (Regina et al., 2006 (supra)). The amount of starch in each of the fractions from the column were measured using the Starch Assay Kit (Sigma) according to the suppliers instructions. The total amount of amylopectin (first peak, higher molecular weight) and amylose (second peak, lower molecular weight) was calculated and the ratio or contents determined.

The distribution of chain lengths in the amylopectin of the starch may be analysed by fluorophore assisted carbohydrate electrophoresis (FACE) using a capillary electrophoresis unit according to Morell et al., *Electrophoresis*, 19: 2603-2611, 1998, after debranching of the starch samples. For example, amylopectin chain length distribution may be measured using a P/ACE 5510 capillary electrophoresis system (Beckman Coulter, NSW Australia) with argon laser-induced fluorescence (LIF) detection. Molar difference plots may be generated by subtracting the normalized chain length distribution for modified starch from the normalized distribution for starch from an isogenic non modified control.

The gelatinisation temperature profiles of starch samples may be measured using a Pyris 1 differential scanning calorimeter (Perkin Elmer, Norwalk Conn., USA). The viscosity of starch solutions may be measured on a Rapid-Visco-Analyser (RVA, Newport Scientific Pty Ltd, Warriewood, Sydney), using conditions as reported by Batey et al., *J. Sci. Food Agric.* 74: 503-508, 1997. The parameters that may be measured include peak viscosity (the maximum hot paste viscosity), holding strength, final viscosity and pasting temperature. Pasting properties may be measured using the Rapid Visco Analyser as follows. Starch (3.0 g) is added to distilled water (25.0 ml) in the DSC pan and the RVA run profile is: 2 mins at 50° C., heat for 6 mins to 95° C., hold at 95° C. for 4 mins, cool for 4 mins to 50° C., hold at 50° C. for 4 mins. The measured parameters are: Peak viscosity at 95° C., Holding strength at end of 95° C. holding period, Breakdown=Peak Viscosity−Holding strength, Final viscosity at end of 50° C. holding period, Setback=Final Viscosity−Holding strength. The software Thermocline for Windows version 2.2 (Newport Scientific Pty Ltd, NSW Australia) may be used for collection and analysis of data.

The swelling volume of flour or starch may be determined according to the method of Konik-Rose et al. *Starch/die Stärke* 53:14-20, 2001. The uptake of water is measured by weighing the sample prior to and after mixing the flour or starch sample in water at defined temperatures (for example, 90° C.) and following collection of the gelatinized material.

Lipid Analysis

Total lipid content was assayed by NMR using an Oxford 4000 NMR Magnet, Oxford Analytical Instruments Limited, UK. For each sample, 1 g of seeds was dried at 38.8° C. for 64 hours. The dried seeds were then measured using NMR and compared against a pure barley oil controls extracted from cv. Himalaya or M292 grain.

Protein Analysis

Protein content was estimated by determining the total nitrogen content of the seed using the method of Dumas (RACI Method 02-03, 2003) and expressing the result as "protein" by multiplying the value obtained by a factor of 5.7. For each sample 10 mg of wholemeal was used and the nitrogen content was detected by mass spectrometry.

Total Dietary Fibre Assay

The gravimetric method of Prosky et al., *J Assoc Off Agric Chem* 68: 677, 1985 was used to determine total dietary fibre (TDF) of the wholemeal. Duplicate samples were assayed.

Non Starch Polysaccharide Assay

Total neutral non-starch polysaccharides (NSP) were measured by a modification of the gas chromatographic procedure of Theander et al., *J AOAC Int* 78: 1030-1044, 1995. The modification involved a 2-hour hydrolysis with 1 M sulphuric acid followed by centrifugation to remove insoluble NSP and a further hydrolysis of the supernatant using 2 M trifluoroacetic acid for soluble NSP.

Resistant Starch Assay

An in vitro procedure was used to determine resistant starch (RS) content. The method has two sections: firstly, starch in each sample was hydrolysed under simulated physiological conditions; secondly, by-products were removed through washing and the residual starch determined after homogenization and drying of the sample. Starch quantitated at the end of the digestion treatment represented the resistant starch content of the sample. Typically, triplicate samples of whole meal along with appropriate standards were mixed with artificial saliva and the resultant bolus incubated with pancreatic and gastric enzymes at physiological pH and temperature. The amount of residual starch in the digesta was determined using conventional enzymatic techniques and spectrophotometry and the resistant starch content of the sample expressed as a percentage of sample weight or total starch content.

On day 1, an amount of sample representing up to 500 mg of carbohydrate was weighed into a 125 mL Erlenmeyer flask. A carbonate buffer was prepared by dissolving 121 mg of $NaHCO_3$ and 157 mg of KCl in approximately 90 mL purified water, adding 159 µL of 1 M $CaCl_2.6H_2O$ solution and 41 µL of 0.49 M $MgCl_2.6H_2O$, adjusting the pH to 7 to 7.1 with 0.32 M HCl, and adjusting the volume to 100 mL. This buffer was stored at 4° C. for up to five days. An artificial saliva solution containing 250 units of α-amylase (Sigma A-3176 Type VI-B from porcine pancreas) per mL of the carbonate buffer was prepared. An amount of the artificial saliva solution, approximately equal to the weight of food, was added to the flask. About 15-20 sec after adding the saliva, 5 mL of pepsin solution in HCl (1 mg/mL pepsin (Sigma) in 0.02 M HCl, pH 2.0, made up on day of use) was added to each flask. The mixing of the amylase and then pepsin mimicked a human chewing the sample before swallowing it. The mixture was incubated at 37° C. for 30 min with shaking at 85 rpm. The mixture was then neutralised with 5 mL of 0.02M NaOH. 25 mL of acetate buffer (0.2 M, pH 6) and 5 mL of pancreatin enzyme mixture containing 2 mg/mL pancreatin (Sigma, porcine pancreas at 4×USP activity) and 28 U of amyloglucosidase (AMG, Sigma) from *Aspergillus niger* in acetate buffer, pH6, were added per flask. Each flask was capped with aluminium foil and incubated at 37° C. for 16 hours in a reciprocating water bath set to 85 rpm.

On day 2, the contents of each flask was transferred quantitatively to a 50 mL polypropylene tube and centrifuged at 2000×g for 10 min at room temperature. The supernatants were discarded and each pellet washed three times with 20 mL of water, gently vortexing the tube with each wash to break up the pellet, followed by centrifugation. 50 uL of the last water wash was tested with Glucose Trinder reagent for the absence of free glucose. Each pellet was then resuspended in approximately 6 mL of purified water and homogenised three times for 10 seconds using an Ultra Turrax TP18/10 with an S25N-8G dispersing tool. The contents were quantitatively transferred to a 25 mL volumetric flask and made to volume. The contents were mixed thoroughly and returned to the polypropylene tube. A 5 mL sample of each suspension was transferred to a 25 mL culture tube and immediately shell frozen in liquid nitrogen and freeze dried.

On day 3, total starch in each sample was measured using reagents supplied in the Megazyme Total Starch Procedure kit. Starch standards (Regular Maize Starch, Sigma S-5296) and an assay reagent blank were prepared. Samples, controls and reagent blanks were wet with 0.4 mL of 80% ethanol to aid dispersion, followed by vortexing. Immediately, 2 mL of DMSO was added and solutions mixed by vortexing. The tubes were placed in a boiling water bath for 5 min, and 3 mL of thermostable α-amylase (100 U/ml) in MOPS buffer (pH 7, containing 5 mM $CaCl_2$ and 0.02% sodium azide added immediately. Solutions were incubated in the boiling water bath for a further 12 min, with vortex mixing at 3 min intervals. Tubes were then placed in a 50° C. water bath and 4 mL of sodium acetate buffer (200 mM, pH 4.5, containing 0.02% sodium azide) and 0.1 mL of amyloglucosidase at 300 U/ml added. The mixtures were incubated at 50° C. for 30 min with gentle mixing at 10 min intervals. The volumes were made up to 25 mL in a volumetric flask and mixed well. Aliquots were centrifuged at 2000×g for 10 min. The amount of glucose in 50 µL of supernatant was determined with 1.0 mL of Glucose Trinder reagent and measuring the absorbance at 505 nm after incubation of the tubes at room temperature in the dark for a minimum of 18 min and a maximum of 45 min.

Quantification of Sucrose, Hexoses and Fructo-Oligosaccharides

Total sugars were extracted from wholemeal following the method of Lunn and Hatch, *Planta* 197: 385-391, 1995 with the following modification. Wholemeal such as barley wholemeal (100 mg) was extracted 3 times with 10 ml of 80% ethanol (v/v) in a boiling water bath for 10 minutes. The supernatant from each extraction was pooled and freeze dried, then re-suspended in 2 ml milliQ water. The quantities of sucrose, glucose, and fructose were measured using a colorimetric microtiter plate enzymatic assay as described (Campbell et al., *Journal of the science of food and agriculture* 79: 232-236, 1999; Ruuska et al., *Functional Plant Biology* 33: 799-809, 2006). Sugars and fructo-oligosaccharides were also analysed by high performance anion exchange chromatography (HPAEC) as described in Ruuska et al., 2006 (supra); both methods resulted in comparable values.

To determine maltose levels, total sugars extracted from barley whole meal were assayed essentially as described by Bernfeld, In: Colowick S, Kaplan N (eds), *Methods in enzymology*. Academic, NY, p 149, 1955, using maltose standard solutions for comparison, as follows. Total sugars were diluted 10 to 100-fold. Maltose standards (10 tubes) were prepared as 0.3 to 5 micromoles per ml. One ml of each dilution of maltose (in total sugars or maltose dilutions) was mixed with 1 ml of dinitrosalicylic acid colour reagent. The sugar solution was then incubated at 100° C. for 5 minutes and cooled to room temperature. Ten ml reagent grade water was added to each tube and mixed well. The samples were measured at $A_{540}$ with a spectrophotometer. Maltose was also determined by HPAEC as described above.

Enzyme Assays

Total starch synthase activity in samples such as developing endosperm of cereals may be measured by extraction of proteins and assay by the methods described in Libessart et al. *Plant Cell* 7(8): 1117-1127, 1995 or Cao et al., *Plant Physiol.* 120: 205-215, 1999. The assays use $^{14}C$ labeled ADPG substrate and measure incorporation of the monomer into starch polymers. Individual isoforms of starch synthase in extracts may be separated by gel electrophoresis and assayed in-gel (zymogram) as follows. Extracts from samples such as developing seeds may be prepared using 50 mM potassium phosphate buffer, pH7.5, 5 mM EDTA, 20% glycerol, 10 µM Pefabloc and 0.05 mM dithiothreitol (DTT). After grinding the seeds to a pulp in the buffer or homogenizing the sample, the mixture is centrifuged at 14,000 g for 15 min at 4° C. and the supernatant drawn off. The protein concentration in the supernatant may be measured using Coomassie Protein Reagent or other standard means. Extracts may be stored at –80° C. if the protein extracts are to be run on native gels. For denaturing gel electrophoresis, 100 µl of extract is mixed with SDS and β-mercaptoethanol and the mixtures are incubated in boiling water for 4 min to denature the proteins. Electrophoresis is carried out in standard denaturing polyacrylamide gels using 8% polyacrylamide separating gels overlaid with 4.5% polyacrylamide stacking gels. After electophoresis, the proteins may be renatured by soaking the gels in 40 mM Tris-HCl buffers for a minimum of 2 hr, changing the buffer every 30 min and using at least 100 mL of buffer for each buffer change. For non-denaturing gels, the denaturing step with SDS and β-mercaptoethanol is omitted and SDS omitted from the gels. A starch synthase assay buffer including Tris-glycine (25 mM Tris, 0.19M glycine), 0.133M ammonium sulphate, 10 mM $MgCl_2$, 670 µg/mL BSA and 1 mM ADPG substrate may be used to detect starch synthase bands, followed by staining with 2% KI, 0.2% $I_2$ iodine solution to detect the starch product.

Alternatively, starch synthase or other starch biosynthetic enzymes may be detected in samples using specific antibodies (ELISA).

cDNA Array

The New South Wales Centre for Agricultural Genomics (NSWCAG) array contained 19,635 wheat cDNA clones and 1,613 barley cDNA clones of which about 16,000 were unique in nucleotide sequence, wherein a "unique" sequence is defined herein as having less than 80% sequence identity at the nucleotide level to all of the other sequences. The design of this array and the cDNA libraries that contributed to its construction are detailed in Clarke and Rahman, *Theoretical and Applied Genetics*, 110: 1259-1267, 2005.

Extraction of RNA

To extract total RNA from developing endosperm, samples of eight endosperms each were frozen in liquid $N_2$ and ground to a fine powder with the aid of acid washed sand in a mortar containing 2 ml of NTES (0.1 M NaCl, 10 mM Tris-HCl (pH 8.0), 1 mM EDTA, 1% (w/v) SDS). Two ml of phenol/chloroform was added to the homogenized mixture and again ground well. This mixture was transferred to a capped tube, vortexed for one minute and incubated on ice for 30 minutes. The two phases were separated by centrifuging the tubes at 5,500 g for 15 minutes at 4° C., the aqueous phase transferred to a new tube and an equal volume of 4 M LiCl/10 mM EDTA added to precipitate the RNA. After thorough mixing, the samples were kept at –20° C. over night. Samples were thawed and spun at 7,000 g for 45 minutes at 4° C. The supernatant was discarded and the pellet containing the RNA rinsed with 1 ml of 70% ethanol, dried and re-suspended in 250 µl of water. The soluble fraction was transferred to a new microcentrifuge tube. To remove starch contamination from the isolated RNA, 3.5 µl of 3 M NaOAc and 125 µl of ethanol (EtOH) was added followed by mixing and centrifugation at 13,000 rpm for 10 min at 4° C. The supernatant was removed to a new tube and 21.5 µl of 3 M NaOAc and 375 µl of EtOH added to precipitate the RNA. The precipitated RNA was rinsed with 70% EtOH then dried and re-suspended in 30 µl of water. To determine the concentration and purity of the RNA, aliquots were diluted 1 in 300 in sterile distilled water and the absorbance measured at $A_{260}$ and $A_{280}$.

Microarray Analysis

For microarray analysis, four biological replicates were used for the mRNA comparisons. For each labeling experiment, 50 µg of total RNA was used for both the Cy3 and Cy5 dyes (Amersham Pharmacia, UK), following the two-step labelling method of Schenk et al., *Proc. Natl. Acad. Sci. U.S.A.* 97: 11655-11660, 2000. RNA from the control plant, 'Himalaya' was labelled with Cy3 in the un-swapped replicates. The dye labelling of the samples was reversed for two of the replicates to minimize any bias in cDNA incorporation and photo-bleaching of the fluorescent dyes. The pre-hybridization of the microarray slides, hybridization of samples and subsequent washing of the slides to remove unbound target was performed as per the supplied protocol for the CMT-GAPS™ coated microscope slides (Corning USA). The slides were scanned with a GenePix 4000A microarray scanner (Axon Instruments, Union, Calif., USA). The features were analyzed using the GenePix Pro 4 software and unsatisfactorily segmented features were either manually adjusted or discarded to ensure the integrity of the data obtained.

The analysis of the microarray data files was carried out using functions contained in tRMA (tools for R Microarray Analysis; Wilson et al., *Bioinformatics* 19: 1325-1332, 2003) these functions operate as part of a statistical software package called R (http://www.r-project.org/). A detailed description of tRMA is available online (www.csiro.au/gena/trma). The data sets generated from the GenePix software were loaded into tRMA using the "LoadGenePixFile" function. Normalization of $\log_2$ ratio values was performed using the "SpatiallyNormalize" function. This method of normalization corrected for spatial and intensity-dependent effects of fluorescence across the microarray slide (Wilson et al., 2003 (supra)). In addition, the possible biases in fluorescence due to differences in the efficiency of incorporation of the two dyes and unequal loading of cDNA samples were also corrected. Using the median values of the normalized log ratios for each gene in each replicate, differentially expressed genes were determined using the "FindDiffExpGenes" function at a stringency level of 1e–10. Differentially expressed genes are selected as outliers in a Gaussian distribution of the entire data set. Therefore, a ratio cut-off was empirically computed from the normalized $\log_2$ ratio data, which were rescaled and centered in order to make direct comparisons between slides in all four replicates. The same slide data was also compared using a different function. In this analysis after slide normalization the "FindDiffExpGenes" function was performed on the individual slides at the default stringency (1e–3). Then "CompareInterestingGenes" function was used to find the differentially expressed genes common to all replicates.

To obtain the nucleotide sequence of cloned genes or, for example, to confirm the identity of the differentially expressed genes, the clones were sequenced using 0.12 µg of PCR amplified insert as the template, from both the 3' and 5' ends using primers such as M13/pUC reverse and forward primers and Big Dye Terminator Cycle Sequencing (ABI).

RNA Electrophoresis and Hybridization Conditions

For each sample, 10 µg of total RNA was separated in a 1.4% agarose-formaldehyde gel (w/v) and transferred to Hybond N+ membrane (Amersham Pharmacia Biotech UK Ltd.) using the standard alkali transfer protocol supplied by the manufacturer.

Probes used for RNA hybridizations were made by amplifying the inserts from cDNA clones. PCR SuperMix (Invitrogen) was used with 3 pmoles of each primer and 50 ng template DNA in 10 αl reaction mix. The probes were amplified under the following conditions; cycle 1, 94° C. for 5 minutes; cycle 2, 94° C. for 30 seconds, 55° C. for 30 seconds and 72° C. for 2 minutes, repeat cycle 2 for 35 cycles. The inserts were labeled using the "Megaprime™ DNA labelling system" (Amersham Biosciences). In addition the clone pTa250.2, containing the coding sequences of the ribosomal genes (Appels and Dvorak, *Theoretical and Applied Genetics*, 63: 337-348, 1982) was used to estimate the uniformity of loading for the RNA from Himalaya and M292 onto the gels.

Hybridization of probes was at 65° C. in Khandjian hybridization buffer (Khandjian, *Bio/Technology*, 5: 165-167, 1987). The membrane was washed once for 30 minutes at 65° C. with 2×SSC and 0.1% (w/v) SDS, and twice for 40 minutes at 65° C. with 0.2×SSC and 0.1% (w/v) SDS, which corresponds to a high stringency wash. The membrane was exposed using a Fujifilm FLA-5000 series fluorescent image analyzer system and the image obtained was analyzed using the Multi Gauge version-2 analysis software (Fuji Photo Film Co. Ltd., 26-30 Nishiazabu, 2-Chome Minato-ku Tokyo 106-8620, Japan). The variation in hybridization intensities between the Himalaya and M292 RNA samples was measured (pixels per mm$^2$) and a correction was made for the level of background hybridization to the gel lanes.

Example 2

Composition and Functional Parameters of M292 Barley Grain

A detailed analysis was undertaken of the composition of mature grain from the barley SSIIa mutant M292 with a comparison to wild-type grain (Himalaya) grown under the same conditions. The results are summarized in Table 1.

M292 producing thinner grains with an unfilled central region ("shrunken"). The moisture content of the M292 grain was 10.2% as measured by the NMR method compared to 10.6% for Himalaya. The average grain weight for M292 was 36.4 mg/grain compared to Himalaya at 46.3 mg/grain, which represents a 21% reduction for M292, primarily due to reduction in the starch content from 27.7 mg/grain to 10.6 mg/grain (62% reduction). The reduction in starch came mostly from less amylopectin (84% reduction) while the amylose level was reduced by only 25%. Consequently, the percentage starch as amylose increased from about 37% in the wild-type to about 73% in M292 as determined by the gel filtration method.

TABLE 1

Grain composition of barley M292 at maturity

| | Content in Himalaya | | Content in M292 | | Ratio M292/Him. |
|---|---|---|---|---|---|
| | (mg/ grain) | (% of total grain) | (mg/ grain) | (% of total grain) | (on a mg per grain basis) |
| Seed weight | 46.3 | | 36.4 | | 0.79 |
| Starch | 27.7 | 59.9 | 10.6 | 29.1 | 0.38 |
| amylose | 10.4 | 26.1 | 7.8 | 21.4 | 0.75 |

TABLE 1-continued

Grain composition of barley M292 at maturity

|  | Content in Himalaya | | Content in M292 | | Ratio M292/Him. |
| --- | --- | --- | --- | --- | --- |
|  | (mg/ grain) | (% of total grain) | (mg/ grain) | (% of total grain) | (on a mg per grain basis) |
| amylopectin | 17.3 | 43.6 | 2.8 | 7.7 | 0.16 |
| Protein | 5.9 | 12.8 | 7.0 | 19.3 | 1.2 |
| Total NSP | 5.6 | 12.1 | 7.4 | 20.3 | 1.3 |
| Lipid | 1.5 | 3.2 | 2.5 | 6.9 | 1.7 |
| Sugars (total) | 0.07 | 0.16 | 0.6 | 1.6 | 8.6 |
| glucose | 0.005 |  | 0.08 |  | 16.0 |
| fructose | 0.005 |  | 0.09 |  | 18.0 |
| sucrose | 0.060 |  | 0.39 |  | 6.5 |
| maltose | 0.005 |  | 0.03 |  | 6.0 |
| Fructan | 0.1 | 0.2 | 4.2 | 11.5 | 42.0 |
| Ash | 1.1 | 2.4 | 0.8 | 2.2 | 0.73 |
| Moisture | 4.9 | 10.6 | 3.7 | 10.2 |  |
| Total content (incl. water) | 47.4 | 102.4 | 36.8 | 101.1 |  |
| Resistant starch | 0.3 | 0.7 | 1.3 | 3.6 | 4.3 |
| Beta-glucan | 2.7 | 5.8 | 3.6 | 9.9 | 1.3 |
| Dietary fibre | 7.2 | 15.6 | 9.2 | 25.3 | 1.3 |
| Arabinoxylan | 2.5 | 5.5 | 3.1 | 8.6 | 1.2 |

Note:
Total content is a sum of components in bold type; NSP: Non starch polysaccharide.

The reduced starch amount in M292 was compensated for in part by increases in the amounts of non-starch components. The contents of protein, total NSP and lipid (measured as mg per grain), which together make up about 46% of the grain weight of M292, were increased by 1.2, 1.3 and 1.7-fold, respectively. As a percentage of total M292 grain weight, the increases were even greater. The levels of free sugars were increased in M292 by about 8-fold in total, with individual sugars increasing between 6- and 18-fold. Of the other carbohydrate components, α-glucan and arabinoxylans were increased in the mutant by 1.3 and 1.2-fold, respectively. Unexpectedly and surprisingly, fructo-oligosaccharides (fructans) were increased massively by 42.0-fold. The extent of this increase was most surprising since α-glucan and arabinoxylans, which are also polymeric carbohydrates, were increased only modestly. The increase for fructan in terms of percentage of total grain weight was from 0.2% for Himalaya to 11.5% for M292. It is believed such a high level of fructan has never before been seen in a grain.

The total carbohydrate content (including starch, total NSP, free sugar and fructan) was reduced from 33.5 mg/grain present in wild-type Himalaya grain to 22.8 mg/grain in M292. The amount of resistant starch (RS) as determined by the in vitro method as described in Example 1 was increased in M292 by 4.3 fold (mg per grain). This indicated a much increased extent of protection of the starch from amylase digestion, presumably due to an altered starch granule structure and related to the increased proportion of amylose in the starch. Increased levels of lipid, α-glucan and fructan are also thought to have contributed to the increased level of RS.

The composition of the soluble carbohydrate components was further examined by HPAEC to study the changes in the oligosaccharides. The chromatography profiles (FIG. 1) confirmed the increased content of sucrose, maltose and hexoses in M292, as well as increased levels of a range of fructo-oligosaccharides, which showed a degree of polymerization (DP) of from 3 up to about 12. The wild-type Himalaya grain contained negligible or undetectable levels of fructo-oligosaccharides having a DP of about 6 or above.

Changes in cell wall polysaccharides can affect the hardness of the mature barley grain (Tsuchiya et al., *Physiologia Plantarum* 125: 181-191, 2005; Fincher and Stone, *Advances in Cereal Science and Technol* 8: 207-295, 1986). As there were significant changes of total NSP in M292, grain hardness was measured to determine the level of changes. The measurements were taken using the Single-Kernel Characterization System (SKCS) to obtain an average hardness index (HI) based on measurements from 300 grains. For M292 the HI value was 109±15 and the HI value for Himalaya was 84±17, indicating an increase in grain hardness for the mutant.

The contents of protein, total NSP and lipid (measured as mg per grain) which together make up about half the grain weight of M292, were increased in absolute amount and as a percentage of total grain weight, by a 1.2, 1.3 and 1.7-fold change respectively. Of the carbohydrate components which may be particularly significant in a nutritional context, α-glucan, arabinoxylans and fructo-oligosaccharides, were increased in the mutant by, 1.3-, 1.2-, and 42.0-fold, respectively. The resistant starch (the proportion of the total starch that is resistant to digestion in the human small intestine) was also increased in M292 by 4.3 fold change when expressed as mg per grain. The total content of carbohydrates (including starch, total NSP, free sugar and fructan) in M292 reduced to 22.8 mg compared to 33.5 mg present in wild-type Himalaya on a mg per grain basis.

Discussion

The identification and initial characterization of the barley M292 mutant was described by Morell et al. 2003 (supra) and Topping et al., 2003 (supra). Using linkage analysis and subsequent sequencing of the candidate gene, Morell et al. 2003 (supra) demonstrated that the mutation was caused by a stop codon introduced into SSIIa and resulted in a shrunken grain in which the seed weight was reduced from an average of 46 mg in Himalaya to 36 mg in M292 (Table 1) producing a thinner seed with an unfilled central region. The decreased starch, grain weight and modified starch composition observed here were consistent with previous studies (Morell et al. 2003 (supra)). The inventors have also shown increased levels of protein, total NSP, and lipid both on an individual grain basis and as a percentage, consistent with determinations reported earlier (percentage of total grain basis, Bird et al., 2004a (supra)).

In addition, the inventors have also shown, for the first, time significantly increased levels of free sugars and fructo-oligosaccharides. As well as increased resistant starch, β-glucan, and dietary fibre, the higher fructo-oligosaccharides determined here are expected to be important for providing beneficial dietary outcomes.

Example 3

Identification of Differentially Expressed Genes Using a cDNA Microarray

A microarray containing 19,635 wheat clones and 1,613 barley clones of which about 16,000 were unique sequences was obtained from the New South Wales Centre for Agricultural Genomics (NSWCAG). A "unique" sequence is defined herein as a sequence having less than 80% sequence identity at the nucleotide level to all other sequences in the set. The design of this array and the cDNA libraries that contributed to its construction are detailed in Clarke and Rahman, 2005 (supra).

The array was hybridized using total RNA from developing endosperm (20 DPA) of M292 or the wild type 'Himalaya' (control). At this time point, the levels of starch and protein were increasing in the developing barley grain. It was expected that the transcriptional changes to the starch biosynthetic pathway, caused by the mutation in the SSIIa gene, would be most evident at this timepoint. Seeds at the same age and morphological stage of development were selected from a single spike to represent a sample. The seeds collected from a different spike represented a replicate biological sample.

Four biological replicate experiments for M292 and the control Himalaya were used to compare the transcription profiles in developing endosperm at the mid grain fill stage. Differentially expressed genes were identified from the median data sets of differentially expressed genes from the four microarray experiments. The stringency level used to select the genes was 1e-10. This level of stringency was determined empirically to give the least number of false positive results. From the tRMA analysis, 42 array features were identified as differentially expressed, 20 of which were up-regulated and 22 down regulated in M292 compared to Himalaya. All of the clones identified were verified by sequence analysis from both the 3 prime and 5 prime ends to ensure that the annotation of the clone was correct. These results showed that one clone was a chimera and this clone was not analyzed further. Using the sequence data, a sequence homology search was made against the TIGR (http://www.tigr.org) tentative consensus sequence (TC) data base using either the barley or wheat Gene Index, depending on the origin of the clone on the microarray. From this comparison the 41 cDNA clones could be grouped into 23 different genes. A verification of the expression changes was then undertaken by RNA blot-hybridization using one clone as a representative for each TC. The expression changes were verified using an RNA gel blot analysis in which RNA was isolated from a fifth replicate endosperm sample. The change in expression for 6 clones was not confirmed and these clones were not analyzed further.

The 17 clones which passed the quality control conditions, their TC sequence and the expression change, relative to Himalaya, for both the microarray and RNA gel blot analysis are listed in Table 2. These genes have been grouped into four categories, being carbohydrate related, defense, stress response and those genes for which a biological function has not yet been established. In Table 2, column 4 presents the microarray results (M292/Himalaya) and column 5 presents the RNA gel blot analysis results. Therefore, the numbers in these columns represent the fold change in gene expression in M292 above or below the Himalaya control. Clone pTa250 (Appels and Dvorak, 1982 (supra)) was used as a control sequence for the RNA blot hybridizations.

TABLE 2

Differentially expressed genes in M292 developing grain

| TIGR TC | GenBank ID | Name | Micro-Array | Northern |
|---|---|---|---|---|
| Carbohydrate related genes | | | | |
| 250803 | AL812383 | β-D-glucan exohydrolase | 2.33 | 4.60 |
| 250388 | BQ607866 | sucrose synthase | 2.47 | 1.25 |
| 139354 | CV054497 | serpin | 0.30 | 0.10 |
| 249933 | BQ609223 | β-amylase | 0.27 | 0.20 |
| 269042 | BQ606784 | starch synthase | 0.17 | 0.03 |

TABLE 2-continued

Differentially expressed genes in M292 developing grain

| TIGR TC | GenBank ID | Name | Micro-Array | Northern |
|---|---|---|---|---|
| Defense related gene | | | | |
| 146614 | CV055257 | alpha-amylase inhibitor BDAI-I | 0.36 | 0.53 |
| Stress protein related genes | | | | |
| 232242 | BG263730 | t.complex protein | 2.56 | 2.10 |
| 246814 | AL818443 | dnaK-type protein | 2.30 | 1.60 |
| 250385 | BG314518 | heat shock protein 80 | 2.27 | 3.22 |
| 264292 | BE442600 | heat shock protein 70 | 2.25 | 2.00 |
| 139615 | CV056993 | prohibitin | 2.04 | 1.70 |
| Genes of unassigned function | | | | |
| 246973 | BQ606826 | annexin p33 | 2.85 | 4.10 |
| 232395 | X83881 | S-adenosylmethionine decarboxylase | 2.37 | 1.30 |
| 233204 | BE444846 | Rubber elongation factor | 2.14 | 3.32 |
| 249807 | BQ608029 | O.s r40g2 protein | 2.26 | 10.00 |
| 234638 | BQ606719 | Puro/hordoindoline-a | 0.40 | 0.58 |
| 147907 | CV060362 | No Hit either blast x or n | 0.32 | 0.27 |

Interestingly, many genes known to play a role in starch biosynthesis that were represented on the microarray did not show differential expression in M292 compared to Himalaya. These were as follows (with Genbank Accession Nos.): ADP Glucose pyrophosphorylase small subunit (AL815034); ADP Glucose pyrophosphorylase large subunit (AL814437); Granule bound starch synthase I (BQ608470); Granule bound starch synthase II (BE497955); Starch synthase I (AL815975); Starch synthase III (AL811419); Starch branching enzyme I (AL816520); Starch branching enzyme IIa (AL812818); Starch branching enzyme IIb (BF201559); Isoamylase: glycogen 6-glucanohydrolase (BE422551); Alpha amylase (AL809888).

At 20 DPA in barley grain, 4 differentially expressed genes other than SSIIa were identified that have been related to the storage of carbon through sucrose uptake in the endosperm. Of these 4 genes, 2 were up regulated in M292 (β-D-glucan exohydrolase and sucrose synthase) and 2 down regulated (serpin, β-amylase and ssIIa).

The SSIIa transcript was almost undetectable by RNA gel blot analysis, being reduced to only 3% of the wild-type level. This result was consistent with the absence of SSIIa proteins in the M292 developing endosperm and mature grain as observed by Morell et al. 2003 (supra). The reduction by 97% may be a consequence of rapid turnover of the mRNA by the nonsense-mediated mRNA decay pathway. The smaller reduction of ssIIa transcript observed in the microarray experiment compared to the RNA gel blot hybridization result, may have been due to some cross hybridization of transcripts from other members of the starch synthase families. This example shows the importance of confirming results obtained from the arrays with RNA gel blot hybridization or RT-PCR experiments, as these methods can be targeted to specific members of the gene families.

The function of β-amylase in the germinating grain is to remove successive maltose units from the non reducing ends of the starch chain to provide a source of carbon, but it is also synthesized and accumulates during grain development (MacGregor et al., Cereal Chemistry, 48: 255-269, 1971). Guerin et al., Journal of Cereal Science, 15: 5-14, 1992 showed that β-amylase was present in the seed as a bound inactive complex with Protein Z (serpin) that is associated with the starch granules. In this study the transcript levels of both serpin (protein Z type) and β-amylase were reduced in the mutant line indicating that these proteins may be co-regulated in the developing grain.

The expression of sucrose synthase (SuS) was slightly up-regulated in M292 endosperm. The catalysis of sucrose and UDP to form UDP-glucose and fructose is carried out by SuS in a reversible reaction. The UDP-glucose produced by SuS can be converted via the combined action of UDP-glucose pyrophosphorylase and phosphoglucomutase to give Gluc-1-P and Gluc-6-P which can enter glycolysis or be used in starch synthesis (Winter and Huber, *Critical Reviews in Plant Sciences* 19: 31-67, 2000). Alternatively, it can provide the substrate for the synthesis of cellulose, callose, or other cell wall polysaccharides. It appears that the mutation ssIIa in M292 disrupted the utilization of sucrose for starch synthesis, associated with an increase in the level of sucrose (6.5 fold increased in M292, Table 1) and increased SuS expression.

Other sucrose regulated, or UDP-glucose utilizing enzymes were not differentially expressed in this analysis. For example, there were 11 clones present on the cDNA array relating to a range of cellulose synthase or cellulose synthase-like genes and 3 callose synthase genes, none of which were differentially expressed. However, there was a significant increase (33% on a mg per grain basis) of β-glucan content in the M292 grain and UDP-glucose is a substrate for the synthesis of this polysaccharide. While the level of fructo-oligosaccharides were greater in mature M292 grain, than in Himalaya, genes encoding enzymes of fructan biosynthesis, such as sucrose:sucrose 1-fructosyltransferase and sucrose:fructan 6 fructosyltransferase, were not differentially expressed in this comparison.

There was an increase in expression of the gene β-D-glucan exohydrolase in M292. This exohydrolase has a broad range of substrate specificity which presents a problem in assigning a specific target molecule for this enzyme. Hrmova and Fincher, *Plant Molecular Biology*, 47: 73-91, 2001 suggested the β-D-glucan exohydrolases be classified as polysaccharide exohydrolases because they can hydrolyze a range of polysaccharides and oligosaccharides. This enzyme is usually found in situations where cell wall degradation or modification is occurring (Harvey et al., *Physiologia Plantarum* 113: 108-120, 2001; Hrmova and Fincher, 2001 (supra)). A possible role for this enzyme in M292 is the degradation of those endosperm cells that are not filled in the shrunken mutant grain, or recovering/recycling glucose as proposed by Hrmova and Fincher, 2001 (supra).

Previous analysis showed that the quantities of starch branching enzymes IIa, IIb are similar in the wild type and M292 seed (Morell et al. 2003 (supra)). The observation that the protein level was unchanged is consistent with the present transcription analysis where no differential expression was observed for branching enzyme IIa or IIb.

The role of the other differentially expressed genes identified in this analysis in M292 is unknown.

In summary, in wild-type Himalaya sucrose transported into the grain can be efficiently converted to storage carbohydrates. Two major forms of the carbohydrates in Himalaya are starch (82.8% of total carbohydrate) and NSP (16.7% of total carbohydrate), with free sugar and fructan being the minor components. In M292, due to the ssIIa mutation, this process has been disrupted, leading to the reduction of total starch to 46.6% of total carbohydrate. It is proposed that the ssIIa mutation leads to the accumulation of sucrose that up-regulates the expression of SuS. The sucrose and UDP-glucose (synthesized by SuS) are then used as the substrates for the synthesis of NSP (32.5% of total carbohydrate), fructan (18.4% of total carbohydrate) and free sugar (2.6% of total carbohydrate) instead of starch. The differential expression of UDP-glucose pyrophosphorylase was not detected, although this cDNA was on the microarray.

Example 4

Determination of Fructan Content in Grain

Method for Quantification of Fructo-Oligosaccharides (Fructans)

Total sugars were extracted from wholemeal following the method of Lunn and Hatch, 1995 (supra) with the following modification. Wholemeal is defined herein as the product obtained by milling mature grain, without subsequent fractionation (e.g. sieving) to remove the bran. Therefore wholemeal contains all of the components in the grain.

The wholemeal was extracted 3 times with 10 ml of 80% ethanol (v/v) in a boiling water bath for 10 minutes. The supernatant from each extraction was pooled and freeze dried, then re-suspended in 2 ml milliQ water. The quantities of sucrose, glucose, and fructose were measured using a colorimetric microtiter plate enzymatic assay as previously described (Campbell et al., 1999 (supra); Ruuska et al., 2006 (supra)). Sugars and fructo-oligosaccharides (fructans) were also analysed by high performance anion exchange chromatography (HPAEC) as described in Ruuska et al., 2006 (supra). Both methods gave similar results.

Comparison of Fructan Contents Among Barley Varieties

Barley lines with different genetic backgrounds were used in a comparison of fructan contents. The barley lines used were: (1) lines that contain a starch synthase IIa (SSIIa) mutation (Barley M292, Barley M342 and Tantangara×292 double haploid (DH)); (2) a barley line with a waxy mutation inactivating GBBSI (Waxiro); (3) a high amylose barley (with 45% amylose, and a mutated gene(s) designated amo1); and (4) wild-type barley lines (Gardiner, Schooner, Himalaya, Sloop, Namoi and Glacier). These lines were grown at Francis, South Australia. Tantangara×292 DH is a barley line from a double haploid population from the crossing between Tantangara and Barley M292.

The results are shown in Table 3, where the fructan content represents the sum amount of glucose and fructose after hydrolysis minus the amounts of free glucose, fructose and sucrose (without hydrolysis). In a completely unexpected result, the data indicated that the barley lines containing a mutation in the SSIIa that inactivated SSIIa produced relatively high levels of fructan (shown in mg/g grain), whereas the barley lines without the SSIIa mutation produced relatively low levels of fructan. The observation was even more surprising in view of the lack of any change in the expression levels of two genes involved in fructan biosynthesis (Example 3).

TABLE 3

Analysis of fructan levels in grain of barley varieties

| Barley line | Un-hydrolysed | | | | Hydrolysed | | |
|---|---|---|---|---|---|---|---|
| | Glucose content | Fructose content | Sucrose content | Maltose content | Glucose content | Fructose content | Fructan content[a] |
| | (mg hexose equiv/g dry weight) | | | | | | |
| Barley M292 | 2.3 | 2.4 | 10.6 | 0.9 | 41.2 | 75.0 | 100.1 |
| | | | | | 49.0 | 97.9 | 130.7 |
| Gardiner | 0.6 | 0.7 | 6.5 | 0.3 | 15.9 | 28.1 | 35.8 |
| | | | | | 10.6 | 21.4 | 23.8 |
| Schooner | 0.8 | 0.8 | 7.7 | 0.5 | 19.0 | 28.2 | 37.4 |
| | | | | | 14.3 | 22.0 | 26.4 |
| Himalaya | 0.1 | 0.1 | 1.3 | 0.1 | 1.3 | 2.8 | 2.6 |
| | | | | | 1.2 | 2.5 | 2.3 |
| Waxiro | 0.7 | 0.8 | 7.1 | 0.6 | 15.8 | 21.8 | 28.3 |
| | | | | | 11.4 | 20.4 | 22.5 |
| Sloop | 0.6 | 0.6 | 7.0 | 0.4 | 10.1 | 17.4 | 18.9 |
| | | | | | 10.0 | 17.3 | 18.8 |
| Barley mutant 342 | 1.4 | 1.7 | 10.6 | 0.9 | 33.6 | 66.3 | 85.3 |
| | | | | | 42.7 | 93.8 | 121.9 |
| | | | | | 36.3 | 77.3 | 99.0 |
| Namoi | 0.6 | 0.6 | 7.0 | 0.4 | 8.7 | 16.4 | 16.5 |
| Tantangara | 0.5 | 0.5 | 7.6 | 0.3 | 10.6 | 20.1 | 21.8 |
| Tantangara × 292 DH | 1.9 | 3.2 | 11.0 | 1.0 | 41.1 | 95.4 | 119.5 |
| HA Glacier | 0.5 | 0.6 | 6.1 | 0.2 | 6.9 | 13.8 | 13.3 |
| Glacier | 0.8 | 0.7 | 5.7 | 0.5 | 7.3 | 14.3 | 14.0 |

[a]Fructan content expressed as mg/g wholemeal, which is essentially mg/g grain

The effect on fructan levels of the SSIIa mutation in different genetic backgrounds was then examined. The SSIIa mutation was transferred by backcrossing (one cross and three backcrosses, with single seed descent, equivalent to BC3F4) to two different barley varieties, namely cultivars Sloop and Tantangara. Progeny lines 250 to 374 contained the SSIIa mutation in a barley Sloop background and lines 703 to 886 had a barley Tantangara background. K4 was a black barley grain with wildtype starch, without the SSIIa mutation, grown in the same field. Total sugars were extracted from 100 mg dry weight wholemeal as described above in section 4.1.

The results are shown in Table 4, which indicated that the SSIIa mutation in both the Tantangara and Sloop barley varieties produced a high fructan content (shown in mg/g wholemeal).

TABLE 4

Comparison of fructan contents in ten selected breeding lines

| Barley lines | Un-hydrolysed | | | | Hydrolysed | | |
|---|---|---|---|---|---|---|---|
| | Glucose content | Fructose content | Sucrose content | Maltose content | Glucose content | Fructose content | Fructan content |
| | (mg hexose equiv/dry weight) | | | | | | |
| 250 | 2.3 | 2.4 | 13.4 | 1.7 | 20.2 | 48.5 | 48.9 |
| 348 | 2.6 | 2.9 | 14.9 | 1.4 | 16.7 | 43.7 | 38.6 |
| 363 | 2.3 | 2.8 | 13.3 | 1.2 | 19.9 | 49.1 | 49.4 |
| 374 | 2.5 | 3.3 | 13.9 | 1.6 | 20.0 | 52.5 | 51.2 |
| 703 | 2.2 | 2.7 | 12.9 | 1.1 | 20.5 | 54.1 | 55.6 |
| 871 | 1.8 | 2.1 | 13.5 | 1.5 | 13.2 | 41.3 | 35.6 |
| 926 | 2.3 | 3.2 | 12.7 | 1.2 | 20.3 | 52.6 | 53.4 |
| 930 | 2.1 | 2.9 | 11.9 | 1.1 | 13.9 | 48.8 | 44.6 |
| 886 | 1.5 | 2.3 | 12.9 | 1.6 | 18.6 | 46.4 | 46.6 |
| K4 | 0.4 | 0.4 | 6.7 | 0.2 | 4.2 | 8.8 | 5.2 |

Analysis of Fructan Content in SSIIa Mutant Wheat Grain

Total sugars were extracted from 100 mg dry weight wholemeal as described above in section 4.1 for a wheat SSIIa triple null mutant (mutant in the A, B and D genomes of wheat) and the corresponding wildtype wheat Sunco. These were analysed for fructan content as for the barley grain.

The results (Table 5) indicated that the wheat grain of the SSIIa triple null mutant contained increased fructan levels compared to the corresponding wild-type wheat (Sunco) grain for all growing environments, but to a varying extent. For example, comparison between grain of the SSIIa null line B63 and the wild-type line B70 indicated a 2-3 fold increase in fructan in the mutant grain. The data in Table 5 also indicated that amounts of glucose, fructose, sucrose and maltose were sometimes increased in the null wheat. The data also showed that the wheat SSIIa triple null line had less hexoses than the control line BW26, but sucrose was not significantly altered. Overall, these results indicated that an SSIIa mutation increased fructan content not only in barley, but also in wheat.

Analysis of Fructan Content in High Amylose Barley Grain

Total sugars were extracted from 100 mg dry weight wholemeal of several barley lines transgenic for SBEIIa and/or SBEIIb RNAi constructs, and wild-type barley grain of cultivar Golden Promise. Those containing the SBEIIa RNAi constructs had strongly downregulated expression of the SBEIIa gene and consequently the grain starch in these lines was elevated to about 80% amylose.

The results indicated that the transgenic barley grain containing both the SBEIIa RNAi and SBEIIb RNAi constructs (transgenic barley #22) had elevated fructan levels compared to the wildtype barley grain (Golden Promise), but the transgenic lines containing either of the single constructs, transgenic barley #20, containing the SBEIIa RNAi construct and #21, containing the SBEIIb construct, were not elevated for fructan levels in the grain.

Analysis of Fructan Content in High Amylose Wheat Grain

Total sugars were extracted from 100 mg dry weight wholemeal as described above in section 4.1 for a high amylose wheat line which was transgenic for an inhibitory SBEIIa RNAi construct and therefore elevated in amylose content to about 80% amylose (Regina et al., 2006 (supra))

TABLE 5

Analysis of fructan contents in wheat SSIIa mutant grain

| | Un-hydrolysed | | | | Hydrolysed: | | |
|---|---|---|---|---|---|---|---|
| | Glucose | Fructose | Sucrose | | | | |
| Barley lines | content (mg hexose equiv/g dry weight) | content | content | Maltose content | Glucose content | Fructose content | Fructan content |
| B29 GES 2003 | 1.17 | 1.06 | 10.08 | 1.96 | 11.35 | 25.32 | 22.39 |
| B63 GES 2003 | 0.58 | 0.52 | 13.33 | 1.64 | 17.99 | 40.14 | 42.06 |
| B70 GES 2003 wt[a] | 0.21 | 0.14 | 4.34 | 0.14 | 5.73 | 12.49 | 13.39 |
| B23/24 GES 2004 (100) | 0.33 | 0.30 | 7.84 | 0.52 | 11.36 | 24.21 | 26.58 |
| B29 GES 2004 | 0.50 | 0.38 | 10.19 | 1.48 | 9.88 | 27.63 | 24.97 |
| B63 GES 2004 | 0.68 | 0.73 | 13.10 | 1.60 | 19.78 | 45.88 | 49.55 |
| A9 GES 2004 wt | 0.54 | 0.53 | 11.78 | 0.45 | 8.48 | 19.05 | 14.24 |
| A113 GES 2004 wt | 0.75 | 0.73 | 12.02 | 1.34 | 8.54 | 19.34 | 13.03 |
| B70 GES 2004 wt | 0.14 | 0.06 | 7.86 | 0.30 | 9.49 | 22.44 | 23.57 |
| B29 Griffith 2005 | 1.53 | 1.31 | 11.36 | 1.78 | 18.22 | 38.78 | 41.01 |
| B70 Griffith 2005 wt | 1.75 | 2.93 | 2.10 | 0.29 | 6.82 | 16.56 | 16.30 |
| B29 GES 2006 | 2.51 | 2.36 | 13.42 | 2.06 | 19.40 | 37.32 | 36.38 |
| B63 GES 2006 | 1.21 | 0.98 | 16.40 | 1.09 | 23.21 | 57.98 | 61.51 |
| A113 GES 2006 wt | 0.52 | 0.45 | 7.42 | 1.00 | 8.52 | 19.52 | 18.64 |
| B70 GES 2006 wt | 0.20 | 0.11 | 4.53 | 0.00 | 10.86 | 22.66 | 28.69 |

[a]wt indicates these lines were wild-type for SSIIa

The lines used in this analysis were generated by crossing a parental SSIIa null wheat plants (SGP-1 null wheat) and wheat plants of cultivar Sunco. B29 GES 2003 and B63 GES 2003 were SSIIa mutant in all three genomes (triple nulls) and were grown at Ginninderra Experimental Station in 2003. B70 GES 2003 wt was wildtype for SSIIa and was also grown at Ginninderra Experimental Station in 2003. B23/24 GES 2004 (100), B29 GES 2004 and B63 GES 2004 were mutant for SSIIa (triple null) and were grown at Ginninderra Experimental Station in 2004. A9 GES 2004 wt, A113 GES 2004 wt and B70 GES 2004 wt were wildtype for SSIIa and were grown at Ginninderra Experimental Station in 2004. B29 Griffith 2005 was mutant for SSIIa (triple null) and was grown at Griffith in 2005. B70 Griffith 2005 wt was wildtype for SSIIa and was grown at Griffith in 2005. B29 GES 2006 and B63 GES 2006 were SSIIa mutant (triple nulls) and were grown at Ginninderra Experimental Station in 2006. A113 GES 2006 wt and B70 GES 2006 wt were wildtype for SSIIa and were grown at Ginninderra Experimental Station in 2006.

and a corresponding wildtype wheat BW26. These were analysed for fructan levels in the grain as for the barley, above. SBEIIa and SBEIIb refer to starch branching enzymes IIa and IIb, respectively.

The results indicated that high amylose wheat grain containing the SBEIIa construct (#25, #26), a transgenic wheat line containing the SBEIIb construct (#27, not elevated in amylose level) and grain of a transgenic wheat line containing an SSI RNAi construct and having reduced starch synthase I activity did not have substantially increased fructan content compared to the wild-type wheat transgenic wheat line (#28).

Effects of Growing Conditions on Fructan Content

Further experiments were carried out to determine the effects of growing conditions on the level of fructan in grain across a range of barley lines containing the SSIIa mutation.

Lines 250 to 374 and lines 703 to 926 were as described above. 2001-292: Barley M292 was grown at Ginninderra Experiment Station (GES), ACT in 2001. 2001-292: Barley M292 was grown at Forbes (NSW) in 2001. 2002-292: Barley M292 was grown at Colleambally in 2002. 2003-

292: Barley M292 was grown at Forbes in 2003. 2003-292: Barley M292 was grown at Colleambally in 2003.

The data showed that the fructan levels were elevated across a range of barley genetic backgrounds each containing the SSIIa mutation, and a variety of growing environments.

TABLE 6

Effects of growing conditions on fructan content

| Line No | Growing site | Line name | Fructan level (mg/g grain) |
|---|---|---|---|
| 2003 | Black mountain glasshouse, ACT | 250 | 107.1 |
| 2003 | Black mountain glasshouse, ACT | 266 | 53.0 |
| 2003 | Black mountain glasshouse, ACT | 348 | 59.8 |
| 2003 | Black mountain glasshouse, ACT | 363 | 115.2 |
| 2003 | Black mountain glasshouse, ACT | 374 | 98.3 |
| 2003 | Black mountain glasshouse, ACT | 703 | 174.2 |
| 2003 | Black mountain glasshouse, ACT | 871 | 99.6 |
| 2003 | Black mountain glasshouse, ACT | 886 | 126.9 |
| 2003 | Black mountain glasshouse, ACT | 926 | 103.9 |
| 2003 | Black mountain glasshouse, ACT | 930 | 164.0 |
| 2001 | Ginninderra Experimental Station, ACT | 292 | 68.9 |
| 2001 | Forbes | 292 | 76.6 |
| 2002 | Colleambally | 292 | 37.0 |
| 2003 | Forbes | 292 | 40.4 |
| 2003 | Colleambally | 292 | 42.1 |

Example 5

Large Scale Production of Fructan

Having about 10% fructan, the barley grain mutant in SSIIa can be used for the isolation and purification of fructan as well as other products such as high amylose starch and β-glucan. Such production from grain which can be readily produced in broadacre agriculture will be cost-effective relative to existing methods of fructan production, for example, involving the extraction of inulins from chicory. BarleyMax grain contained at least 5% fructan by weight, or when grown under some conditions, at least 10% fructan.

Large scale extraction of fructan can be achieved by milling the grain to wholemeal flour and then extracting the total sugars including fructans from the flour into water. This may be done at ambient temperature and the mixture then centrifuged or filtered. The supernatant is then heated to about 80° C. and centrifuged to remove proteins, then dried down. Alternatively, the extraction of flour can be done using 80% ethanol, with subsequent phase separation using water/chloroform mixtures, and the aqueous phase containing sugars and fructan dried and redissolved in water. Sucrose in the extract prepared either way may be removed enzymatically by the addition of α-glucosidase, and then hexoses (monosaccharides) removed by gel filtration to produce fructan fractions of various sizes. This would produce a fructan enriched fraction of at least 80% fructan.

Example 6

Production of Food Products

The mature grain as harvested, processed grain, wholemeal or flour obtained from the grain can be used to produce food products for consumption by humans or other mammals by any method known to persons of ordinary skill in the art. For example, wholemeal bread may be made by substituting from 15-30% (w/w) or even more of the wholemeal used in bread recipes with wholemeal from any one of the SSIIa mutant grain types described herein.

Example 7

Compositions for Treatment

A composition of purified fructan in the form of a capsule for oral treatment may be prepared by filling a standard two-piece hard gelatin capsule with 500 mg of the agent or compound, in powdered form, 100 mg of lactose, 35 mg of talc and 10 mg of magnesium stearate.

Example 8

In Vitro Fermentation Studies and Rat Feeding Trial

In vitro experiments and subsequent feeding trials in rats examined the fermentative and physiological properties of barley grain mutant 292 extracts.

In Vitro Fermentation Studies

An anaerobic static batch culture system was used to model human colonic fermentation. This simulation system is widely used internationally and yields reliable and reproducible results. Inoculum for the system was freshly voided faeces sourced from healthy adult subjects consuming their habitual diets. After collection, faecal samples were homogenised and suspended at 10% w/v in sterile anaerobic PBS.

Figure 2:
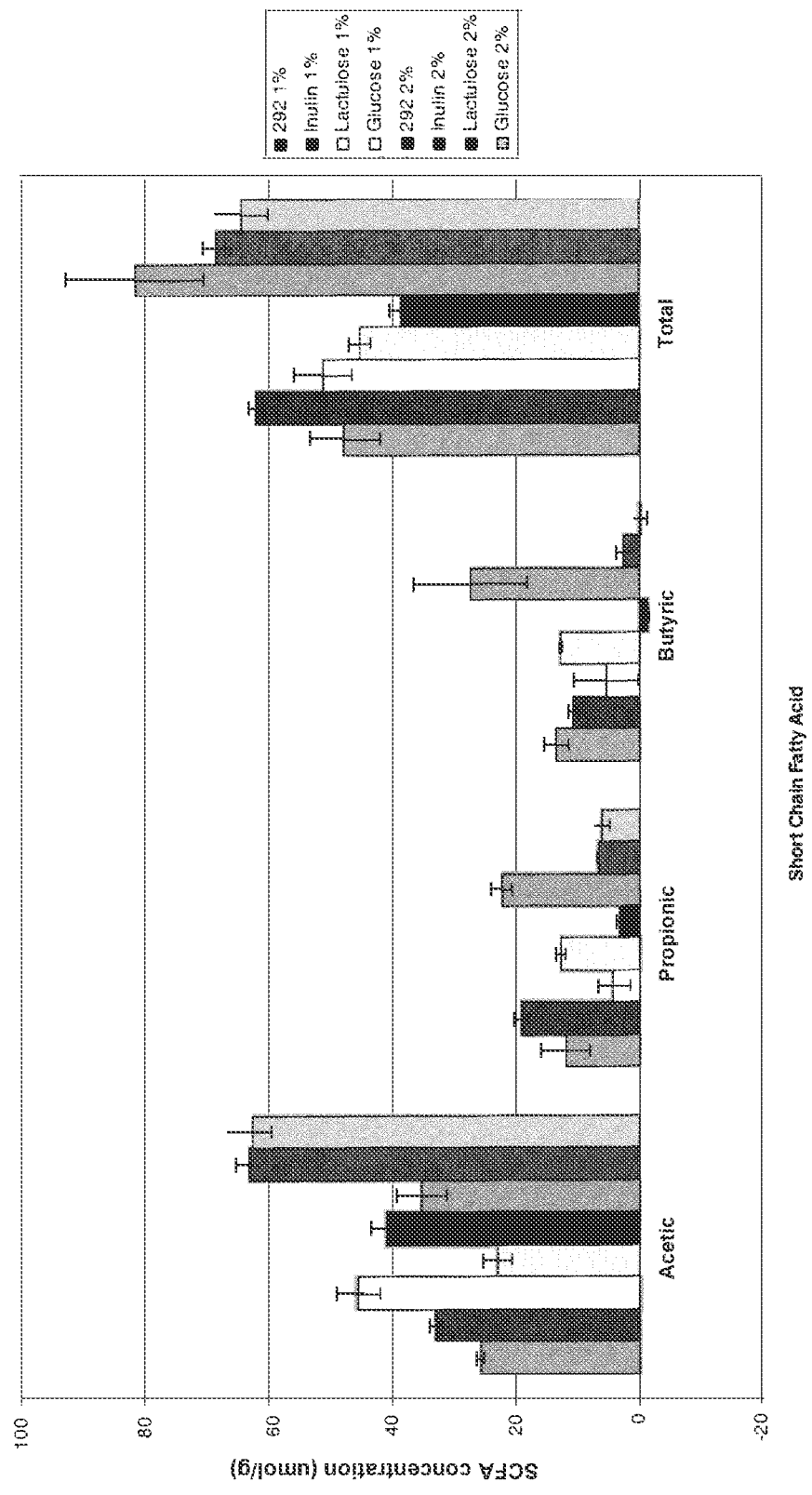
FIG. 2 is a graphical representation of data showing the fermentation properties of modified cereal products. Extract of barley grain mutant 292 and standards (inulin, lactulose, glucose) were fermented in carbon-limited fermentation media. Short chain fatty acid (SCFA) production was measured. This indicated that the lower doses of mutant 292 produced comparable fermentation to that of inulin (see total SCFA $1^{st}$ & $2^{nd}$ column (1% 292 and inulin 1%) and $5^{th}$ & $6^{th}$ column (2% 292 and Inulin 2%).

A series of studies employing a completely randomised experimental design was used to investigate the fermentative properties of novel cereal product (extracts of barley grain mutant 292). Predetermined amounts of these products were added to incubators. Reference carbohydrate substrates (glucose, lactulose and inulin), at comparable levels of addition, were included in each assay run. Quadruplicate incubations were performed in an anaerobic chamber for the cereal test products, standard substrates as well as for the Control (blank; no exogenous substrate added to the fermentor). Briefly, test products (and standards) were pre-weighed into sterile screw-capped sterile fermentation vessels and the carbon-limited fermentation media comprising carbonate buffer and macro- and micronutrients added to a achieve the predetermined volume and pH (7.0). After a period of equilibration an aliquot of inoculum was added to each fermentor. These were then capped, sealed and incubated at 37° C. with constant shaking. Incubations containing no added substrate (blank) were included in each assay run. After 24 hours, the ferments were frozen at −20° C. to await biochemical analysis using standardised procedures. Short chain fatty production (SCFA) of the test products and standards from the study are shown in FIG. 2. The results show that at the lower dosage (1%) the extracts of the barley grain mutant 292 produced a comparable fermentation pattern to that of inulin.

Rat Feeding Trial

The rat study was designed to corroborate and extend the findings of the in vitro fermentation experiments. Such techniques are capable of providing only preliminary information as they are clearly unable to fully simulate the complex physical, microbial and chemical processes that occur along the gastrointestinal tract.

The primary aim of the study was to investigate the fermentation properties of extracts of barley grain mutant 292 stem. These novel products were compared against a negative control and an established (commercial) prebiotic.

The study comprised a completely randomised design involving 5 dietary treatment groups with 10 rats per group. The treatments were:

Negative control (basal diet containing no additional fibre); Barley grain mutant 292 extract, included at 2% and 5% (by weight) of the diet.

Positive controls: commercial oligofructose at 2% and 5% of the diet.

The major experimental endpoints were cecal SCFA concentrations and pools.

Briefly, rats (approximately 200 g live weight) were acclimatised for 7 days before being assigned randomly to treatment groups. A non-purified commercial chow was fed during the adaptation phase and treatment diets were fed for the subsequent 2 weeks of study. Rats were maintained in wire-based cages except for the final 4 days of study when they were kept in metabolic cages to enable record daily feed and water intakes, and fecal and urine output, of individual animals. Rats had unrestricted access to diets and drinking water throughout the study.

At the end of the treatment period rats were anaesthetized and various samples, including intestinal contents, collected and stored to await biochemical analysis using standardized laboratory techniques.

The diets that were fed were based on the AIN-93G formulation and as such comprised a uniform composition of macronutrients and fibre as NSP (at ~15% w/w). A vitamin and mineral mixture added to ensure that all diets were nutritionally complete. Four of the 5 diets contained oligosaccharide extracts from barley or chicory added at either 2% or 5% (by weight of diet).

Figure 3:
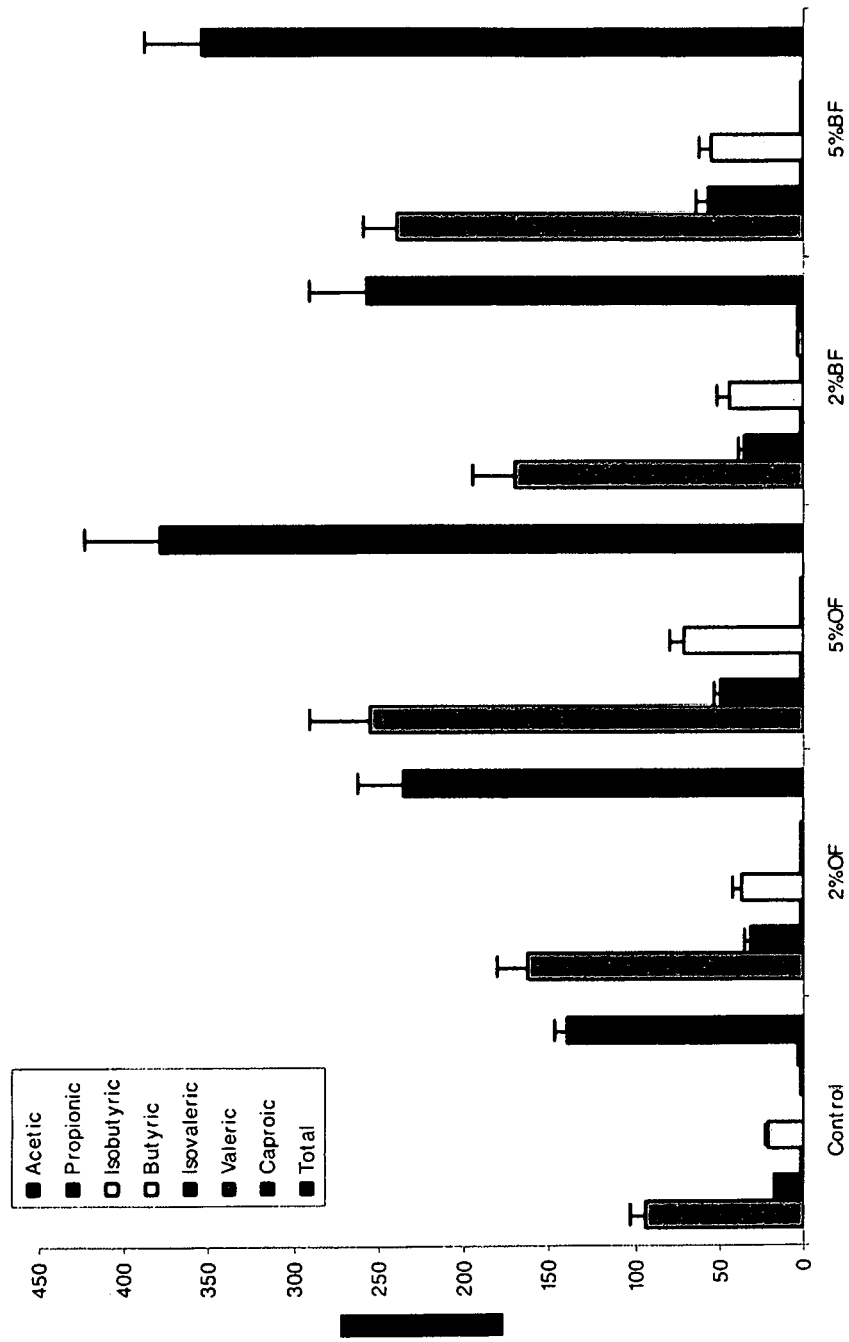
FIG. 3 is a graphical representation of data showing in vivo effect in rats of a diet including barley grain 292 compared to corresponding oligofructose standards and controls. The total amount of short chain fatty acids and acidification of caecal digesta was greater for treatments than controls and barley grain 292 produced comparative results to those of oligofructose standards. Items in key for SCFA types running top to bottom correspond to columns of bar graph for each treatment running from left to right.

Results:

Food intake was similar among treatment groups, although final live weights were greater for all treatment groups compared to the control. Fecal output was greater for all treatment groups relative to controls and related positively to level of dietary inclusion of the various extracts. Treatment differences in caecal digesta weight mirrored those for faecal output. Consumption of treatment extracts was associated with acidification of caecal digesta. FIG. 3 shows caecal pools of individual and total SCFA. The total amount of SCFA was greater for the treatments compared to controls, and the responses to barley grain extract (at the corresponding level of dietary inclusion) were comparable to those of oligofructose. In summary, the barley grain mutant 292 extracts produced comparable results to those of the corresponding oligofructose standards.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 7

Summary of sequence identifiers

| SEQUENCE ID NO: | DESCRIPTION |
|---|---|
| 1 | *Hordeum vulgare* subsp. *vulgare* starch synthase II mRNA, complete cDNA sequence. Accession No. AY133249, 2972 nucleotides, protein coding region: nucleotides 114-2522, on chromosome 7 of barley. |
| 2 | amino acid sequence of starch synthase II encoded by SEQ ID NO: 1; 802 amino acids |
| 3 | *Triticum aestivum* starch synthase IIa mRNA, complete cDNA sequence, Accession No. AF155217. 2842 nucleotides, protein coding region: nucleotides 89-2488 Reference: Li et al., *Plant Physiol.* 120: 1147-1156, 1999. |
| 4 | amino acid sequence of starch synthase IIa encoded by SEQ ID NO: 3: 799 amino acids |
| 5 | *Triticum aestivum* cDNA sequence for starch synthase IIa-2 (wSSIIa-2 gene). Accession No. AJ269503. 2780 nucleotides, protein coding region: nucleotides 55-2454; mature peptide: nucleotides 230-2451 Reference: Gao and Chibbar, *Genome* 43: 768-775, 2000. |
| 6 | *Triticum aestivum* amino acid sequence encoded by wSSIIa gene for starch synthase IIa (EC. 2.4.1.21), precursor 799 amino acids. |
| 7 | *Triticum aestivum* wSSIIa-B gene for starch synthase IIa, genomic sequence from B genome, Accession No. AB201446, exons: 246-506, 611-1316, 1407-1471, 2287-2364, 2454-2564, 2662-2706, 3085-3258, 5855-6811. Reference: Shimbata et al., *Theor. Appl. Genet.* 111: 1072-1079, 2005. |
| 8 | amino acid sequence of SSIIa-B encoded by SEQ ID NO: 7: 798 amino acids |
| 9 | *Triticum aestivum* wSSIIa-D gene for starch synthase IIa-D, predicted amino acid sequence, Accession No. AB201447: 799 amino acids |
| 10 | *Sorghum bicolor* starch synthase IIa complete cDNA sequence, Accession No. EU620718, 2400 nucleotides, protein coding region: 31-2262 |
| 11 | amino acid sequence encoded by nucleotides 31 to 2262 of SEQ ID NO: 10 |
| 12 | *Oryza sativa* mRNA for starch synthase IIa, complete cDNA sequence, Accession No. AB115918, 2433 nucleotides, protein coding region: 1-2433. Reference: Nakamura et al., *Plant Mol. Biol.* 58: 213-227, 2005. |
| 13 | amino acid sequence encoded by nucleotides 1 to 2432 of SEQ ID NO: 12: 810 amino acids |
| 14 | *Zea mays* ZmSSIIa mRNA sequence, Accession No: BT023979, 2248 nucleotides Reference: Lai et al., *Genome Res.* 14: 1932-1937, 2004. |
| 15 | *Oryza sativa* SSIIb sequence of cDNA clone: Accession No. AK066446, 2645 nucleotides, Reference: Yamakawa et al., *Plant Physiol* 144: 258-277, 2007. |
| 16 | *Oryza sativa* soluble starch synthase II-2 mRNA, complete cDNA sequence, Accession No. AF395537, 2394 nucleotides, protein coding region: nucleotides 34-2118. |
| 17 | amino acid sequence encoded by nucleotide of 34-2118 of SEQ ID NO: 16. Accession No. AAK81729, 694 amino acids |
| 18 | *Triticum aestivum* starch synthase IIb precursor, cDNA sequence, 2025 nucleotides Accession No. EU333947, protein coding region: 1-2025. |
| 19 | amino acid sequence encoded by nucleotide 1 to 2025 of SEQ ID NO: 18: 674 amino acids |
| 20 | *Sorghum bicolor* starch synthase IIb precursor, mRNA, complete cDNA sequence, Accession No. EU620719, 2302 nucleotides, protein coding region: 36-2150. |
| 21 | amino acid sequence encoded by nucleotide 1 to 2025 of SEQ ID NO: 20: 704 amino acids |
| 22 | *Zea mays* starch synthase IIb- precursor, mRNA, complete cDNA sequence, Accession No. EF472249, protein coding region nucleotides 74-2188, 2569 nucleotides |
| 23 | amino acid sequence encoded by nucleotide 1 to 2025 of SEQ ID NO: 22: 704 amino acids |

TABLE 8

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

TABLE 9

Exemplary and Preferred Amino Acid Substitutions

| Original Residue | EXEMPLARY SUBSTITUTIONS | PREFERRED SUBSTITUTIONS |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

BIBLIOGRAPHY

Adams et al., *Anal. Biochem.*, 266: 77-84, 1999
Almeida and Allshire, *Trends Cell Biol.* 15: 251-258, 2005
Altschul et al., *Nucleic Acids Res.* 25: 3389, 1997
An, *Methods in Enzymology*, 153: 292, 1987
Appels and Dvorak, *Theoretical and Applied Genetics*, 63: 337-348, 1982
Ausubel et al., (eds.), *Current Protocols in Molecular Biology*, John Wiley & Sons, NY, 6.3.1-6.3.6., 1989
Ausubel et al., *Current Protocols in Molecular Biology*, John Wiley & Sons Inc, Chapter 15, 1994-1998
Barker et al., *Plant Mol. Biol.*, 2: 235-350, 1983
Batey et al., *J. Sci. Food Agric.* 74: 503-508, 1997
Bechtold et al., *C.R. Acad. Sci. Paris*, 316: 1194, 1993
Bernfeld, In: Colowick S, Kaplan N (eds), *Methods in enzymology*. Academic, NY, p 149, 1955
Bevan et al., *Nucl. Acid Res.*, 11: 369, 1983
Birch, *Ann Rev Plant Physiol Plant Mol Biol.* 48: 297-326, 1997
Bird et al. *Br. J. Nutr.* 92: 607-615, 2004b
Bird et al., *J. Nutr.* 134: 831-835, 2004a
Bourque, *Plant Sci.* 105: 125-149, 1995
Boyer and Preiss, *Carbohydrate Research*, 61: 321-334, 1978
Buléon et al., *International Journal of Biological Macromolecules*, 23: 85-112, 1998
Campbell et al., *Journal of the science of food and agriculture* 79: 232-236, 1999
Cao et al., *Archives of Biochemistry and Biophysics*, 373: 135-146, 2000
Cao et al., *Plant Physiol.* 120: 205-215, 1999
Christensen et al., *Transgen. Res.*, 5: 213-218, 1996
Clarke and Rahman, *Theoretical and Applied Genetics*, 110: 1259-1267, 2005
Comai et al., *Plant J.* 37: 778-786, 2004
Craig et al., *Plant Cell* 10: 413-426, 1998
De Framond, *Biotechnology*, 1: 262, 1983
Deikman et al., *EMBO J.*, 2: 3315-3320, 1998
DellaPenna et al., *Plant Cell*, 1: 53-63, 1989
Eagles et al., *Aust. J. Agric. Res.* 52: 1 349-1356, 2001
Fincher and Stone, *Advances in Cereal Science and Technol* 8: 207-295, 1986
Fromm et al., *Proc. Natl. Acad. Sci. U.S.A.* 82: 5824, 1985
Gao and Chibbar, *Genome* 43: 768-775, 2000
Gao et al., *Plant Cell*, 10: 399-412, 1998
Garfinkel et al., *Cell*, 27: 143-153, 1983
Greve, *J. Mol. Appl. Genet.*, 1: 499-511, 1983
Guerin et al., *Journal of Cereal Science*, 15: 5-14, 1992
Harayama, *Trends Biotechnol.* 16: 76-82, 1998
Hartmann and Endres, *Manual of Antisense Methodology*, Kluwer, 1999
Harvey et al., *Physiologia Plantarum* 113: 108-120, 2001
Haseloff and Gerlach, *Nature* 334: 585-591, 1988
Hedman and Boyer, *Biochemical Genetics*, 20: 483-492, 1982
Hellwege et al., *Proc. Natl. Acad. Sci. U.S.A.* 97: 8699-8704, 2000
Hendrix et al., *J. Insect Physiol.*, 47: 423-432, 2001
Henikoff et al., *Plant Physiol.* 135: 630-636, 2004
Henry and Saini, *Cereal Chem.* 66: 362-365, 1989
Hinchee et al., *Biotech.* 6: 915, 1988
Hoekema et al., *Nature*, 303: 179, 1983
Hrmova and Fincher, *Plant Molecular Biology*, 47: 73-91, 2001
James et al., *Plant Cell*, 7: 417-429, 1995
Joshi, *Nucl. Acid Res.* 15: 6643, 1987
Kaur and Gupta, *J. Biosci.* 27: 703-714, 2002
Khandjian, Bio/Technology, 5: 165-167, 1987
Klein et al., *Nature*, 327: 70, 1987
Konik-Rose et al. *Starch/die Stärke* 53:14-20, 2001
Kubo et al., *Plant Physiology*, 121: 399-409, 1999
Lai et al., *Genome Res.* 14: 1932-1937, 2004
Langridge et al., *Aust. J. Agric. Res.* 52: 1043-1077, 2001
Lemieux, *Current Genomics*, 1: 301-311, 2000.
Li et al., *Plant Physiology*, 120: 1147-1155, 1999a
Li et al., *Plant Physiology*, 123: 613-624, 2000
Li et al., *Theoretical and Applied Genetics*, 98: 1208-1216, 1999b
Libessart et al. *Plant Cell* 7(8): 1117-1127, 1995
Lunn and Hatch, *Planta* 197: 385-391, 1995
MacGregor et al., *Cereal Chemistry*, 48: 255-269, 1971
McPherson and Moller (Ed), BIOS Scientific Publishers Ltd, Oxford, 2000
Medberry et al., *Plant Cell*, 4: 185-192, 1992
Medberry et al., *Plant* 3: 619-626, 1993
Millar and Waterhouse, *Funct Integr Genomics*, 5: 129-135, 2005
Mizuno et al., *Journal of Biochemistry*, 112: 643-651, 1992
Morell et al., *Electrophoresis*, 19: 2603-2611, 1998
Morell et al., *Plant* 34: 173-185, 2003
Moshfegh et al., *J Nutr.* 129 (Suppl): 1407S-11S, 1999

Myers et al., *Plant Physiology*, 122: 989-997, 2000
Nakamura et al., *Plant Mol. Biol.* 58: 213-227, 2005
Needleman and Wunsch, *J. Mol. Biol.* 48: 443-453, 1970
Niedz et al., *Plant Cell Reports*, 14: 403, 1995
Ow et al., *Science*, 234: 856, 1986
Pasquinelli et al., *Curr Opin Genet Develop* 15: 200-205, 2005
Perriman et al., *Gene*, 113: 157-163, 1992
Potrykus et al., *Mol. Gen. Genet.* 199: 183, 1985
Prasher et al., *Biochem. Biophys. Res. Comm.* 126: 1259-68, 1985
Prosky et al., *J Assoc Off Agric Chem* 68: 677, 1985
RACI, Method 02-03, 2003
Regina et al., *Proc. Natl. Acad. Sci. U.S.A.* 103: 3546-3551, 2006
Remington's Pharmaceutical Sciences, 18$^{th}$ Ed. Mack Publishing, Company, Easton, Pa., U.S.A., 1990
Ritsema and Smeekens, *Curr. Opin. Plant Biol.* 6: 223-230, 2003
Robinson, *The Organic Constituents of Higher Plants*, Cordus Press, North Amherst, USA, 1980
Ruuska et al., *Functional Plant Biology* 33: 799-809, 2006
Salomon et al., *EMBO J.*, 3: 141-146, 1984
Sambrook et al., *Molecular Cloning: A Laboratory Manual* (2nd ed.). Cold Spring Harbour Laboratory, Cold Spring Harbour, N Y, 1989
Schenk et al., *Proc. Natl. Acad. Sci. U.S.A.* 97: 11655-11660, 2000
Schnyder, *New Phytol* 123: 233-245, 1993
Schulman and Kammiovirta, *Starch*, 43: 387-389, 1991
Senior, Biotech. *Genet. Engin. Revs.* 15: 79-119, 1998
Sevenier et al., *Nature Biotechnol.* 16: 843-846, 1998
Sharp et al., *Aust Agric Res* 52: 1357-1366, 2001
Shimamoto et al., *Nature*, 338: 274-276, 1989
Shimbata et al., *Theor. Appl. Genet.* 111: 1072-1079, 2005
Shippy et al., *Mol. Biotech.* 12: 117-129, 1999
Slade and Knauf, *Transgenic Res.* 14: 109-115, 2005
Smith et al., *Nature*, 407: 319-320, 2000
Stalker et al., *Science*, 242: 419, 1988
Sun et al., *The New Phytologist*, 137: 215-215, 1997
Theander et al., *J AOAC Int* 78: 1030-1044, 1995
Thillet et al., *J. Biol. Chem.* 263: 12500, 1988
Thompson et al., *Carbohydrate Res.*, 331: 149-161, 2001
Tingay et al., *Plant J.* 11: 1369-1376, 1997
Topping et al., *Starch/Stärke* 55: 539-545, 2003
Tsuchiya et al., *Physiologia Plantarum* 125: 181-191, 2005
Tungland and Meyer, *Comprehensive Reviews in Food Science and Food Safety*, 2: 73-77, 2002
Van den Ende et al., *Plant Physiol.* 131(2): 621-631, 2003
Veronese et al., *Enz. Microbial Tech.*, 24: 263-269, 1999
Wan and Lemaux, *Plant Physiol.* 104: 37-48, 1994
Waterhouse et al., *Proc. Natl. Acad. Sci. U.S.A.* 95: 13959-13964, 1998
White and Secor, *Arch Biochem Biophys.* 44: 244-5, 1953
Wilson et al., *Bioinformatics* 19: 1325-1332, 2003
Winter and Huber, *Critical Reviews in Plant Sciences* 19: 31-67, 2000
Yamakawa et al., *Plant Physiol* 144: 258-277, 2007
Yamamori et al., *Theor. Appl. Genet.* 101: 21-29, 2000
Zwar and Chandler, *Planta* 197: 39-48, 1995.

The invention claimed is:

1. A method of identifying a variety of wheat grain which has increased levels of fructan comprising:

(i) obtaining wheat grain of a mutant hexaploid wheat plant grown in a field, wherein said wheat grain has a reduced level or activity of an endogenous starch synthase (SSII) polypeptide relative to grain from a wild-type wheat plant grown under the same environmental conditions as the mutant hexaploid wheat plant, wherein said wheat grain is homozygous for null alleles of an SSII gene in each of the A, B, and D genomes, wherein the homozygous alleles of the SSII gene of one or more of the A, B, and/or D genome(s) comprises a single base-pair substitution, insertion, or deletion;

(ii) determining the amount of fructan in the wheat grain; and (iii) if the wheat grain comprises at least 3% fructan as a percentage of the wheat grain weight, selecting the wheat grain.

* * * * *

SEQUENCE LISTING

```
<160> NUMBER OF SEQ ID NOS: 23

<210> SEQ ID NO 1
<211> LENGTH: 2973
<212> TYPE: DNA
<213> ORGANISM: Hordeum vulgare

<400> SEQUENCE: 1
tcctcgaggt gcgtttaccc cacacagagt acactccaac tccagtccaa tccagcccac      60
tgccgcttct gcccgcccat cgtaccgtcg cccgcccga tccggccgc cgccatgtcg       120 tcggcggtcg cgtccccgc gtccttcctc gcgctcgcgt ccgcctcgcc cgggagatca      180
tcacggagga gggcgagggt gggcgcgtcg ccaacccgcg ctggggccgg caggctgcaa     240
tggcggccgt cgccgctgca gcgcacggct cgcgacggag cggtggccgc gcgcgccgcc     300
gggatcgacg acgccgcgcc cggtaggcag ccccgcgctc gccgctatgg cgccgccacc     360
aaggtcgcgg atcccgtcaa gacgctcgat cgcgacgccg cggaaggtgg tgggccgtcc     420
ccgccggcac cgaggcagga cgccgcccgt ctgccgagta agaacggcac gctgatcaac     480
ggtgagaaca aacctaccgg cggcggtggc gcgactaaag acagcgggct gcccacaccc     540
gcacgcgcgc cccatctgtc aatccagaac agagtaccgg tgaacggtga aaacaaacat     600
aaggtcgcct cgccgccgac cagcatagtg gatgtcgcgt ctccggggttc cgcagctaac     660 atttccatca gtaacaaggt gccgccgtcc gttgtcccag ccaagaagac gccgccgtcg     720
tccgttttcc cggccaagaa gacgctgccg tcgtccggct caaattttgt gtcctcggcc     780
tctgctccca ggctggacac tgtcagcgat gtggaacttg cacagaagaa ggatgcgctg     840
attgtcaaag aagctccaaa accaaggct ctttcggccc ctgcagcccc cgctgtacaa       900
gaagaccttt gggatttcaa gaaatacatt ggtttcgagg agcccgtgga ggccaaggat      960
```

```
gatggctcgg ctgttgcaga tgatgcgggt tcctttgaac atcaccagaa tcatgattcc    1020
ggacctttgg caggggagaa cgtcatgaac gtggtcgtcg ttgctgctga atgttctccc    1080
tggtgcaaaa caggtggtct tggagatgtt gcgggtgctt tgcccaaggc tttggctaag    1140
agaggacatc gtgttatggt tgtggtacca aggtatgggg actatgagga agcctacgat    1200
gtcggagtcc gaaaatacta caaggctgct ggacaggata tggaagtgaa ttatttccat    1260
gcttatatcg atggagtgga ttttgtgttc attgacgctc ctctcttccg acaccgtcag    1320
caagacattt atgggggcag cagacaggaa attatgaagc gcatgatttt gttctgcaag    1380
gccgctgtcg aggttccttg cacgttcca tgcggcggtg tcccttacgg ggatggaaat    1440
ctggtcttca ttgcaaatga ttggcacacg gcactcctgc ctgtctatct gaaagcatat    1500
tacagggacc atggtttgat gcaatacagt cgctccgtta tggtgataca taacatcgct    1560
caccagggcc gtggccctgt agatgaattc ccgttcaccg agttgcctga gcactacctg    1620
gaacacttca gactgtacga ccccgtcggc ggtgagcacg ccaactactt cgccgccggc    1680
ctgaagatgg cggaccaggt tgtcgtcgtg agccccgggt acctgtggga gctgaagacg    1740
gtggagggcg gctgggggct tcacgacatc atacggcaga acgactggaa gacccgcggc    1800
atcgtgaacg gcatcgacaa catggagtgg aaccctgagg tggacgtcca cctgaagtcg    1860
gacggctaca ccaacttctc cctgaagacg ctggactccg gcaagcggca gtgcaaggag    1920
gccctgcagc gcgagctggg gctgcaggtc cgcggcgacg tgccgctgct cgggttcatc    1980
gggcggctgg acgggcagaa gggcgtggag atcatcgcgg acgcgatgcc ctggatcgtg    2040
agccaggacg tgcagctggt gatgctgggc acggggcgcc acgacctgga gagcatgctg    2100
cagcacttcg agcgggagca ccacgacaag gtgcgcgggt gggtgggatt ctccgtgcgc    2160
ctggcgcacc ggatcacggc gggcgccgac gcgctcctca tgccctcccg gttcgagccg    2220
tgcgggctga accagctcta cgcgatggcc tacggcacca tccctgtcgt gcacgccgtc    2280
ggcggcttga gggataccgt gccgccgttc gaccccttca ccactccgg gctcgggtgg    2340 acgttcgacc gcgccgaggc gcacaagctg atcgaggcgc tcgggcactg cctccgcacc    2400
taccgggacc acaaggagag ctggaggggc ctccaggagc gcggcatgtc gcaggacttc    2460
agctgggaac atgccgccaa gctctacgag gacgtcctcg tccaggccaa gtaccagtgg    2520
tgaacgctgc tacccggtcc agccccgcat gcgtgcatga ggatgcgaa atgcgcattg    2580 cgcacttgca gatttggcgc acgcaggaac gtgccgtcct tcttgatgag aacgccggca    2640
tccgcgaggt tgagacgctg attccgatct ggtccgtcgc agagtagagt gaaacgctcc    2700
ttgttgcagg tatatgggaa tgttttttttt ccttttttttt tgcgagggag gtatatggga    2760
atgttaactt ggtattgtaa tgtggtatgc tgtgtgcatt attacatcgg ttgttgttgc    2820
ttattcttgc tagctaagtc ggaggccaag agcgaaagct agctcacatg tctgatgtat    2880
gcaagtgaca tggttggttt ggttgtgcag tgcaaacggc aggaatggga agtgaattcc    2940
tccctgctta aattaaaaaa aaaaaaaaaa aaa                                 2973
```

<210> SEQ ID NO 2
<211> LENGTH: 802
<212> TYPE: PRT
<213> ORGANISM: Hordeum vulgare

<400> SEQUENCE: 2

Met Ser Ser Ala Val Ala Ser Pro Ala Ser Phe Leu Ala Leu Ala Ser
1               5                   10                  15

```
Ala Ser Pro Gly Arg Ser Arg Arg Ala Arg Val Gly Ala Ser
         20              25              30

Pro Thr Arg Ala Gly Ala Gly Arg Leu Gln Trp Arg Pro Ser Pro Leu
     35              40              45

Gln Arg Thr Ala Arg Asp Gly Ala Val Ala Ala Arg Ala Ala Gly Ile
 50              55              60

Asp Asp Ala Ala Pro Gly Arg Gln Pro Arg Ala Arg Arg Tyr Gly Ala
 65              70              75              80

Ala Thr Lys Val Ala Asp Pro Val Lys Thr Leu Asp Arg Asp Ala Ala
             85              90              95

Glu Gly Gly Gly Pro Ser Pro Ala Pro Arg Gln Asp Ala Ala Arg
             100             105             110

Leu Pro Ser Lys Asn Gly Thr Leu Ile Asn Gly Glu Asn Lys Pro Thr
         115             120             125

Gly Gly Gly Gly Ala Thr Lys Asp Ser Gly Leu Pro Thr Pro Ala Arg
 130             135             140

Ala Pro His Leu Ser Ile Gln Asn Arg Val Pro Val Asn Gly Glu Asn
145             150             155             160

Lys His Lys Val Ala Ser Pro Pro Thr Ser Ile Val Asp Val Ala Ser
                 165             170             175

Pro Gly Ser Ala Ala Asn Ile Ser Ile Ser Asn Lys Val Pro Pro Ser
             180             185             190

Val Val Pro Ala Lys Lys Thr Pro Pro Ser Ser Val Phe Pro Ala Lys
         195             200             205

Lys Thr Leu Pro Ser Ser Gly Ser Asn Phe Val Ser Ser Ala Ser Ala
     210             215             220

Pro Arg Leu Asp Thr Val Ser Asp Val Glu Leu Ala Gln Lys Lys Asp
225             230             235             240

Ala Leu Ile Val Lys Glu Ala Pro Lys Pro Lys Ala Leu Ser Ala Pro
             245             250             255

Ala Ala Pro Ala Val Gln Glu Asp Leu Trp Asp Phe Lys Lys Tyr Ile
         260             265             270

Gly Phe Glu Glu Pro Val Glu Ala Lys Asp Asp Gly Ser Ala Val Ala
     275             280             285

Asp Asp Ala Gly Ser Phe Glu His His Gln Asn His Asp Ser Gly Pro
290             295             300

Leu Ala Gly Glu Asn Val Met Asn Val Val Val Ala Ala Glu Cys
305             310             315             320

Ser Pro Trp Cys Lys Thr Gly Gly Leu Gly Asp Val Ala Gly Ala Leu
             325             330             335

Pro Lys Ala Leu Ala Lys Arg Gly His Arg Val Met Val Val Pro
         340             345             350

Arg Tyr Gly Asp Tyr Glu Glu Ala Tyr Asp Val Gly Val Arg Lys Tyr
     355             360             365

Tyr Lys Ala Ala Gly Gln Asp Met Glu Val Asn Tyr Phe His Ala Tyr
     370             375             380

Ile Asp Gly Val Asp Phe Val Phe Ile Asp Ala Pro Leu Phe Arg His
385             390             395             400

Arg Gln Gln Asp Ile Tyr Gly Gly Ser Arg Gln Glu Ile Met Lys Arg
             405             410             415

Met Ile Leu Phe Cys Lys Ala Ala Val Glu Val Pro Trp His Val Pro
         420             425             430
```

| | | | | | | | | | | | |
|---|---|---|---|---|---|---|---|---|---|---|---|
|Cys|Gly|Gly|Val|Pro|Tyr|Asp|Gly|Asn|Leu|Val|Phe|Ile|Ala|Asn|
| |435| | | |440| | | |445| | |

Cys Gly Gly Val Pro Tyr Asp Gly Asn Leu Val Phe Ile Ala Asn
        435                 440                 445

Asp Trp His Thr Ala Leu Leu Pro Val Tyr Leu Lys Ala Tyr Tyr Arg
450                 455                 460

Asp His Gly Leu Met Gln Tyr Ser Arg Ser Val Met Val Ile His Asn
465                 470                 475                 480

Ile Ala His Gln Gly Arg Gly Pro Val Asp Glu Phe Pro Phe Thr Glu
                485                 490                 495

Leu Pro Glu His Tyr Leu Glu His Phe Arg Leu Tyr Asp Pro Val Gly
                500                 505                 510

Gly Glu His Ala Asn Tyr Phe Ala Ala Gly Leu Lys Met Ala Asp Gln
                515                 520                 525

Val Val Val Ser Pro Gly Tyr Leu Trp Glu Leu Lys Thr Val Glu
530                 535                 540

Gly Gly Trp Gly Leu His Asp Ile Ile Arg Gln Asn Asp Trp Lys Thr
545                 550                 555                 560

Arg Gly Ile Val Asn Gly Ile Asp Asn Met Glu Trp Asn Pro Glu Val
                565                 570                 575

Asp Val His Leu Lys Ser Asp Gly Tyr Thr Asn Phe Ser Leu Lys Thr
                580                 585                 590

Leu Asp Ser Gly Lys Arg Gln Cys Lys Glu Ala Leu Gln Arg Glu Leu
                595                 600                 605

Gly Leu Gln Val Arg Gly Asp Val Pro Leu Leu Gly Phe Ile Gly Arg
        610                 615                 620

Leu Asp Gly Gln Lys Gly Val Glu Ile Ile Ala Asp Ala Met Pro Trp
625                 630                 635                 640

Ile Val Ser Gln Asp Val Gln Leu Val Met Leu Gly Thr Gly Arg His
                645                 650                 655

Asp Leu Glu Ser Met Leu Gln His Phe Glu Arg Glu His His Asp Lys
                660                 665                 670

Val Arg Gly Trp Val Gly Phe Ser Val Arg Leu Ala His Arg Ile Thr
        675                 680                 685

Ala Gly Ala Asp Ala Leu Leu Met Pro Ser Arg Phe Glu Pro Cys Gly
        690                 695                 700

Leu Asn Gln Leu Tyr Ala Met Ala Tyr Gly Thr Ile Pro Val Val His
705                 710                 715                 720

Ala Val Gly Gly Leu Arg Asp Thr Val Pro Pro Phe Asp Pro Phe Asn
                725                 730                 735

His Ser Gly Leu Gly Trp Thr Phe Asp Arg Ala Glu Ala His Lys Leu
                740                 745                 750

Ile Glu Ala Leu Gly His Cys Leu Arg Thr Tyr Arg Asp His Lys Glu
                755                 760                 765

Ser Trp Arg Gly Leu Gln Glu Arg Gly Met Ser Gln Asp Phe Ser Trp
770                 775                 780

Glu His Ala Ala Lys Leu Tyr Glu Asp Val Leu Val Gln Ala Lys Tyr
785                 790                 795                 800

Gln Trp

<210> SEQ ID NO 3
<211> LENGTH: 2842
<212> TYPE: DNA
<213> ORGANISM: Triticum aestivum

<400> SEQUENCE: 3

| | | |
|---|---|---|
| gctgccacca cctccgcctg cgccgcgctc tgggcggagg accaacccgc gcatcgtacc | 60 | |
| atcgcccgcc ccgatcccgg ccgccgccat gtcgtcggcg gtcgcgtccg ccgcgtcctt | 120 | |
| cctcgcgctc gcctccgcct cccccgggag atcacgcagg cgggcgaggg tgagcgcgcc | 180 | |
| gccaccccac gccggggccg gcaggctgca ctggccgccg tggccgccgc agcgcacggc | 240 | |
| tcgcgacgga ggtgtggccg cgcgcgccgc cgggaagaag gacgcgaggg tcgacgacga | 300 | |
| cgccgcgtcc gcgaggcagc cccgcgcacg ccgcggtggc gccgccacca aggtcgcgga | 360 | |
| gcggagggat cccgtcaaga cgctcgatcg cgacgccgcg gaaggtggcg cgccggcacc | 420 | |
| gccggcaccg aggcaggacg ccgcccgtcc accgagtatg aacggcacgc cggtgaacgg | 480 | |
| tgagaacaaa tctaccggcg gcggcggcgc gaccaaagac agcgggctgc ccgcacccgc | 540 | |
| acgcgcgccc catccgtcga cccagaacag agtaccagtg aacggtgaaa acaaagctaa | 600 | |
| cgtcgcctcg ccgccgacga gcatagccga ggtcgtggct ccggattccg cagctaccat | 660 | |
| ttccatcagt gacaaggcgc cggagtccgt tgtcccagcc gagaagccgc cgccgtcgtc | 720 | |
| cggctcaaat ttcgtggtct cggcttctgc tcccaggctg acattgaca gcgatgttga | 780 | |
| acctgaactg aagaagggtg cggtcatcgt cgaagaagct ccaaacccaa aggctctttc | 840 | |
| gccgcctgca gcccccgctg tacaagaaga ccttttggac ttcaagaaat acattggctt | 900 | |
| cgaggagccc gtggaggcca aggatgatgg ctgggctgtt gcagatgatg cgggctcctt | 960 | |
| tgaacatcac cagaaccatg attccggacc tttggcaggg gagaacgtca tgaacgtggt | 1020 | |
| cgtcgtggct gctgaatgtt ctccctggtg caaaacaggt ggtcttggag atgttgccgg | 1080 | |
| tgctttgccc aaggctttgg cgaagagagg acatcgtgtt atggttgtgg taccaaggta | 1140 | |
| tgggactat gaggaagcct acgatgtcgg agtccgaaaa tactacaagg ctgctggaca | 1200 | |
| ggatatggaa gtgaattatt tccatgctta tatcgatgga gttgattttg tgttcattga | 1260 | |
| cgctcctctc ttccgacacc gccaggaaga catttatggg ggcagcagac aggaaattat | 1320 | |
| gaagcgcatg attttgttct gcaaggccgc tgtcgaggtt ccttggcacg ttccatgcgg | 1380 | |
| cggtgtccct tatggggatg gaaatctggt gtttattgca aatgattggc acacggcact | 1440 | |
| cctgcctgtc tatctgaaag catattacag ggaccatggt ttgatgcagt acactcggtc | 1500 | |
| cattatggtg atacataaca tcgcgcacca gggccgtggc ccagtagatg aattcccgtt | 1560 | |
| caccgagttg cctgagcact acctggaaca cttcagactg tacgaccccg tgggtggtga | 1620 | |
| gcacgccaac tacttcgccg ccggcctgaa gatggcggac caggttgtcg tggtgagccc | 1680 | |
| cgggtacctg tgggagctca agacggtgga gggcggctgg gggcttcacg acatcatacg | 1740 | |
| gcagaacgac tggaagaccc gcggcatcgt caacggcatc gacaacatgg agtggaaccc | 1800 | |
| cgaggtggac gtccacctca gtcggacgg ctacaccaac ttctccctgg ggacgctgga | 1860 | |
| ctccggcaag cggcagtgca aggaggccct gcagcgcgag ctgggcctgc aggtccgcgc | 1920 | |
| cgacgtgccg ctgctcggct tcatcggccg cctggacggg cagaagggcg tggagatcat | 1980 | |
| cgcggacgcc atgccctgga tcgtgagcca ggacgtgcag ctggtcatgc tgggcaccgg | 2040 | |
| ccgccacgac ctggagagca tgctgcggca cttcgagcgg gagcaccacg acaaggtgcg | 2100 | |
| cgggtgggtg gggttctccg tgcgcctggc gcaccggatc acggcgggcg ccgacgcgct | 2160 | |
| cctcatgccc tcccggttcg agccgtgcgg gttgaaccag ctttacgcca tggcctacgg | 2220 | |
| caccgtcccc gtcgtgcacg ccgtcggcgg ggtgagggac accgtgccgc cgttcgaccc | 2280 | |
| cttcaaccac tccggcctcg ggtggacgtt cgaccgcgcc gaggcgcaca agctgatcga | 2340 | |
| ggcgctcggg cactgcctcc gcacctaccg ggactacaag gagagctgga ggggcctcca | 2400 | |

```
ggagcgcggc atgtcgcagg acttcagctg ggagcatgcc gccaagctct acgaggacgt    2460
cctcctcaag gccaagtacc agtggtgaac gctagctgct agccgctcca gccccgcatg    2520
cgtgcatgca tgagagggtg gaactgcgca ttgcgcccgc aggaacgtgc catccttctc    2580
gatgggagcg ccggcatccg cgaggtgcag tgacatgaga ggtgtgtgtg gttgagacgc    2640
tgattccgat ctcgatctgg tccgtagcag agtagagcgg acgtagggaa gcgctccttg    2700
ttgcaggtat atgggaatgt tgtcaacttg gtattgtagt ttgctatgtt gtatgcgtta    2760
ttacaatgtt gttacttatt cttgttaagt cggaggcaaa gggcgaaagc tagctcacat    2820
gaaaaaaaaa aaaaaaaaaa aa                                             2842
```

<210> SEQ ID NO 4
<211> LENGTH: 799
<212> TYPE: PRT
<213> ORGANISM: Triticum aestivum

<400> SEQUENCE: 4

```
Met Ser Ser Ala Val Ala Ser Ala Ala Ser Phe Leu Ala Leu Ala Ser
1               5                   10                  15

Ala Ser Pro Gly Arg Ser Arg Arg Ala Arg Val Ser Ala Pro Pro
            20                  25                  30

Pro His Ala Gly Ala Gly Arg Leu His Trp Pro Pro Trp Pro Pro Gln
        35                  40                  45

Arg Thr Ala Arg Asp Gly Gly Val Ala Arg Ala Ala Gly Lys Lys
    50                  55                  60

Asp Ala Arg Val Asp Asp Ala Ala Ser Ala Arg Gln Pro Arg Ala
65                  70                  75                  80

Arg Arg Gly Gly Ala Ala Thr Lys Val Ala Glu Arg Arg Asp Pro Val
                85                  90                  95

Lys Thr Leu Asp Arg Asp Ala Ala Glu Gly Gly Ala Pro Ala Pro Pro
            100                 105                 110

Ala Pro Arg Gln Asp Ala Ala Arg Pro Pro Ser Met Asn Gly Thr Pro
        115                 120                 125

Val Asn Gly Glu Asn Lys Ser Thr Gly Gly Gly Ala Thr Lys Asp
    130                 135                 140

Ser Gly Leu Pro Ala Pro Ala Arg Ala Pro His Pro Ser Thr Gln Asn
145                 150                 155                 160

Arg Val Pro Val Asn Gly Glu Asn Lys Ala Asn Val Ala Ser Pro Pro
                165                 170                 175

Thr Ser Ile Ala Glu Val Val Ala Pro Asp Ser Ala Ala Thr Ile Ser
            180                 185                 190

Ile Ser Asp Lys Ala Pro Glu Ser Val Val Pro Ala Glu Lys Pro Pro
        195                 200                 205

Pro Ser Ser Gly Ser Asn Phe Val Val Ser Ala Ser Ala Pro Arg Leu
    210                 215                 220

Asp Ile Asp Ser Asp Val Glu Pro Glu Leu Lys Lys Gly Ala Val Ile
225                 230                 235                 240

Val Glu Glu Ala Pro Asn Pro Lys Ala Leu Ser Pro Pro Ala Ala Pro
                245                 250                 255

Ala Val Gln Glu Asp Leu Trp Asp Phe Lys Lys Tyr Ile Gly Phe Glu
            260                 265                 270

Glu Pro Val Glu Ala Lys Asp Asp Gly Trp Ala Val Ala Asp Asp Ala
        275                 280                 285
```

```
Gly Ser Phe Glu His His Gln Asn His Asp Ser Gly Pro Leu Ala Gly
    290                 295                 300

Glu Asn Val Met Asn Val Val Val Ala Ala Glu Cys Ser Pro Trp
305                 310                 315                 320

Cys Lys Thr Gly Gly Leu Gly Asp Val Ala Gly Ala Leu Pro Lys Ala
                325                 330                 335

Leu Ala Lys Arg Gly His Arg Val Met Val Val Pro Arg Tyr Gly
                340                 345                 350

Asp Tyr Glu Glu Ala Tyr Asp Val Gly Val Arg Lys Tyr Tyr Lys Ala
        355                 360                 365

Ala Gly Gln Asp Met Glu Val Asn Tyr Phe His Ala Tyr Ile Asp Gly
370                 375                 380

Val Asp Phe Val Phe Ile Asp Ala Pro Leu Phe Arg His Arg Gln Glu
385                 390                 395                 400

Asp Ile Tyr Gly Gly Ser Arg Gln Glu Ile Met Lys Arg Met Ile Leu
                405                 410                 415

Phe Cys Lys Ala Ala Val Glu Val Pro Trp His Val Pro Cys Gly Gly
                420                 425                 430

Val Pro Tyr Gly Asp Gly Asn Leu Val Phe Ile Ala Asn Asp Trp His
        435                 440                 445

Thr Ala Leu Leu Pro Val Tyr Leu Lys Ala Tyr Tyr Arg Asp His Gly
        450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
                500                 505                 510

Ala Asn Tyr Phe Ala Ala Gly Leu Lys Met Ala Asp Gln Val Val Val
        515                 520                 525

Val Ser Pro Gly Tyr Leu Trp Glu Leu Lys Thr Val Glu Gly Gly Trp
530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Val His
                565                 570                 575

Leu Lys Ser Asp Gly Tyr Thr Asn Phe Ser Leu Gly Thr Leu Asp Ser
                580                 585                 590

Gly Lys Arg Gln Cys Lys Glu Ala Leu Gln Arg Glu Leu Gly Leu Gln
        595                 600                 605

Val Arg Ala Asp Val Pro Leu Leu Gly Phe Ile Gly Arg Leu Asp Gly
610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Arg His Phe Glu Arg Glu His His Asp Lys Val Arg Gly
                660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
690                 695                 700

Leu Tyr Ala Met Ala Tyr Gly Thr Val Pro Val Val His Ala Val Gly
```

```
                    705                 710                 715                 720
Gly Val Arg Asp Thr Val Pro Pro Phe Asp Pro Phe Asn His Ser Gly
                        725                 730                 735

Leu Gly Trp Thr Phe Asp Arg Ala Glu Ala His Lys Leu Ile Glu Ala
                740                 745                 750

Leu Gly His Cys Leu Arg Thr Tyr Arg Asp Tyr Lys Glu Ser Trp Arg
                755                 760                 765

Gly Leu Gln Glu Arg Gly Met Ser Gln Asp Phe Ser Trp Glu His Ala
            770                 775                 780

Ala Lys Leu Tyr Glu Asp Val Leu Leu Lys Ala Lys Tyr Gln Trp
785                 790                 795

<210> SEQ ID NO 5
<211> LENGTH: 2780
<212> TYPE: DNA
<213> ORGANISM: Triticum aestivum

<400> SEQUENCE: 5
cggaggacca acccgcgcat cgtaccatcg cccgccccga tcccggccgc cgccatgtcg     60
tcggcggtcg cgtccgccgc gtccttcctc gcgctcgcct ccgcctcccc cgggagatca    120
cgcaggcggg cgagggtgag cgcgccgcca ccccacgccg gggccggcag gctgcactgg    180
ccgccgtggc cgccgcagcg cacggctcgc gacggaggtg tggccgcgcg cgccgccggg    240
aagaaggacg cgagggtcga cgacgacgcc gcgtccgcga ggcagccccg cgcacgccgc    300
ggtggcgccg ccaccaaggt cgcggagcgg agggatcccg tcaagacgct cgatcgcgac    360
gccgcggaag gtggcgcgcc ggcaccgccg gcaccgaggc aggacgccgc ccgtccaccg    420
agtatgaacg gcacgccggt gaacggtgag aacaaatcta ccggcggcgg cggcgcgacc    480
aaagacagcg ggctgcccgc acccgcacgc gcgccccatc cgtcgaccca gaacagagta    540
ccagtgaacg tgaaaacaa agctaacgtc gcctcgccgc cgacgagcat agccgaggtc    600
gtggctccgg attccgcagc taccatttcc atcagtgaca aggcgccgga gtccgttgtc    660
ccagccgaga gccgccgcc gtcgtccggc tcaaatttcg tggtctcggc ttctgctccc    720
aggctggaca ttgacagcga tgttgaacct gaactgaaga agggtgcggt catcgtcgaa    780
gaagctccaa acccaaaggc tctttcgccg cctgcagccc ccgctgtaca agaagacctt    840
tgggacttca agaaatacat tggcttcgag gagcccgtgg aggccaagga tgatggctgg    900
gctgttgcag atgatgcggg ctcctttgaa catcaccaga accatgattc cggaccttg     960 gcaggggaga acgtcatgaa cgtggtcgtc gtggctgctg aatgttctcc ctggtgcaaa   1020
acaggtggtc ttggagatgt tgcgggtgct ctgcccaagg ctttggcaaa gagaggacat   1080
cgtgttatgg ttgtggtacc aaggtatggg gactatgagg aagcctacga tgtcggagtc   1140
cgaaaatact acaaggctgc tggacaggat atggaagtga attatttcca tgcttatatc   1200 gatgagttg attttgtgtt cattgacgct cctatcttcc gacaccgtca ggaagacatt   1260
tatgggggca gcagacagga aattatgaag cgcatgattt tgttctgcaa ggccgctgtc   1320
gaggttcctt ggcacgttcc atgcggcggt gtcccttatg gggatggaaa tctggtgttt   1380
attgcaaatg attggcacac ggcactcctg cctgtctatc tgaaagcata ttacagggac   1440
catggtttga tgcagtacac tcggtccatt atggtgatac ataacatcgc gcaccagggc   1500
cgtggcccag tagatgaatt cccgttcacc gagttgcctg agcactacct ggaacacttc   1560
agactgtacg accccgtggg tggtgagcac gccaactact cgccgccgg cctgaagatg   1620
```

```
gcggaccagg ttgtcgtggt gagccccggg tacctgtggg agctcaagac ggtggagggc    1680
ggctgggggc ttcacgacat catacggcag aacgactgga agacccgcgg catcgtcaac    1740
ggcatcgaca acatggagtg gaaccccgag gtggacgtcc acctccagtc ggacggctac    1800
accaacttct ccctgagcac gctggactcc ggcaagcggc agtgcaagga ggccctgcag    1860
cgcgagctgg gcctgcaggt ccgcgccgac gtgccgctgc tcggcttcat cggccgcctg    1920
gacgggcaga agggcgtgga gatcatcgcg gacgccatgc cctggatcgt gagccaggac    1980
gtgcagctgg tcatgctggg caccggccgc cacgacctgg agagcatgct gcggcacttc    2040
gagcgggagc accacgacaa ggtgcgcggg tgggtggggt tctccgtgcg cctggcgcac    2100
cggatcacgg cgggcgccga cgcgctcctc atgccctccc ggttcgagcc gtgcgggctg    2160
aaccagctct acgccatggc ctacggcacc gtccccgtcg tgcacgccgt cggcgggctg    2220
agggacaccg tgccgccgtt cgacccctcc aaccactccg gcctcgggtg gacgttcgac    2280
cgcgccgagg cgcacaagct gatcgaggcg ctcgggcact gcctccgcac ctaccgggac    2340
tacaaggaga gctggagggg cctccaggag cgcggcatgt cgcaggactt cagctgggag    2400
catgccgcca agctctacga ggacgtcctc ctcaaggcca agtaccagtg gtgaacgcta    2460
gctgctagcc gctccagccc cgcatgcgtg catgcatgag agggtggaac tgcgcattgc    2520
gcccgcagga acgtgccatc cttctcgatg ggagcgccgg catccgcgag gtgcagtgac    2580
atgagaggtg tgtgtggttg agacgctgat tccgatctcg atctggtccg tagcagagta    2640
gagcggacgt agggaagcgc tccttgttgc aggtatatgg gaatgttgtc aacttggtat    2700
tgtagtttgc tatgttgtat gcgttattac aatgttgtta cttattcttg ttaaaaaaaa    2760
aaaaaaaaaa aaaaaaaaaa                                               2780
```

<210> SEQ ID NO 6
<211> LENGTH: 799
<212> TYPE: PRT
<213> ORGANISM: Triticum aestivum

<400> SEQUENCE: 6

```
Met Ser Ser Ala Val Ala Ser Ala Ala Ser Phe Leu Ala Leu Ala Ser
1               5                   10                  15

Ala Ser Pro Gly Arg Ser Arg Arg Ala Arg Val Ser Ala Pro Pro
            20                  25                  30

Pro His Ala Gly Ala Gly Arg Leu His Trp Pro Trp Pro Gln
        35                  40                  45

Arg Thr Ala Arg Asp Gly Val Ala Ala Arg Ala Ala Gly Lys Lys
    50                  55                  60

Asp Ala Arg Val Asp Asp Ala Ala Ser Ala Arg Gln Pro Arg Ala
65                  70                  75                  80

Arg Arg Gly Gly Ala Ala Thr Lys Val Ala Glu Arg Arg Asp Pro Val
                85                  90                  95

Lys Thr Leu Asp Arg Asp Ala Ala Glu Gly Gly Ala Pro Ala Pro
            100                 105                 110

Ala Pro Arg Gln Asp Ala Ala Arg Pro Pro Ser Met Asn Gly Thr Pro
            115                 120                 125

Val Asn Gly Glu Asn Lys Ser Thr Gly Gly Gly Ala Thr Lys Asp
            130                 135                 140

Ser Gly Leu Pro Ala Pro Ala Arg Ala Pro His Pro Ser Thr Gln Asn
145                 150                 155                 160

Arg Val Pro Val Asn Gly Glu Asn Lys Ala Asn Val Ala Ser Pro Pro
```

-continued

```
                165                 170                 175
Thr Ser Ile Ala Glu Val Val Ala Pro Asp Ser Ala Thr Ile Ser
                180                 185                 190

Ile Ser Asp Lys Ala Pro Glu Ser Val Val Pro Ala Glu Lys Pro Pro
                195                 200                 205

Pro Ser Ser Gly Ser Asn Phe Val Val Ser Ala Ser Ala Pro Arg Leu
210                 215                 220

Asp Ile Asp Ser Asp Val Glu Pro Glu Leu Lys Lys Gly Ala Val Ile
225                 230                 235                 240

Val Glu Glu Ala Pro Asn Pro Lys Ala Leu Ser Pro Pro Ala Ala Pro
                245                 250                 255

Ala Val Gln Glu Asp Leu Trp Asp Phe Lys Lys Tyr Ile Gly Phe Glu
                260                 265                 270

Glu Pro Val Glu Ala Lys Asp Asp Gly Trp Ala Val Ala Asp Asp Ala
                275                 280                 285

Gly Ser Phe Glu His His Gln Asn His Asp Ser Gly Pro Leu Ala Gly
290                 295                 300

Glu Asn Val Met Asn Val Val Val Ala Ala Glu Cys Ser Pro Trp
305                 310                 315                 320

Cys Lys Thr Gly Gly Leu Gly Asp Val Ala Gly Ala Leu Pro Lys Ala
                325                 330                 335

Leu Ala Lys Arg Gly His Arg Val Met Val Val Pro Arg Tyr Gly
                340                 345                 350

Asp Tyr Glu Glu Ala Tyr Asp Val Gly Val Arg Lys Tyr Tyr Lys Ala
                355                 360                 365

Ala Gly Gln Asp Met Glu Val Asn Tyr Phe His Ala Tyr Ile Asp Gly
370                 375                 380

Val Asp Phe Val Phe Ile Asp Ala Pro Ile Phe Arg His Arg Gln Glu
385                 390                 395                 400

Asp Ile Tyr Gly Gly Ser Arg Gln Glu Ile Met Lys Arg Met Ile Leu
                405                 410                 415

Phe Cys Lys Ala Ala Val Glu Val Pro Trp His Val Pro Cys Gly Gly
                420                 425                 430

Val Pro Tyr Gly Asp Gly Asn Leu Val Phe Ile Ala Asn Asp Trp His
                435                 440                 445

Thr Ala Leu Leu Pro Val Tyr Leu Lys Ala Tyr Tyr Arg Asp His Gly
                450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
                500                 505                 510

Ala Asn Tyr Phe Ala Ala Gly Leu Lys Met Ala Asp Gln Val Val Val
                515                 520                 525

Val Ser Pro Gly Tyr Leu Trp Glu Leu Lys Thr Val Glu Gly Gly Trp
                530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Val His
                565                 570                 575

Leu Gln Ser Asp Gly Tyr Thr Asn Phe Ser Leu Ser Thr Leu Asp Ser
                580                 585                 590
```

Gly Lys Arg Gln Cys Lys Glu Ala Leu Gln Arg Glu Leu Gly Leu Gln
        595                 600                 605

Val Arg Ala Asp Val Pro Leu Leu Gly Phe Ile Gly Arg Leu Asp Gly
    610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Arg His Phe Glu Arg Glu His His Asp Lys Val Arg Gly
            660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
    690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
                725                 730                 735

Leu Gly Trp Thr Phe Asp Arg Ala Glu Ala His Lys Leu Ile Glu Ala
            740                 745                 750

Leu Gly His Cys Leu Arg Thr Tyr Arg Asp Tyr Lys Glu Ser Trp Arg
        755                 760                 765

Gly Leu Gln Glu Arg Gly Met Ser Gln Asp Phe Ser Trp Glu His Ala
    770                 775                 780

Ala Lys Leu Tyr Glu Asp Val Leu Leu Lys Ala Lys Tyr Gln Trp
785                 790                 795

<210> SEQ ID NO 7
<211> LENGTH: 6811
<212> TYPE: DNA
<213> ORGANISM: Triticum aestivum

<400> SEQUENCE: 7
gggggccgtt cgtacgtacc cacccctcgt gtaaagccgc cgccgtcgtc gccgtccccc     60
gctcgcggcc atttcctcgg cctgaccccg tgcgtttacc ccacacagag cacactccag    120
tccagtccag cccactgccg cgctactccc cactcccact gccaccacct ccgcctgcgc    180
cgcgctctgg gcggaccaac ccgcgcatcg tatcacgatc acccaccccg atcccggccg    240
ccgccatgtc gtcggcggtc gcgtccgccg cgtccttcct cgcgctcgcg tccgcctccc    300
ccgggagatc acggaggagg acgagggtga gcgcgtcgcc accccacacc ggggctggca    360
ggttgcactg gccgccgtcg ccgccgcagc gcacggctcg cgacggagca gtggccgcgc    420
gcgccgccgg gaagaaggac gcggggatcg acgacgccgc gcccgcgagg cagccccgcg    480
cactccgcgc tggcgccgcc accaaggtag ttagttatga ccaagttatg acgcgtgcgc    540
gcgccttgag atcatcgtcg tctcgctgac aaattgttta tacaaaacgc acgcgcgcgc    600
gtgtgtgcag gttgcggagc ggagggatcc cgtcaagacg ctcgatcgcg acgccgcgga    660
aggtggcgcg ccgtccccgc cggcaccgag gcaggaggac gcccgtctgc cgagcatgaa    720
cggcatgccg gtgaacggtg aaaacaaatc taccggcggc ggcggcgcga ctaaagacag    780
cgggctgccc gcacccgcac gcgcgcccca ccgtcgagc cagaacagag taccggtgaa    840
tggtgaaaac aaagctaacg tcgcctcgcc gccgacgagc atagccgagg tcgcggctcc    900
ggatcccgca gctaccattt ccatcagtga caaggcgcca gagtccgttg tcccagccga    960

```
gaaggcgccg ccgtcgtccg gctcaaattt cgtgccctcg gcttctgctc ccgggtctga    1020
cactgtcagc gacgtggaac ttgaactgaa gaagggtgcg gtcattgtca aagaagctcc    1080
aaacccaaag gctctttcgc cgcctgcagc acccgctgta caacaagacc tttgggactt    1140
caagaaatac attggtttcg aggagcccgt ggaggccaag gatgatggcc gggctgttgc    1200
agatgatgcg ggctccttcg aacaccacca gaatcacgat tccgggcctt tggcagggga    1260
gaacgtcatg aacgtggtcg tcgtggctgc tgaatgttct ccctggtgca aaacaggcat    1320
ggacattacc tcttcagtgt cttttttctc tctgttcata aaacctggct tgaattactc    1380
ataagaacaa cgttgtgtt gcataggtgg tcttggagat gttgccggtg ctttgcccaa    1440
ggctttggcg aagagaggac atcgtgttat ggtaccacat gctttcattt aactctgttg    1500
aatccatatg ttcgaataat atcagtgagc agtataatgt tattaagtgc aagacatgaa    1560
agtgttcttc tgttatagag tatttcatag ccaaccctgg aggttaggtt gttggggcct    1620
actgggtgtg ggagggggtt tgaaaaaagt gttggttagc agtcggattt cacaaagaac    1680
gctgataacc acgccatcag tgaagggaat gaatgtcggg tacccgatcg accgttttgc    1740
ccgacgtcag gtttacccgc cctgtaggtc cgaataagta gttcctatcc tcagttaagt    1800
accaaatatc ggcagcgccc gtgtgtgtat ttatagtact ggatgatcaa tttatcaaca    1860
ttttcagtta atggttgcta tcatattcac tgtaattgtt agtaaacagt ggatgtttgt    1920
aatgtagatg atggctaaat gtatgttgtc aagctttcat ttcaatgcaa tttttattgg    1980
gagctagttt tggggttcgg ttagagccac caaaacccca gaattctggg agttggctt    2040 gtgagagagg gttttggcga gttgactttc gggattcagt tagagacgct cttactagtt    2100
ccagtaaaga agtaaactat tttctgcaga catcccaatt attctgtaga aattagaagt    2160
agaaaatagt tatggtatca tataaccata tattattcaa aatctagaat catggacttg    2220
gctagacttt gatgatctga aattttaaat ttgatgataa ttgagaaatg atcctttcta    2280
tcttaggttg tggtaccaag gtatggggac tatgaggaag cctacgatgt cggagtccga    2340
aaatactaca aggctgctgg acaggtaagc gaaaatgcaa tcaaagggga gctgaaattt    2400
caatgcttac tatcataata aatcaatttt aagtgttttt ttttgtcctg caggatatgg    2460
aagtgaatta tttccatgct tatatcgatg gagttgattt tgtgttcatt gacgctcctc    2520
tcttccgaca ccgccaggaa gacatttatg ggggcagcag acaggttaat cttctatatg    2580
ttggtgtttg attgcactga taaactgaga acaagccaag gcctactgac cggcatatga    2640
ttacacattt tattttttca ggaaattatg aagcgcatga ttttgttctg caaggccgct    2700
gtcgaggtat cctctccaac tcaattgaca acctattaca actatacaat tatgtgtatg    2760
catgtatttc aacagatacg taatctcttg tgaagtgcat atatactaac aacatttcaa    2820
taccttacat gcacatttgg tcaagcgtta tgatttaact tctaataatc tattgcactg    2880
atgaacaatt atcttgatga tccttggtac ttcatcgtta tgtttccatg ttctcttcac    2940
cgattgattt ggaaatagca tttccacctg ccacaaacaa taatatacac tcctactttc    3000
atccaatgta gatattttcg cacttggcat atcatcccat taaatattat tggtccatca    3060
tttttattcc tctataattt gcaggttcca tggcacgttc catgcggcgg tgtcccttat    3120
ggggatggaa atctggtgtt tattgcaaat gattggcaca cggcactcct gcctgtctat    3180
ctgaaagcat attacaggga ccatggtttg atgcagtaca ctcggtccat tatggtgata    3240
cataacatcg ctcaccaggt tccttttctc caaatcttga ttttttctcta gtctctacta    3300
```

```
tttactccac attgtttgag gaaactaaac gggttgcaaa attatgatgg cttatgaaag      3360
ttatagtctt atataggtaa atgcaccagt ggtgcttgca cttgtcacgc gtgttcacttt     3420 tggtgcttac agttgtagac aataaaaaac tagtgcaaaa acttggctgt tgtgtgcaat      3480
acggtgcatt ttccgtatgt aggagtcaaa tattgcctgt gtggcattgt attcccgtct      3540
atagctgtta gaccatgcct acgtcgccat tgggcccaca caccctctat tacatgtggg      3600
ccccacttgt cagcctatga cataaataaa tggaaattta taatgaaaat gatggcctgg      3660
ggtcttgaaa atgggccgtc gcaggtatgc tggtagccag catgccctaa tcattaatcc      3720
ccctatgcac ttcatgtctt gtgtatgtgt gtgtgggaaa gggggggggt atgtatgctt      3780
atgcttatat cctttgctcc aaggctgcca tcctcaacaa gcccacctcc agcttcaaca      3840
cggccagcgc cttcatgatg gcccaggtgc tccgcaccat cgatcgaagc ggcaacgtcg      3900
tcgtcacgac catccaccaa cccaacgcac aaaatcctca ggctccgttc ggtacggagg      3960
aagagaaaat gcaggaaaaa acaacttcat gggaacaagg tttggtgaac agtaaaaaca      4020
tgtggaatct gaaaatgtag gtaccagaaa aaccggcctg ttcggtttgc aggaaaaagc      4080
atacttgcag cagcactgtt tggcccttcc cagtgtaagg ctaaccatag tgggagtaac      4140
ataactaata ttatgtactt ggaactcaca aacatgctta tgtggcaggc aattaaagaa      4200
gagagagaga gtcatagtaa catagttaga taccgtatca taataaatat tatgttacta      4260
tgtgtcatgc atgacaataa atgagaccat ctgtgatact acgttatgat attatgcact      4320
atagatgtag tatcatacac tagtatcata tgcatgatac tagtgtatgt tactccccac      4380
tatgaccagc ctaacgaggg gatgggcatc agtagtgatt accagttttt attatttttt      4440
attcggctgg acgccctact cttgtggtgc gtagcggaaa aaggcagtgc tagcttcggg      4500
actccgcgag cacatgaggt tctaccggat tttagatttc ctataaaaag tacaggctca      4560
cgcaactttt caatggaaca gaccatcaag attcctttga accgaacgca ctgcatgcaa      4620
gaattccaat gaaaacgag ccgtcaaatg ttcctgcgaa tttcctctat accgaacaga      4680
ccctcaacat cctcaaatag tgagcatgcc cctcttgtcc tttcccctc gtacccaaac       4740 gccatttggc gctcttggtg ttggatcatt tgcctcgggc atttgccaat ttggcgccga      4800
accatattaa agctatgact acttggtgtt ggatcaggga cgcaaagaat cccataaata      4860
ttgcaacgtt cattcaaatt cttaacattt gcgaggcgct tcatgatttc catctccgtc      4920
aggtctgaga catttggtcg tgtacactaa atttctcagg tcacttctcg tctaaatccg      4980
catatgtagc tcacttcaat gacttgcctt tggtctagct aacgccattt ggcgctcttg      5040
ggcccccttg cttagcaaat ttttcatatg gctcgcactg cgcaagagga tttagatcac      5100
gggcagacgc gctagacgag gtcttccgca caatgaacat tgcgttcttt gctctgctct      5160
tcccggagac acttgtgatc ttattacgag ttgtgccatt tcaaacatct gtctctccat      5220
ggtcgctcca gccatagatg ccttgttctc tgaatggtgg gtttcagcta ggaacagggt      5280
gccaccttcg acaagaagtt gcatagtttg gtcgtcttga ctgcttggtc gatttggaag      5340
gaacgcaaca taagagtctt tgaaggcaaa gctaatttct ttgatcaagt tattagccag      5400
atcaaatgtg atgtattcta ctggtacaag gccgggctta ttggctttga gtcactttt       5460 agctaaggcc gcttgggcta agcgcttggg gtcgttttg ctcaactgta gcctgaactt       5520
tctggacttt gtaattttt ttatcctcta taatgatcac atacagctct cctgcatggt       5580
tcgaaaagga aaaatgtgaa catgtgtggc aagtttaagc acaacccgtg catttacctc      5640
aaagttatac aacactgaca tgctgaatta cattttttt gaggatctga catgccgaat       5700
```

```
tacatgcttt ggacagttat tcatttcttc ggtacaccat tggctaatta tttctcttga    5760
cagttgctga attagtacat gctttggtcg cagttattcc tttgttcggt actctgttgg    5820
gctaattatt tctcttgatt gatgttgcat gcagggccgt ggcccagtag atgagttccc    5880
gttcaccgag ttgcctgagc actacctgga acacttcaga ctgtacgacc ccgtgggtgg    5940
tgaacacgcc aactacttcg ccgccggcct gaagatggcg gaccaggttg tcgtcgtgag    6000
cccggggtac ctgtgggagc tgaagacggt ggagggcggc tggggggcttc acgacatcat    6060 acggcagaac gactggaaga cccgcggcat cgtgaacggc atcgacaaca tggagtggaa    6120
ccccgaggtg gacgtccacc tcaagtcgga cggctacacc aacttctccc tggggacgct    6180
ggactccggc aagcggcagt gcaaggaggc cctgcagcgg gagctgggcc tgcaggtccg    6240
cggcgacgtg ccgctgctcg gcttcatcgg gcgcctggac gggcagaagg gcgtggagat    6300
catcgcggac gcgatgccct ggatcgtgag ccaggacgtg cagctggtca tgctgggcac    6360
cgggcgccac gacctggagg gcatgctgcg gcacttcgag cgggagcacc acgacaaggt    6420
gcgcgggtgg gtgggggttct ccgtgcggct ggcgcaccgg atcacggccg cgccgacgc    6480 gctcctcatg ccctcccggt tcgagccgtg cggactgaac cagctctacg ccatggccta    6540
cggcaccgtc ccgtcgtgc atgccgtcgg cggcctgagg gacaccgtgc gccgttcga    6600 ccccttcaac cactccgggc tcgggtggac gttcgaccgc gcagaggcgc agaagctgat    6660
cgaggcgctc gggcactgcc tccgcaccta ccgggactac aaggagagct ggaggggct    6720 ccaggagcgc ggcatgtcgc aggacttcag ctgggagcat gccgccaagc tctacgagga    6780
cgtcctcgtc aaggccaagt accagtggtg a                                   6811
```

<210> SEQ ID NO 8
<211> LENGTH: 798
<212> TYPE: PRT
<213> ORGANISM: Triticum aestivum

<400> SEQUENCE: 8

```
Met Ser Ser Ala Val Ala Ser Ala Ala Ser Phe Leu Ala Leu Ala Ser
1               5                   10                  15

Ala Ser Pro Gly Arg Ser Arg Arg Thr Arg Val Ser Ala Ser Pro
                20                  25                  30

Pro His Thr Gly Ala Gly Arg Leu His Trp Pro Pro Ser Pro Pro Gln
                35                  40                  45

Arg Thr Ala Arg Asp Gly Ala Val Ala Ala Arg Ala Ala Gly Lys Lys
            50                  55                  60

Asp Ala Gly Ile Asp Asp Ala Ala Pro Ala Arg Gln Pro Arg Ala Leu
65                  70                  75                  80

Arg Gly Gly Ala Ala Thr Lys Val Ala Glu Arg Asp Pro Val Lys
                85                  90                  95

Thr Leu Asp Arg Asp Ala Ala Glu Gly Gly Ala Pro Ser Pro Ala
                100                 105                 110

Pro Arg Gln Glu Asp Ala Arg Leu Pro Ser Met Asn Gly Met Pro Val
            115                 120                 125

Asn Gly Glu Asn Lys Ser Thr Gly Gly Gly Ala Thr Lys Asp Ser
            130                 135                 140

Gly Leu Pro Ala Pro Ala Arg Ala Pro Gln Pro Ser Ser Gln Asn Arg
145                 150                 155                 160

Val Pro Val Asn Gly Glu Asn Lys Ala Asn Val Ala Ser Pro Pro Thr
                165                 170                 175
```

```
Ser Ile Ala Glu Val Ala Ala Pro Asp Pro Ala Ala Thr Ile Ser Ile
            180                 185                 190

Ser Asp Lys Ala Pro Glu Ser Val Pro Ala Glu Lys Ala Pro Pro
        195                 200                 205

Ser Ser Gly Ser Asn Phe Val Pro Ser Ala Ser Ala Pro Gly Ser Asp
        210                 215                 220

Thr Val Ser Asp Val Glu Leu Glu Leu Lys Lys Gly Ala Val Ile Val
225                 230                 235                 240

Lys Glu Ala Pro Asn Pro Lys Ala Leu Ser Pro Pro Ala Ala Pro Ala
                245                 250                 255

Val Gln Gln Asp Leu Trp Asp Phe Lys Lys Tyr Ile Gly Phe Glu Glu
            260                 265                 270

Pro Val Glu Ala Lys Asp Asp Gly Arg Ala Val Ala Asp Asp Ala Gly
        275                 280                 285

Ser Phe Glu His His Gln Asn His Asp Ser Gly Pro Leu Ala Gly Glu
        290                 295                 300

Asn Val Met Asn Val Val Val Ala Ala Glu Cys Ser Pro Trp Cys
305                 310                 315                 320

Lys Thr Gly Gly Leu Gly Asp Val Ala Gly Ala Leu Pro Lys Ala Leu
                325                 330                 335

Ala Lys Arg Gly His Arg Val Met Val Val Pro Arg Tyr Gly Asp
            340                 345                 350

Tyr Glu Glu Ala Tyr Asp Val Gly Val Arg Lys Tyr Lys Ala Ala
        355                 360                 365

Gly Gln Asp Met Glu Val Asn Tyr Phe His Ala Tyr Ile Asp Gly Val
        370                 375                 380

Asp Phe Val Phe Ile Asp Ala Pro Leu Phe Arg His Arg Gln Glu Asp
385                 390                 395                 400

Ile Tyr Gly Gly Ser Arg Gln Glu Ile Met Lys Arg Met Ile Leu Phe
                405                 410                 415

Cys Lys Ala Ala Val Glu Val Pro Trp His Val Pro Cys Gly Gly Val
            420                 425                 430

Pro Tyr Gly Asp Gly Asn Leu Val Phe Ile Ala Asn Asp Trp His Thr
        435                 440                 445

Ala Leu Leu Pro Val Tyr Leu Lys Ala Tyr Tyr Arg Asp His Gly Leu
450                 455                 460

Met Gln Tyr Thr Arg Ser Ile Met Val Ile His Asn Ile Ala His Gln
465                 470                 475                 480

Gly Arg Gly Pro Val Asp Glu Phe Pro Phe Thr Glu Leu Pro Glu His
                485                 490                 495

Tyr Leu Glu His Phe Arg Leu Tyr Asp Pro Val Gly Gly Glu His Ala
            500                 505                 510

Asn Tyr Phe Ala Ala Gly Leu Lys Met Ala Asp Gln Val Val Val
        515                 520                 525

Ser Pro Gly Tyr Leu Trp Glu Leu Lys Thr Val Glu Gly Gly Trp Gly
        530                 535                 540

Leu His Asp Ile Ile Arg Gln Asn Asp Trp Lys Thr Arg Gly Ile Val
545                 550                 555                 560

Asn Gly Ile Asp Asn Met Glu Trp Asn Pro Glu Val Asp Val His Leu
                565                 570                 575

Lys Ser Asp Gly Tyr Thr Asn Phe Ser Leu Gly Thr Leu Asp Ser Gly
            580                 585                 590
```

```
Lys Arg Gln Cys Lys Glu Ala Leu Gln Arg Glu Leu Gly Leu Gln Val
            595                 600                 605
Arg Gly Asp Val Pro Leu Leu Gly Phe Ile Gly Arg Leu Asp Gly Gln
610                 615                 620
Lys Gly Val Glu Ile Ile Ala Asp Ala Met Pro Trp Ile Val Ser Gln
625                 630                 635                 640
Asp Val Gln Leu Val Met Leu Gly Thr Gly Arg His Asp Leu Glu Gly
                645                 650                 655
Met Leu Arg His Phe Glu Arg Glu His His Asp Lys Val Arg Gly Trp
            660                 665                 670
Val Gly Phe Ser Val Arg Leu Ala His Arg Ile Thr Ala Gly Ala Asp
        675                 680                 685
Ala Leu Leu Met Pro Ser Arg Phe Glu Pro Cys Gly Leu Asn Gln Leu
    690                 695                 700
Tyr Ala Met Ala Tyr Gly Thr Val Pro Val Val His Ala Val Gly Gly
705                 710                 715                 720
Leu Arg Asp Thr Val Pro Pro Phe Asp Pro Phe Asn His Ser Gly Leu
                725                 730                 735
Gly Trp Thr Phe Asp Arg Ala Glu Ala Gln Lys Leu Ile Glu Ala Leu
            740                 745                 750
Gly His Cys Leu Arg Thr Tyr Arg Asp Tyr Lys Glu Ser Trp Arg Gly
        755                 760                 765
Leu Gln Glu Arg Gly Met Ser Gln Asp Phe Ser Trp Glu His Ala Ala
    770                 775                 780
Lys Leu Tyr Glu Asp Val Leu Val Lys Ala Lys Tyr Gln Trp
785                 790                 795

<210> SEQ ID NO 9
<211> LENGTH: 799
<212> TYPE: PRT
<213> ORGANISM: Triticum aestivum

<400> SEQUENCE: 9

Met Ser Ser Ala Val Ala Ser Ala Ala Ser Phe Leu Ala Leu Ala Ser
1               5                   10                  15
Ala Ser Pro Gly Arg Ser Arg Arg Ala Arg Val Ser Ala Gln Pro
                20                  25                  30
Pro His Ala Gly Ala Gly Arg Leu His Trp Pro Pro Trp Pro Pro Gln
            35                  40                  45
Arg Thr Ala Arg Asp Gly Ala Val Ala Ala Leu Ala Ala Gly Lys Lys
50                  55                  60
Asp Ala Gly Ile Asp Asp Ala Ala Ser Val Arg Gln Pro Arg Ala
65                  70                  75                  80
Leu Arg Gly Gly Ala Ala Thr Lys Val Ala Glu Arg Arg Asp Pro Val
                85                  90                  95
Lys Thr Leu Asp Arg Asp Ala Ala Glu Gly Gly Pro Ser Pro Pro
            100                 105                 110
Ala Ala Arg Gln Asp Ala Ala Arg Pro Pro Ser Met Asn Gly Met Pro
        115                 120                 125
Val Asn Gly Glu Asn Lys Ser Thr Gly Gly Gly Ala Thr Lys Asp
    130                 135                 140
Ser Gly Leu Pro Thr Pro Ala Arg Ala Pro His Pro Ser Thr Gln Asn
145                 150                 155                 160
Arg Ala Pro Val Asn Gly Glu Asn Lys Ala Asn Val Ala Ser Pro Pro
                165                 170                 175
```

```
Thr Ser Ile Ala Glu Ala Ala Ser Asp Ser Ala Ala Thr Ile Ser
            180                 185                 190

Ile Ser Asp Lys Ala Pro Glu Ser Val Val Pro Ala Glu Lys Thr Pro
        195                 200                 205

Pro Ser Ser Gly Ser Asn Phe Glu Ser Ser Ala Ser Ala Pro Gly Ser
    210                 215                 220

Asp Thr Val Ser Asp Val Glu Gln Glu Leu Lys Lys Gly Ala Val Val
225                 230                 235                 240

Val Glu Glu Ala Pro Lys Pro Lys Ala Leu Ser Pro Pro Ala Ala Pro
                245                 250                 255

Ala Val Gln Glu Asp Leu Trp Asp Phe Lys Lys Tyr Ile Gly Phe Glu
            260                 265                 270

Glu Pro Val Glu Ala Lys Asp Asp Gly Arg Ala Val Ala Asp Asp Ala
        275                 280                 285

Gly Ser Phe Glu His His Gln Asn His Asp Ser Gly Pro Leu Ala Gly
    290                 295                 300

Glu Asn Val Met Asn Val Val Val Ala Ala Glu Cys Ser Pro Trp
305                 310                 315                 320

Cys Lys Thr Gly Gly Leu Gly Asp Val Ala Gly Ala Leu Pro Lys Ala
                325                 330                 335

Leu Ala Lys Arg Gly His Arg Val Met Val Val Pro Arg Tyr Gly
            340                 345                 350

Asp Tyr Glu Glu Ala Tyr Asp Val Gly Val Arg Lys Tyr Tyr Lys Ala
        355                 360                 365

Ala Gly Gln Asp Met Glu Val Asn Tyr Phe His Ala Tyr Ile Asp Gly
    370                 375                 380

Val Asp Phe Val Phe Ile Asp Ala Pro Leu Phe Arg His Arg Gln Glu
385                 390                 395                 400

Asp Ile Tyr Gly Gly Ser Arg Gln Glu Ile Met Lys Arg Met Ile Leu
                405                 410                 415

Phe Cys Lys Ala Ala Val Glu Val Pro Trp His Val Pro Cys Gly Gly
            420                 425                 430

Val Pro Tyr Gly Asp Gly Asn Leu Val Phe Ile Ala Asn Asp Trp His
        435                 440                 445

Thr Ala Leu Leu Pro Val Tyr Leu Lys Ala Tyr Tyr Arg Asp His Gly
    450                 455                 460

Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
            500                 505                 510

Ala Asn Tyr Phe Ala Ala Gly Leu Lys Met Ala Asp Gln Val Val Val
        515                 520                 525

Val Ser Pro Gly Tyr Leu Trp Glu Leu Lys Thr Val Glu Gly Gly Trp
    530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Ala His
                565                 570                 575

Leu Lys Ser Asp Gly Tyr Thr Asn Phe Ser Leu Arg Thr Leu Asp Ser
            580                 585                 590
```

```
Gly Lys Arg Gln Cys Lys Glu Ala Leu Gln Arg Glu Leu Gly Leu Gln
            595                 600                 605

Val Arg Ala Asp Val Pro Leu Leu Gly Phe Ile Gly Arg Leu Asp Gly
        610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Gln His Phe Glu Arg Glu His His Asp Lys Val Arg Gly
            660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
        690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
                725                 730                 735

Leu Gly Trp Thr Phe Asp Arg Ala Glu Ala His Lys Leu Ile Glu Ala
            740                 745                 750

Leu Gly His Cys Leu Arg Thr Tyr Arg Asp Phe Lys Glu Ser Trp Arg
        755                 760                 765

Ala Leu Gln Glu Arg Gly Met Ser Gln Asp Phe Ser Trp Glu His Ala
        770                 775                 780

Ala Lys Leu Tyr Glu Asp Val Leu Val Lys Ala Lys Tyr Gln Trp
785                 790                 795

<210> SEQ ID NO 10
<211> LENGTH: 2400
<212> TYPE: DNA
<213> ORGANISM: Sorghum bicolor

<400> SEQUENCE: 10
atcgatcgac caccgaatcc cgccgcggcc atgtcgtcgg cggccgtgtc gtccgcttcc      60
tccaccttct tcctcgcgct cgcctcctcg gcctccccgg ggggacgcag gcgggcaagg     120
gtcggctcgc cgccgttcca caccggcgcc ggtccgaatt cgcgttcctg gcgggcgccg     180
ccgcgcgtgc cccgtgacgc ggcgctggtg cgcgcggagg ccgaaggcgg gggcaaggac     240
gcgccgccgg agaggagtgg cgacgccgcc gccgccgccg ccagcaggtg gccccgcgcc     300
gctcggcgca agacggtctc caaacggagg gatcctcttc agccggtcgg ccgttacggc     360
tcatccggaa cggggaacac ggccaggagc ggcgccgcga ccgcgtccac ccagaacgcc     420
gcgttggcgg ccgttgagat caagtccatc gtcgccgcgc cgccgacgag catagtgaag     480
ttcccagccc cgggatacag ggtgatcctt ccctctgggg acatagcgcc ggagactgtc     540
gtcccagccc cgaagccact gccactgcat ggatcgcctg gggttgatgg agattattca     600
aatggggttg cacctcctcc agctgagcca gtagtacagg aggccacttg ggatttcaag     660
aaatacatcg ttttgagga gcctgtggaa gccaaggatg attccggggt tgctgcagat     720
ggtgctgatt cttttgaaca ctacgagaac aatgattctg ggccctttggc cggggagaat     780 gtcatgaacg tcatcgtggt ggctgctgaa tgttctccat ggtgcaaaac aggtggcctt     840
ggagatgttg tggagctttt acccaaggct ttagcgagaa gaggacatcg tgttatggtt     900
gtggttccaa ggtatgggga ctatgtggaa gccttcgata tgggaatccg gaaatactac     960
```

```
aaagctgcag gacaggactt ggaagtgaac tatttccatg catttatcga tggagtagat    1020
tttgtgttca ttgatgcacc tctcttccgg caccgtcaaa atgacatata cgggggaagt    1080
agacaggaaa ttttgaagcg catgattttg ttctgcaagg ttgctgttga ggttccttgg    1140
catgttccat gtggcggtgt gtgctacgga gatggaaatt tggtgttcat tgccaatgat    1200
tggcacactg cactcctgcc tgtttatctg aaggcatatt acacagacca tgggttaatg    1260
cagtacactc gctccattct tgtcatacat aacatcgctc accagggtcg tggtcctgta    1320
gctgaattcc cgtacatgga cttgcctgaa cactacctcc aacatttcga gctgtacgac    1380
cccgtcggtg gtgagcacgc caacatcttt gccgcgggtc tgaagatggc agaccgggtg    1440
gtgacggtca gccggggcta cctgtgggag ctgaagacag tggaaggtgg ctggggcctc    1500
cacgacatca tccgttccaa cgactggaag atcaatggca tcgtgaacgg catcgaccac    1560
caggagtgga accccaaggt ggacgtgcac ctgcggtcgg acgggtacac caactactcc    1620
ctcgagacac tggacgccgg aaagcggcag tgcaaggcgg ccctgcagcg ggagctgggc    1680
ctggaagtgc gcgacgacgt gccgctgctc ggcttcatcg gcgcctgga cgggcagaag    1740 ggcgtggaca tcatcgggga cgcgatgccg tggatcgcgg gcaggacgt gcagctggtg    1800 atgctgggca ccgggcgcgc cgacctggag cggatgctgc agcacctgga gcgggagcac    1860
ccaagcaagg tgcgcgggtg ggtggggttc tcggtgccca tggcgcaccg catcaccgcg    1920
ggcgccgacg tgctggtgat gccctccgg ttcgagccat gcgggctgaa ccagctctac    1980
gccatggcgt acggcaccgt ccccgtggtg cacgccgtcg gcgggctcag ggacaccgtg    2040
gcgccgttcg acccgttcgg cgacgccggg ctcggctgga ctttcgaccg cgccgaggtc    2100
aacaagctga tcgaggcgct caggcactgc ctcgacacgt accggaacta cggggagagc    2160
tggaagagca tccaggcgcg cggcatggca caggacctca gctgggacca cgcggcggag    2220
ctctacgagg acgtcctagt caaggccaag taccagtggt gaaccctccg gcctccgcat    2280
cgctcgatat gtcgagagca acttctgctc gtcgtgtggt tttacaattt tcggtttgat    2340
ccattgtaca ttgcgcattc gacggtctcg gtgaagaact tcatatgcag tgccgcgccg    2400
```

<210> SEQ ID NO 11
<211> LENGTH: 743
<212> TYPE: PRT
<213> ORGANISM: Sorghum bicolor

<400> SEQUENCE: 11

```
Met Ser Ser Ala Ala Val Ser Ser Ala Ser Ser Thr Phe Phe Leu Ala
1               5                   10                  15

Leu Ala Ser Ser Ala Ser Pro Gly Gly Arg Arg Arg Ala Arg Val Gly
            20                  25                  30

Ser Pro Pro Phe His Thr Gly Ala Gly Pro Asn Phe Ala Phe Trp Arg
        35                  40                  45

Ala Pro Pro Arg Val Pro Arg Asp Ala Ala Leu Val Arg Ala Glu Ala
    50                  55                  60

Glu Gly Gly Gly Lys Asp Ala Pro Pro Glu Arg Ser Gly Asp Ala Ala
65                  70                  75                  80

Ala Ala Ala Ala Ser Arg Trp Pro Arg Ala Ala Arg Arg Lys Thr Val
                85                  90                  95

Ser Lys Arg Arg Asp Pro Leu Gln Pro Val Gly Arg Tyr Gly Ser Ser
            100                 105                 110

Gly Thr Gly Asn Thr Ala Arg Ser Gly Ala Ala Thr Ala Ser Thr Gln
        115                 120                 125
```

```
Asn Ala Ala Leu Ala Ala Val Glu Ile Lys Ser Ile Val Ala Ala Pro
    130                 135                 140

Pro Thr Ser Ile Val Lys Phe Pro Ala Pro Gly Tyr Arg Val Ile Leu
145                 150                 155                 160

Pro Ser Gly Asp Ile Ala Pro Glu Thr Val Val Pro Ala Pro Lys Pro
                165                 170                 175

Leu Pro Leu His Gly Ser Pro Gly Val Asp Gly Asp Tyr Ser Asn Gly
            180                 185                 190

Val Ala Pro Pro Ala Glu Pro Val Val Gln Glu Ala Thr Trp Asp
        195                 200                 205

Phe Lys Lys Tyr Ile Gly Phe Glu Glu Pro Val Glu Ala Lys Asp Asp
    210                 215                 220

Ser Gly Val Ala Ala Asp Gly Ala Asp Ser Phe Glu His Tyr Glu Asn
225                 230                 235                 240

Asn Asp Ser Gly Pro Leu Ala Gly Glu Asn Val Met Asn Val Ile Val
                245                 250                 255

Val Ala Ala Glu Cys Ser Pro Trp Cys Lys Thr Gly Gly Leu Gly Asp
                260                 265                 270

Val Val Gly Ala Leu Pro Lys Ala Leu Ala Arg Arg Gly His Arg Val
                275                 280                 285

Met Val Val Pro Arg Tyr Gly Asp Tyr Val Glu Ala Phe Asp Met
    290                 295                 300

Gly Ile Arg Lys Tyr Tyr Lys Ala Ala Gly Gln Asp Leu Glu Val Asn
305                 310                 315                 320

Tyr Phe His Ala Phe Ile Asp Gly Val Asp Phe Val Phe Ile Asp Ala
                325                 330                 335

Pro Leu Phe Arg His Arg Gln Asn Asp Ile Tyr Gly Gly Ser Arg Gln
                340                 345                 350

Glu Ile Leu Lys Arg Met Ile Leu Phe Cys Lys Val Ala Val Glu Val
            355                 360                 365

Pro Trp His Val Pro Cys Gly Gly Val Cys Tyr Gly Asp Gly Asn Leu
    370                 375                 380

Val Phe Ile Ala Asn Asp Trp His Thr Ala Leu Leu Pro Val Tyr Leu
385                 390                 395                 400

Lys Ala Tyr Tyr Thr Asp His Gly Leu Met Gln Tyr Thr Arg Ser Ile
                405                 410                 415

Leu Val Ile His Asn Ile Ala His Gln Gly Arg Gly Pro Val Ala Glu
            420                 425                 430

Phe Pro Tyr Met Asp Leu Pro Glu His Tyr Leu Gln His Phe Glu Leu
        435                 440                 445

Tyr Asp Pro Val Gly Gly Glu His Ala Asn Ile Phe Ala Ala Gly Leu
450                 455                 460

Lys Met Ala Asp Arg Val Val Thr Val Ser Arg Gly Tyr Leu Trp Glu
465                 470                 475                 480

Leu Lys Thr Val Glu Gly Gly Trp Gly Leu His Asp Ile Ile Arg Ser
                485                 490                 495

Asn Asp Trp Lys Ile Asn Gly Ile Val Asn Gly Ile Asp His Gln Glu
                500                 505                 510

Trp Asn Pro Lys Val Asp Val His Leu Arg Ser Asp Gly Tyr Thr Asn
            515                 520                 525

Tyr Ser Leu Glu Thr Leu Asp Ala Gly Lys Arg Gln Cys Lys Ala Ala
    530                 535                 540
```

Leu Gln Arg Glu Leu Gly Leu Glu Val Arg Asp Asp Val Pro Leu Leu
545                 550                 555                 560

Gly Phe Ile Gly Arg Leu Asp Gly Gln Lys Gly Val Asp Ile Ile Gly
            565                 570                 575

Asp Ala Met Pro Trp Ile Ala Gly Gln Asp Val Gln Leu Val Met Leu
        580                 585                 590

Gly Thr Gly Arg Ala Asp Leu Glu Arg Met Leu Gln His Leu Glu Arg
    595                 600                 605

Glu His Pro Ser Lys Val Arg Gly Trp Val Gly Phe Ser Val Pro Met
610                 615                 620

Ala His Arg Ile Thr Ala Gly Ala Asp Val Leu Val Met Pro Ser Arg
625                 630                 635                 640

Phe Glu Pro Cys Gly Leu Asn Gln Leu Tyr Ala Met Ala Tyr Gly Thr
                645                 650                 655

Val Pro Val Val His Ala Val Gly Gly Leu Arg Asp Thr Val Ala Pro
            660                 665                 670

Phe Asp Pro Phe Gly Asp Ala Gly Leu Gly Trp Thr Phe Asp Arg Ala
        675                 680                 685

Glu Val Asn Lys Leu Ile Glu Ala Leu Arg His Cys Leu Asp Thr Tyr
    690                 695                 700

Arg Asn Tyr Gly Glu Ser Trp Lys Ser Ile Gln Ala Arg Gly Met Ala
705                 710                 715                 720

Gln Asp Leu Ser Trp Asp His Ala Ala Glu Leu Tyr Glu Asp Val Leu
                725                 730                 735

Val Lys Ala Lys Tyr Gln Trp
            740

<210> SEQ ID NO 12
<211> LENGTH: 2433
<212> TYPE: DNA
<213> ORGANISM: Oryza sativa

<400> SEQUENCE: 12
atgtcgtcgg ccgtcgtcgc gtcatccacc acgttcctcg tcgcgctcgc ctcttcggcg     60
tcacggggag ggcccaggag ggggagggtg gtgggcgtgg ccgcgccgcc ggccctgctt    120
tacgacggcc gcgccggaag gctagcccta cgggcgccgc ctccgccccg gcctcggcct    180
cggcgtcgga tgcgggcgt ggtgcgccgc gcggatgatg gggagaacga ggcggcggtg    240
gagcgggcgg gtgaggacga cgaggaggag gaggagttct cttcgggcgc gtggcagccg    300
ccccgctcgc gtcgcggcgg cgtcggcaag gtcttgaagc ggaggggcac cgtcccgccc    360
gtcggccggt acggctccgg cggtgacgcg gcgagagtgc gcggggcggc cgcgccggcg    420
ccggcgccga cacaggacgc cgcctcaagt aagaacggag cgcttctcag cggccgcgac    480
gacgacacac ctgcctcacg gaacggatcg tcgttaccg gcgccgacaa gcctgccgcc    540
gccacgccgc cggtgaccat aacgaagctc cagcgccgg actcccccgt gatccttcca    600
tccgtagaca agccgcagcc ggagttcgtc atcccagacg cgacggcgcc ggcgccgcca    660
ccgcccggtt caaatcccag gtcgtccgct cctctcccca agcctgacaa ttcggaattt    720
gcagaggata agagcgcaaa agttgttgag agtgctccga agccaaaggc gactagatct    780
tcccctattc ctgcggtaga agaggagacg tgggatttca agaaatattt tgatctgaac    840
gaaccggacg ccgcggagga tggcgatgac gatgatgact gggctgattc agatgcgtca    900
gattctgaga tcgaccagga tgacgattcg ggcccttttgg ctggggagaa tgtcatgaac    960

```
gtgatcgtgg tggctgctga atgttctccc tggtgcaaaa caggtgggct tggagatgtt    1020
gcaggtgctt tacccaaagc tttggcgagg agaggacatc gtgttatggt tgtggtacca    1080
aggtacggtg attacgcgga agcccaggat gtaggaatca ggaaatacta caaggctgct    1140
ggacaggatc tggaagtgaa atatttccat gcatttatcg atggagttga ttttgtgttc    1200
attgacgctc ctctcttccg tcaccgtcag gatgacatct atgggggaa cagacaggaa    1260 atcatgaagc gcatgattct gttttgtaag gctgctgttg aggttccttg gcacgttcca    1320
tgcggtggtg tgccctatgg ggatggcaac ttggtgttcc ttgcaaacga ttggcacact    1380
gcactcctgc ctgtttatct gaaggcatat tacagagaca atggcatgat gcagtacact    1440
cgctctgtcc ttgtgataca taatatcgct taccagggcc gtggcccagt agatgaattc    1500
ccctacatgg aattgccgga gcactacctg gatcacttca agctgtacga ccccgtcggc    1560
ggcgagcacg ccaacatctt cggcgcgggc ctgaagatgg cggaccgggt ggtgaccgtg    1620
agccccggct acctctggga gctgaagacg acgagggcg gctggggcct ccacgacatc    1680
atacgggaga cgactggaa gatgaacggc atcgtgaacg gcatcgacta ccggagtgg    1740 aacccggagg tggacgtgca cctgcagtcc gacggctacg ccaactacac cgtggcctcg    1800
ctggactccg gcaagccgcg gtgcaaggcg gcgctgcagc gcgagctggg gctggaggtg    1860
cgcgacgacg tgccgctgat cgggttcatc gggcggctcg acgggcagaa aggggtggac    1920
atcatcggcg acgcgatgcc gtggatcgcc gggcaggacg tgcagctggt gctgctgggc    1980
tccggccgcc gcgacctgga ggtgatgctg cagcggttcg aggcgcagca caacagcaag    2040
gtgcgcgggt gggtgggggtt ctcggtgaag atggcgcacc ggatcacggc gggcgccgac    2100
gtgctggtca tgccgtcgcg gttcgagccg tgcggcctca accagctcta cgccatggcg    2160
tacggcaccg tccccgtcgt gcacgccgtc ggcgggctga gggacaccgt gtcggcgttc    2220
gacccgttcg aggacaccgg cctcgggtgg acgttcgacc gcgccgagcc gcacaagctc    2280
atcgaggcgc tcggccactg cctcgagacg taccgcaagt acaaggagag ctggaggggg    2340
ctccaggtgc gcggcatgtc gcaggacctc agctgggacc acgccgccga gctctacgag    2400
gaggtccttg tcaaggccaa gtaccaatgg tga                                  2433
```

<210> SEQ ID NO 13
<211> LENGTH: 810
<212> TYPE: PRT
<213> ORGANISM: Oryza sativa

<400> SEQUENCE: 13

```
Met Ser Ser Ala Val Ala Ser Ser Thr Thr Phe Leu Val Ala Leu
1               5                   10                  15

Ala Ser Ser Ala Ser Arg Gly Gly Pro Arg Arg Gly Arg Val Val Gly
            20                  25                  30

Val Ala Ala Pro Pro Ala Leu Leu Tyr Asp Gly Arg Ala Gly Arg Leu
        35                  40                  45

Ala Leu Arg Ala Pro Pro Pro Arg Pro Arg Pro Arg Arg Arg Asp
    50                  55                  60

Ala Gly Val Val Arg Arg Ala Asp Asp Gly Glu Asn Glu Ala Ala Val
65                  70                  75                  80

Glu Arg Ala Gly Glu Asp Asp Glu Glu Glu Glu Phe Ser Ser Gly
                85                  90                  95

Ala Trp Gln Pro Pro Arg Ser Arg Gly Gly Val Gly Lys Val Leu
            100                 105                 110
```

```
Lys Arg Arg Gly Thr Val Pro Pro Val Gly Arg Tyr Gly Ser Gly Gly
            115                 120                 125

Asp Ala Ala Arg Val Arg Gly Ala Ala Pro Ala Pro Ala Pro Thr
130                 135                 140

Gln Asp Ala Ala Ser Ser Lys Asn Gly Ala Leu Leu Ser Gly Arg Asp
145                 150                 155                 160

Asp Asp Thr Pro Ala Ser Arg Asn Gly Ser Val Val Thr Gly Ala Asp
            165                 170                 175

Lys Pro Ala Ala Ala Thr Pro Pro Val Thr Ile Thr Lys Leu Pro Ala
                180                 185                 190

Pro Asp Ser Pro Val Ile Leu Pro Ser Val Asp Lys Pro Gln Pro Glu
            195                 200                 205

Phe Val Ile Pro Asp Ala Thr Ala Pro Ala Pro Pro Pro Gly Ser
            210                 215                 220

Asn Pro Arg Ser Ser Ala Pro Leu Pro Lys Pro Asp Asn Ser Glu Phe
225                 230                 235                 240

Ala Glu Asp Lys Ser Ala Lys Val Val Glu Ser Ala Pro Lys Pro Lys
                245                 250                 255

Ala Thr Arg Ser Ser Pro Ile Pro Ala Val Glu Glu Thr Trp Asp
            260                 265                 270

Phe Lys Lys Tyr Phe Asp Leu Asn Glu Pro Asp Ala Ala Glu Asp Gly
            275                 280                 285

Asp Asp Asp Asp Asp Trp Ala Asp Ser Asp Ala Ser Asp Ser Glu Ile
            290                 295                 300

Asp Gln Asp Asp Asp Ser Gly Pro Leu Ala Gly Glu Asn Val Met Asn
305                 310                 315                 320

Val Ile Val Val Ala Ala Glu Cys Ser Pro Trp Cys Lys Thr Gly Gly
                325                 330                 335

Leu Gly Asp Val Ala Gly Ala Leu Pro Lys Ala Leu Ala Arg Arg Gly
            340                 345                 350

His Arg Val Met Val Val Pro Arg Tyr Gly Asp Tyr Ala Glu Ala
            355                 360                 365

Gln Asp Val Gly Ile Arg Lys Tyr Tyr Lys Ala Ala Gly Gln Asp Leu
370                 375                 380

Glu Val Lys Tyr Phe His Ala Phe Ile Asp Gly Val Asp Phe Val Phe
385                 390                 395                 400

Ile Asp Ala Pro Leu Phe Arg His Arg Gln Asp Ile Tyr Gly Gly
                405                 410                 415

Asn Arg Gln Glu Ile Met Lys Arg Met Ile Leu Phe Cys Lys Ala Ala
            420                 425                 430

Val Glu Val Pro Trp His Val Pro Cys Gly Gly Val Pro Tyr Gly Asp
            435                 440                 445

Gly Asn Leu Val Phe Leu Ala Asn Asp Trp His Thr Ala Leu Leu Pro
450                 455                 460

Val Tyr Leu Lys Ala Tyr Tyr Arg Asp Asn Gly Met Met Gln Tyr Thr
465                 470                 475                 480

Arg Ser Val Leu Val Ile His Asn Ile Ala Tyr Gln Gly Arg Gly Pro
                485                 490                 495

Val Asp Glu Phe Pro Tyr Met Glu Leu Pro Glu His Tyr Leu Asp His
                500                 505                 510

Phe Lys Leu Tyr Asp Pro Val Gly Gly Glu His Ala Asn Ile Phe Gly
            515                 520                 525

Ala Gly Leu Lys Met Ala Asp Arg Val Val Thr Val Ser Pro Gly Tyr
```

```
              530            535            540
Leu Trp Glu Leu Lys Thr Thr Glu Gly Gly Trp Gly Leu His Asp Ile
545                550                555                560

Ile Arg Glu Asn Asp Trp Lys Met Asn Gly Ile Val Asn Gly Ile Asp
                565                570                575

Tyr Arg Glu Trp Asn Pro Glu Val Asp Val His Leu Gln Ser Asp Gly
                580                585                590

Tyr Ala Asn Tyr Thr Val Ala Ser Leu Asp Ser Gly Lys Pro Arg Cys
            595                600                605

Lys Ala Ala Leu Gln Arg Glu Leu Gly Leu Glu Val Arg Asp Asp Val
            610                615                620

Pro Leu Ile Gly Phe Ile Gly Arg Leu Asp Gly Gln Lys Gly Val Asp
625                630                635                640

Ile Ile Gly Asp Ala Met Pro Trp Ile Ala Gly Gln Asp Val Gln Leu
                645                650                655

Val Leu Leu Gly Ser Gly Arg Arg Asp Leu Glu Val Met Leu Gln Arg
                660                665                670

Phe Glu Ala Gln His Asn Ser Lys Val Arg Gly Trp Val Gly Phe Ser
            675                680                685

Val Lys Met Ala His Arg Ile Thr Ala Gly Ala Asp Val Leu Val Met
            690                695                700

Pro Ser Arg Phe Glu Pro Cys Gly Leu Asn Gln Leu Tyr Ala Met Ala
705                710                715                720

Tyr Gly Thr Val Pro Val Val His Ala Val Gly Gly Leu Arg Asp Thr
                725                730                735

Val Ser Ala Phe Asp Pro Phe Glu Asp Thr Gly Leu Gly Trp Thr Phe
                740                745                750

Asp Arg Ala Glu Pro His Lys Leu Ile Glu Ala Leu Gly His Cys Leu
            755                760                765

Glu Thr Tyr Arg Lys Tyr Lys Glu Ser Trp Arg Gly Leu Gln Val Arg
            770                775                780

Gly Met Ser Gln Asp Leu Ser Trp Asp His Ala Ala Glu Leu Tyr Glu
785                790                795                800

Glu Val Leu Val Lys Ala Lys Tyr Gln Trp
                805                810

<210> SEQ ID NO 14
<211> LENGTH: 2248
<212> TYPE: DNA
<213> ORGANISM: Zea mays

<400> SEQUENCE: 14
gcacctttgt agccccgcgc tcggcgcaat gcggtctcca aacctaggga tcctcttcag    60
ccggtcggcc ggtacggctc cgcgacggga acacggccag gaccggcgc cgcttcctgc   120 cagaacgccg cattggcgga cgttgagatc aagtccatcg tcgccgcgcc gccgacgagc   180
atagtgaagt tcccagcgcc gggctacagg atgatccttc cctctgggga catagcgccg   240
gagactgtcc tcccagcccc gaagccactg catgaatcgc ctgcggttga cggagattca   300
aatggaattg cacctcctac agttgagcca ttagtacagg aggccacttg ggatttcaag   360
aaatacatcg ttttgacga gcctgtcgaa gcgaaggatg attccagggt tggtgcagat   420
gatgctggtt cttttgaaca ttatggggac aatgattctg ggccttttgc cggggagaat   480
gttatgaacg tgatcgtggt ggctgctgaa tgttctccat ggtgcaaaac aggtggtctt   540
```

```
ggagatgttg tgggagcttt acccaaggct ttagcgagaa gaggacatcg tgttatggtt      600
gtggtaccaa ggtatgggga ctatgtggaa gcctttgata tgggaatccg gaaatactac      660
aaagctgcag acaggacct  agaagtgaac tatttccatg catttattga tggagtcgac      720
tttgtgttca ttgatgcccc tcttttccgg caccgtcaag atgacatata tggggggaag      780
taggcaggag atcatgaagc gcatgatttt gttttgcaag gttgctgttg aggttccttg      840
gcacgttcca tgtggtggtg tgtgctacgg agatggaaat ttggtgttca ttgccaatga      900
ttggcacact gcactcctgc ctgtttatct gaagggcata ttacagagac catgggttaa      960
tgcagtacac tcgctccgtc ctcgtcatac ataacatcgc ccaccagggc cgtggtcctg     1020
tagatgaatt cccgtacatg gacttgcctg aacactacct tcaacatttc gagctgtacg     1080
atcccgtggg tggcgagcac gccaacatct tgccgcgggg tctgaagatg gcagaccggg     1140
tggtgactgt cagccgcggc tacctgtggg agctgaagac agtggaaggc ggctggggcc     1200
tccacgacat catccgttct aacgactgga agatcaatgg catcgtgaac ggcatcgacc     1260
acgaggagtg gaaccccaag gtggacgtgc acctgcggtc ggacggctac accaactact     1320
ccctcgagac actcgacgct ggaaagcggc agtgcaaggc ggccctgcag cgggagctgg     1380
gcctggaagt gcgcgacgac gtgccgctgc tcggcttcat cggcgtctg  gatggacaga     1440 agggcgtgga catcatcggg gacgcgatgc cgtggatcgc ggggcaggac gtgcagctgg     1500
tgatgctggg caccgggcgc gccgacctgg aacgaatgct gcagcacttg gagcgggagc     1560
atcccaacaa ggtgcgcggg tgggtcgggt ctcggtgcc  tatggcgcat cgcatcacgg     1620
cgggcgccga cgtgctggtg atgccctccc gcttcgagcc ctgcgggctg aaccagctct     1680
acgcgatggc atacggcacc gtccctgtgg tgcacgccgt gggcgggctc agggacaccg     1740
tggcgccgtt cgacccgttc agcgacgccg ggctcgggtg gacttttgac cgcgccgagg     1800
ccaacaagct gatcgaggcg ctcaggcact gcctcgacac gtaccggaac tacgaggata     1860
gctggaagag tctccaggcg cgcggcatgt cgcaggacct cagctgggac cacgcggctg     1920
agctctacga ggacgtcctt gtcaaggcca agtaccagtg gtgaaccctc gccctccgc     1980 atcaatatct tcggtttgat cccattgtac atcgcgcgtt tgacggtctc ggtgaagaac     2040
ttcatatgca gtgacgcgcc gctgggggttg gtagcagtac tatgggattg cattgagctg     2100
tgtcactatg tgctttcgac aggacagtag tgtaggttgt atgcaagttt agttttttt       2160 cattactgat atttggaatg tcaacacaat aaatgaagct actatgtgtt tcgtaagtat     2220
aatgttactt atttaggtga taaaaaaa                                         2248
```

<210> SEQ ID NO 15
<211> LENGTH: 2645
<212> TYPE: DNA
<213> ORGANISM: Oryza sativa

<400> SEQUENCE: 15

```
gaatctcttt tctctcgtcg tcgtctcgtc ttcccacctc tcggattccc gagctccaca       60
cgacacgacc cacctcggcc actctccgcc gtcggtggcc agtggcctcc acccctccg      120 tcccccgggg accacaccgg cgtaacatca gccacacctc cggcagatct ttcccccgcc     180
gcttaattca cctcctcttc gccgcggcgc aggcggagca gggtgagcgg ggtttggtgg     240
cacttgtatg gtggcacggg gctgcggttg cattgggagc ggcggggttt ggttcgggac     300
ggagccgtcg tgtgctcggc gtcggccgcc ggtggtgaga atggcgtcgc gaaggcgaag     360
acgaagtcag cggggagctc gaaggcggtc gctgtgcagg gcagcacggc caaggctgat     420
```

```
catgttgagg attcagtttc atcacccaaa tacgtgaaac ctgccgttgc gaagcaaaat      480
ggagaggttg tgagcagagc taccaaatct gatgcaccag tgtctaaacc caaagttgac      540
ccgtcagttc ctgcttccaa ggctgaagct gatggtaatg cacaagctgt ggaatcgaag      600
gctgcactgg acaagaagga agacgtcggt gttgctgaac cgttggaagc taaggctgat      660
gctggtggag atgcaggtgc agtaagctct gcagatgata gtgagaacaa ggaatctggt      720
ccattggcag ggccaaatgt gatgaatgtc attgtggtgg cttctgaatg ttctcctttc      780
tgtaaaacag gtggtcttgg agatgttgtg ggtgctttgc ctaaggctct ggcaagaaga      840
ggacatcgtg ttatggttgt gataccaaga tacggagaat atgcagaagc caaggatcta      900
ggtgtccgca aacgttacag ggtagctgga caggattcag aagtgagtta ttttcatgct      960
tttatcgatg tgttgatttt tgtgtttcta gaggcccctc cctttcgaca ccggcacaat     1020
gatatttatg gaggagaaag atttgatgtt ttgaagcgta tgattttgtt ctgcaaagct     1080
gctgttgagg ttccttggtt tgctccatgt ggtggttcca tctacggtga tgcaattta      1140 gtcttcattg caaatgattg gcatactgca cttttacccg tatatttgaa ggcatattac     1200
cgagataatg gcttgatgca gtatactcgc tctgttcttg tgatacacaa cattgctcat     1260
cagggtcgtg gccctgtaga tgacttcgcc acgatggact tgcccgagca ctacatcgat     1320
catttcagac tgtacgaccc cgtcggcggt gagcacagca acgtgttcgc cgctggcctg     1380
aagatggctg accgcgcggt caccgtcagc catggctatc tgtgggagat caagacaatg     1440
gacggtggct ggggcctcca cgagataata aaccacaacg actggaagct gcagggcatc     1500
gtgaacggca tcgacatggc cgaatggaac cccgaggtgg acgagcacct gcagtccgac     1560
ggctacgcca actacacgtt cgagacgctg gacaccggca agaaacagtg caaggaggcg     1620
ctgcagcggc agctgggcct gcaggtccgc gacgacgtgc cgctgatcgg gttcatcggg     1680
cggctcgacc accagaaggg cgtggacatc atcggcgacg cgatgccgtg gatcgccggg     1740
caggacgtgc aggtggtgat gggggcacgg ggcggccgga cctggaggag atgctgcggc     1800
ggttcgagtc ggagcacaac gacaaggtgc gcgggtgggt ggggttctcg gtgcagctgg     1860
cgcaccggat cacggcgggc gccgacgtcc tcctgatgcc gtcgcggttc gagccgtgcg     1920
ggctgaacca gctgtacgcc atggcgtacg gcaccgtgcc cgtggtgcac gccgtgggcg     1980
ggctccgcga cacggtggcg ccgttcgacc cgttcgccga cacggggctc gggtggacgt     2040
tcgaccgcgc cgaggcgaac cggatgatcg acgcgctcgg gcactgcctc aacacgtacc     2100
ggaactacaa ggagagctgg aggggctcc aggcgcgcgg catggcgcag gacctcagct     2160
gggaccacgc cgccgagctc tacgaggacg tcctcgtcaa ggccaagtac cagtggtgag     2220
ctggtggtat ttttcgcgac gcctctggat ccgccgtgg atgggcgcgc ttttctcta      2280 gggcggctct cgtcggaga cgctcagacg catcgcgcgc gttcgcgccc acacgatgac     2340
tggcacgctg ctgctgagac ggcggcacgc gatgccatca tgccaccgga cggtaggagc     2400
aacggtggaa gtgaactgta ctactggtgc tacactgcta ctacatgaga tctgctctta     2460
ttggtcacgt actcacgttc acgctgaatt accgaatgtg ttgtgtcttg tgtgtgtgtg     2520
ttaaaggcat tgtcctggta aatggtggag acagatggc cgggtcgcgg gagttatatt      2580
tgtatatgtt gccagctttc tgagtttttc aagccagtgc ggctcttcag tgcaggttcc     2640
aagcg                                                                 2645
```

<210> SEQ ID NO 16

<211> LENGTH: 2394
<212> TYPE: DNA
<213> ORGANISM: Oryza sativa

<400> SEQUENCE: 16

```
ggaggaggag gagcggcggc ggcggcggat cctatgtcgg gggcaatcgc ttcctcgccg      60
gcggctactc tcttcctcgc tggctcctcc tcctcttcgc cgcggcgcag gcggagcagg     120
gtgagcgggg tttggtggca cttgtatggt ggcacggggc tgcggttgca ttgggagcgg     180
cggggtttgg ttcgggacgg agccgtcgtg tgctcggcgt cggccgccgg tggtgaggat     240
ggcgtcgcga aggcgaagac gaagtcagcg ggagctcga aggcggtcgc tgtgcagggc      300
agcacggcca aggctgatca tgttgaggat tcagtttcat cacccaaata cgtgaaacct     360
gccgttgcga agcaaaatgg agaggttgtg agcagagcta ccaaatctga tgcaccagtg     420
tctaaaccca aagttgaccc gtcagttcct gcttccaagg ctgaagctga tggtaatgca     480
caagctgtgg aatcgaaggc tgcactgac aagaaggaag acgtcggtgt tgctgaaccg      540
ttggaagcta aggctgatgc tggtggagat gcaggtgcag taagctctgc agatgatagt     600
gagaacaagg aatctggtcc attggcaggg ccaaatgtga tgaatgtcat tgtggtggct     660
tctgaatgtt ctcctttctg taaaacaggt ggtcttggag atgttgtggg tgctttgcct     720
aaggctctgg caagaagagg acatcgtgtt atggttgtga taccaagata cggagaatat     780
gcagaagcca aggatctagg tgtccgcaaa cgttacaggg tagctggaca ggattcagaa     840
gtgagttatt tcatgctttt tatcgatggt gttgattttg tgtttctaga ggcccctccc     900
tttcgacacc ggcacaatga tatttatgga ggagaaagat ttgatgtttt gaagcgtatg     960
attttgttct gcaaagctgc tgttgaggtt ccttggtttg ctccatgtgg tggttccatc    1020
tacggtgatg gcaatttagt cttcattgca aatgattggc atactgcact tttacccgta    1080
tgtttgaagg catattaccg agataatggc ttgatgcagt atactcgctc tgttcttgtg    1140
atacacaaca ttgctcatca gggtcgcggc cctgtagatg acttcgccac gatggacttg    1200
cccgagcact acatcgatca tttcagactg tacgaccccg tcggcggtga gcacagcaac    1260
gtgttcgccg ctggcctgaa gatggctgac cgcgcggtca ccgtcagcca tggctatctg    1320
tgggagatca agacaatgga cggtggctgg ggcctccacg agataataaa ccacaacgac    1380
tggaagctgc agggcatcgt gaatggcatc gacatggccg aatggaaccc cgaggtggac    1440
gagcacctgc agtccgacgg ctacgccaac tacacgttcg agacgctgga caccggcaag    1500
aaacagtgca aggaggcgct gcagcggcag ctgggcctgc aggtccgcga cgacgtgccg    1560
ctgatcgggt tcatcgggcg gctcgaccac cagaagggcg tggacatcat cggcgacgcg    1620
atgccgtgga tcgccgggca ggacgtgcag gtggtgatgc tgggcacggg gcggccggac    1680
ctggaggaga tgctgcggcg gttcgagtcg gagcacaacg acaaggtgcg cggtggggtg    1740
gggttctcgg tgcagctggc gcaccggatc acgcgggcg ccgacgtcct cctgatgccg    1800
tcgcggttcg agccgtgcgg gctgaaccag ctgtacgcca tggcgtacag caccgtgccc    1860
gtggtgcacg ccgtgggcgg gctccgcgac acggtggcgc cgttcgaccc gttcgccgac    1920
acggggctcg ggtggacgtt cgaccgcgcc gaggcgaacc ggatgatcga cgcgctcggg    1980
cactgcctca acacgtaccg gaactacaag gagagctgga gggggctcca ggcgcgcggc    2040
atggcgcagg acctcagctg ggaccacgcc gccgagctct acgaggacgt cctcgtcaag    2100
gccaagtacc agtggtgagc tggtggtatt tttcgcgacg cctctggatc ccgccgtgga    2160
tgggcgcgct tttctctag gcggctctg cgtcggagac gctcagacgc atcgcgcgcg    2220
```

-continued

```
ttcgcgccca cacgatgact ggcacgctgc tgctgagacg gcggcacgcg atgccatcat    2280
gccaccggac ggtaggagca acggtggaag tgaactgtac tactggtgct acactgctac    2340
tacatgagat ctgctcttat tggtcacgta ctcacgttca cgctgaatta ccga          2394
```

<210> SEQ ID NO 17
<211> LENGTH: 694
<212> TYPE: PRT
<213> ORGANISM: Oryza sativa

<400> SEQUENCE: 17

```
Met Ser Gly Ala Ile Ala Ser Ser Pro Ala Ala Thr Leu Phe Leu Ala
1               5                   10                  15

Gly Ser Ser Ser Ser Pro Arg Arg Arg Ser Arg Val Ser Gly
            20                  25                  30

Val Trp Trp His Leu Tyr Gly Thr Gly Leu Arg Leu His Trp Glu
        35                  40                  45

Arg Arg Gly Leu Val Arg Asp Gly Ala Val Val Cys Ser Ala Ser Ala
    50                  55                  60

Ala Gly Gly Glu Asp Gly Val Ala Lys Ala Lys Thr Lys Ser Ala Gly
65                  70                  75                  80

Ser Ser Lys Ala Val Ala Val Gln Gly Ser Thr Ala Lys Ala Asp His
                85                  90                  95

Val Glu Asp Ser Val Ser Ser Pro Lys Tyr Val Lys Pro Ala Val Ala
            100                 105                 110

Lys Gln Asn Gly Glu Val Val Ser Arg Ala Thr Lys Ser Asp Ala Pro
        115                 120                 125

Val Ser Lys Pro Lys Val Asp Pro Ser Val Pro Ala Ser Lys Ala Glu
    130                 135                 140

Ala Asp Gly Asn Ala Gln Ala Val Glu Ser Lys Ala Ala Leu Asp Lys
145                 150                 155                 160

Lys Glu Asp Val Gly Val Ala Glu Pro Leu Glu Ala Lys Ala Asp Ala
                165                 170                 175

Gly Gly Asp Ala Gly Ala Val Ser Ser Ala Asp Asp Ser Glu Asn Lys
            180                 185                 190

Glu Ser Gly Pro Leu Ala Gly Pro Asn Val Met Asn Val Ile Val Val
        195                 200                 205

Ala Ser Glu Cys Ser Pro Phe Cys Lys Thr Gly Gly Leu Gly Asp Val
    210                 215                 220

Val Gly Ala Leu Pro Lys Ala Leu Ala Arg Arg Gly His Arg Val Met
225                 230                 235                 240

Val Val Ile Pro Arg Tyr Gly Glu Tyr Ala Glu Ala Lys Asp Leu Gly
                245                 250                 255

Val Arg Lys Arg Tyr Arg Val Ala Gly Gln Asp Ser Glu Val Ser Tyr
            260                 265                 270

Phe His Ala Phe Ile Asp Gly Val Asp Phe Val Phe Leu Glu Ala Pro
        275                 280                 285

Pro Phe Arg His Arg His Asn Asp Ile Tyr Gly Gly Glu Arg Phe Asp
    290                 295                 300

Val Leu Lys Arg Met Ile Leu Phe Cys Lys Ala Val Glu Val Pro
305                 310                 315                 320

Trp Phe Ala Pro Cys Gly Gly Ser Ile Tyr Gly Asp Gly Asn Leu Val
                325                 330                 335

Phe Ile Ala Asn Asp Trp His Thr Ala Leu Leu Pro Val Cys Leu Lys
```

```
                340                 345                 350
Ala Tyr Tyr Arg Asp Asn Gly Leu Met Gln Tyr Thr Arg Ser Val Leu
            355                 360                 365

Val Ile His Asn Ile Ala His Gln Gly Arg Gly Pro Val Asp Asp Phe
        370                 375                 380

Ala Thr Met Asp Leu Pro Glu His Tyr Ile Asp His Phe Arg Leu Tyr
385                 390                 395                 400

Asp Pro Val Gly Gly Glu His Ser Asn Val Phe Ala Ala Gly Leu Lys
                405                 410                 415

Met Ala Asp Arg Ala Val Thr Val Ser His Gly Tyr Leu Trp Glu Ile
            420                 425                 430

Lys Thr Met Asp Gly Gly Trp Gly Leu His Glu Ile Ile Asn His Asn
        435                 440                 445

Asp Trp Lys Leu Gln Gly Ile Val Asn Gly Ile Asp Met Ala Glu Trp
    450                 455                 460

Asn Pro Glu Val Asp Glu His Leu Gln Ser Asp Gly Tyr Ala Asn Tyr
465                 470                 475                 480

Thr Phe Glu Thr Leu Asp Thr Gly Lys Lys Gln Cys Lys Glu Ala Leu
                485                 490                 495

Gln Arg Gln Leu Gly Leu Gln Val Arg Asp Asp Val Pro Leu Ile Gly
            500                 505                 510

Phe Ile Gly Arg Leu Asp His Gln Lys Gly Val Asp Ile Ile Gly Asp
        515                 520                 525

Ala Met Pro Trp Ile Ala Gly Gln Asp Val Gln Val Met Leu Gly
        530                 535                 540

Thr Gly Arg Pro Asp Leu Glu Glu Met Leu Arg Arg Phe Glu Ser Glu
545                 550                 555                 560

His Asn Asp Lys Val Arg Gly Trp Val Gly Phe Ser Val Gln Leu Ala
                565                 570                 575

His Arg Ile Thr Ala Gly Ala Asp Val Leu Leu Met Pro Ser Arg Phe
            580                 585                 590

Glu Pro Cys Gly Leu Asn Gln Leu Tyr Ala Met Ala Tyr Ser Thr Val
        595                 600                 605

Pro Val Val His Ala Val Gly Gly Leu Arg Asp Thr Val Ala Pro Phe
    610                 615                 620

Asp Pro Phe Ala Asp Thr Gly Leu Gly Trp Thr Phe Asp Arg Ala Glu
625                 630                 635                 640

Ala Asn Arg Met Ile Asp Ala Leu Gly His Cys Leu Asn Thr Tyr Arg
                645                 650                 655

Asn Tyr Lys Glu Ser Trp Arg Gly Leu Gln Ala Arg Gly Met Ala Gln
            660                 665                 670

Asp Leu Ser Trp Asp His Ala Ala Glu Leu Tyr Glu Asp Val Leu Val
        675                 680                 685

Lys Ala Lys Tyr Gln Trp
    690

<210> SEQ ID NO 18
<211> LENGTH: 2025
<212> TYPE: DNA
<213> ORGANISM: Triticum aestivum

<400> SEQUENCE: 18
atgtcggggg caatagcttc ctcgtccgcg gcgttcctct tgctcgtggc ctcctcctcc      60
tgctcctcct cgtcgccgcg gcgctggcgg agcagctcac cgcgctcttt cgctgccgcc     120
```

| | |
|---|---|
| ggtacgcggc tgcattggga acggcgagga ttctctcggg acggaccggt gccgtgccgg | 180 |
| agcccctgcg cagcagctgg tggtgaggat ggcgcggcgg caggggagag ctcgaaggag | 240 |
| ggggtcgctg ggctgcgcgg caagctcaag gctgctgaaa atgaggatcc ggtttcacaa | 300 |
| aaatcagttg catctgcacc caggctagac agtagcgttg cagagcaaaa tggggcagct | 360 |
| gcgaccagat ccaaagccga tccgtcagct cctgtctcgg cggcagcatc aggttattgg | 420 |
| aaagacgtcg ttgtcgctga acaggttgga actaaggttg acaccggtgg agatgcagca | 480 |
| gaagtgtcga gatctcccgt tgacagtgag aacaaggggt ctgctccttt ggctggcccg | 540 |
| aatgtgatga atgtcatcgt tgtggcttct gagtgtgctc cttctgtaa acaggcggg | 600 |
| cttggagatg tcgtgggtgc tttgcccaag gctctggcca agagggca tcgcgttatg | 660 |
| gttgtgatac caaagtatgg cgattacgca gaagctcgtg atcttggtgt cgcaaacgt | 720 |
| tacaaggtag ctggccagga ttcagaagtg agttactttc actcttatat cgatggagtt | 780 |
| gattttgtat tcttagaggc cccgcccttc cgccaccggc acaatgatat ttatggagga | 840 |
| gaaagaccgg atgtgctgaa gcgcatgatt ttgttctgca aggctgctgt cgaggttcct | 900 |
| aggtacgctc tatgtggtgg tactatctac ggagatggca atttggtctt cattgcaaac | 960 |
| gattggcata ctgcacttct acctgtttat ctaaaggcat attaccgaga caatggcctg | 1020 |
| atgcagtata ctcgttctgt tctcgtgatc cataacattg ctcatcaggg acgtggcct | 1080 |
| gtagatgact tcaacatcat ggacttgcct gaccactaca tgggtcactt caaactgcat | 1140 |
| gacccccttg gtggcgagca caacaacgtg ttcgccgctg gcctgaagat ggcagaccgg | 1200 |
| gtggtcaccg tcagccatgg ctacatgtgg gagctgaaga cggtggaagg cggctggggc | 1260 |
| ctccacgaca taataaacca gaacgactgg aaactggacg gcatcgtgaa cggcatcgac | 1320 |
| acggccgagt ggaaccccgc ggtcgacgtg cacctgcact ccgacgacta caccaactac | 1380 |
| acccgagaca cgctggacat cggcaagcgg cagtgcaagg cggccctgca gcgcgagctg | 1440 |
| ggcctgcagg tccgcgacga cgtgccgctc atcgggttca cgggcggct ggaccaccag | 1500 |
| aagggcgtgg acatcatcgc ggcggcgatg ccgtggatcg cgcagcagga cgtgcagctg | 1560 |
| gtgatgctgg gcacggggcg gccggacctg gaggacatgc tgcggcggtt cgagggggag | 1620 |
| caccgggaca aggtgcgcgg gtgggtgggg ttctcggtgc ggatggcgca ccggatcacg | 1680 |
| gcgggcgcgg acgtcctgct gatgccgtcg ctgttcgagc cgtgcgggct gaaccagctg | 1740 |
| tacgcggtgg cgtacgggac cgtgcccgtg gtgcacgccg tcggcgggct ccgggacacg | 1800 |
| gtggcgccgt cgacccgtt cggcggcacc gggctggggt ggacgttcga ccgcgcggac | 1860 |
| gccggcagga tgatcgacgc gctcgggcac tgcctcaaca cgtactggaa ctacaaggag | 1920 |
| agctggaggg gcctccaggt ccgcggcatg tcgcaggacc tcagctggga ccacgccgcc | 1980 |
| gagctctacg agaacgtcct cgtcaaggcc aagtaccagt ggtga | 2025 |

<210> SEQ ID NO 19
<211> LENGTH: 674
<212> TYPE: PRT
<213> ORGANISM: Triticum aestivum

<400> SEQUENCE: 19

Met Ser Gly Ala Ile Ala Ser Ser Ser Ala Ala Phe Leu Leu Leu Val
1               5                   10                  15

Ala Ser Ser Ser Cys Ser Ser Ser Ser Pro Arg Arg Trp Arg Ser Ser
                20                  25                  30

-continued

```
Ser Pro Arg Ser Phe Ala Ala Gly Thr Arg Leu His Trp Glu Arg
        35                  40                  45

Arg Gly Phe Ser Arg Asp Gly Pro Val Pro Cys Arg Ser Pro Cys Ala
 50                  55                  60

Ala Ala Gly Gly Glu Asp Gly Ala Ala Ala Gly Glu Ser Ser Lys Glu
 65                  70                  75                  80

Gly Val Ala Gly Leu Arg Gly Lys Leu Lys Ala Ala Glu Asn Glu Asp
                 85                  90                  95

Pro Val Ser Gln Lys Ser Val Ala Ser Ala Pro Arg Leu Asp Ser Ser
            100                 105                 110

Val Ala Glu Gln Asn Gly Ala Ala Ala Thr Arg Ser Lys Ala Asp Pro
        115                 120                 125

Ser Ala Pro Val Ser Ala Ala Ala Ser Gly Tyr Trp Lys Asp Val Val
    130                 135                 140

Val Ala Glu Gln Val Gly Thr Lys Val Asp Thr Gly Gly Asp Ala Ala
145                 150                 155                 160

Glu Val Ser Arg Ser Pro Val Asp Ser Glu Asn Lys Gly Ser Ala Pro
                165                 170                 175

Leu Ala Gly Pro Asn Val Met Asn Val Ile Val Ala Ser Glu Cys
            180                 185                 190

Ala Pro Phe Cys Lys Thr Gly Gly Leu Gly Asp Val Val Gly Ala Leu
        195                 200                 205

Pro Lys Ala Leu Ala Arg Arg Gly His Arg Val Met Val Val Ile Pro
    210                 215                 220

Lys Tyr Gly Asp Tyr Ala Glu Ala Arg Asp Leu Gly Val Arg Lys Arg
225                 230                 235                 240

Tyr Lys Val Ala Gly Gln Asp Ser Glu Val Ser Tyr Phe His Ser Tyr
                245                 250                 255

Ile Asp Gly Val Asp Phe Val Phe Leu Glu Ala Pro Pro Phe Arg His
            260                 265                 270

Arg His Asn Asp Ile Tyr Gly Gly Glu Arg Pro Asp Val Leu Lys Arg
        275                 280                 285

Met Ile Leu Phe Cys Lys Ala Ala Val Glu Val Pro Arg Tyr Ala Leu
    290                 295                 300

Cys Gly Gly Thr Ile Tyr Gly Asp Gly Asn Leu Val Phe Ile Ala Asn
305                 310                 315                 320

Asp Trp His Thr Ala Leu Leu Pro Val Tyr Leu Lys Ala Tyr Tyr Arg
                325                 330                 335

Asp Asn Gly Leu Met Gln Tyr Thr Arg Ser Val Leu Val Ile His Asn
            340                 345                 350

Ile Ala His Gln Gly Arg Gly Pro Val Asp Asp Phe Asn Ile Met Asp
        355                 360                 365

Leu Pro Asp His Tyr Met Gly His Phe Lys Leu His Asp Pro Leu Gly
    370                 375                 380

Gly Glu His Asn Asn Val Phe Ala Ala Gly Leu Lys Met Ala Asp Arg
385                 390                 395                 400

Val Val Thr Val Ser His Gly Tyr Met Trp Glu Leu Lys Thr Val Glu
                405                 410                 415

Gly Gly Trp Gly Leu His Asp Ile Ile Asn Gln Asn Asp Trp Lys Leu
            420                 425                 430

Asp Gly Ile Val Asn Gly Ile Asp Thr Ala Glu Trp Asn Pro Ala Val
        435                 440                 445

Asp Val His Leu His Ser Asp Asp Tyr Thr Asn Tyr Thr Arg Asp Thr
```

```
                450               455               460
Leu Asp Ile Gly Lys Arg Gln Cys Lys Ala Ala Leu Gln Arg Glu Leu
465                 470                 475                 480

Gly Leu Gln Val Arg Asp Val Pro Leu Ile Gly Phe Ile Gly Arg
            485                 490                 495

Leu Asp His Gln Lys Gly Val Asp Ile Ala Ala Ala Met Pro Trp
                500                 505                 510

Ile Ala Gln Gln Asp Val Gln Leu Val Met Leu Gly Thr Gly Arg Pro
            515                 520                 525

Asp Leu Glu Asp Met Leu Arg Arg Phe Glu Gly Glu His Arg Asp Lys
            530                 535                 540

Val Arg Gly Trp Val Gly Phe Ser Val Arg Met Ala His Arg Ile Thr
545                 550                 555                 560

Ala Gly Ala Asp Val Leu Leu Met Pro Ser Leu Phe Glu Pro Cys Gly
                565                 570                 575

Leu Asn Gln Leu Tyr Ala Val Ala Tyr Gly Thr Val Pro Val Val His
            580                 585                 590

Ala Val Gly Gly Leu Arg Asp Thr Val Ala Pro Phe Asp Pro Phe Gly
            595                 600                 605

Gly Thr Gly Leu Gly Trp Thr Phe Asp Arg Ala Asp Ala Gly Arg Met
610                 615                 620

Ile Asp Ala Leu Gly His Cys Leu Asn Thr Tyr Trp Asn Tyr Lys Glu
625                 630                 635                 640

Ser Trp Arg Gly Leu Gln Val Arg Gly Met Ser Gln Asp Leu Ser Trp
            645                 650                 655

Asp His Ala Ala Glu Leu Tyr Glu Asn Val Leu Val Lys Ala Lys Tyr
            660                 665                 670

Gln Trp

<210> SEQ ID NO 20
<211> LENGTH: 2302
<212> TYPE: DNA
<213> ORGANISM: Sorghum bicolor
<220> FEATURE:
<221> NAME/KEY: misc_feature
<222> LOCATION: (2247)..(2247)
<223> OTHER INFORMATION: n is a, c, g, or t

<400> SEQUENCE: 20
cggaagcagc agcagcagta gcgtgaggca tccccatgtc ggcggcaatc tcctcctcgt      60
cctcggcttt tctcctcctc atcgcgtcct cctcgccgcg gcgcaggcgg ggcagggtgg     120
gcgctgctct gcgctcctac ggctacagcg gcgcggagct gcggttgcat tgggcgcggc     180
gggccccgtc acgggatgcg gcggcggtag tagtgcgcgc cgcagcggcg ccggccgggg     240
gtgaggaggg cgaggaggcc gcggcggcag ggatgagctc ctcgtccaag ggcgtcgccg     300
tgcagggcag caaggccaag gctgtagatt ctacttcacc tcccaaacct gtgacttctg     360
cgacgaagca aagtccgagc gctgcaaatc aaaacggaac ggttgggagc agcagtgcaa     420
gcaaatctgc cacgccggtg tccgaactca agctgaaaac atcagctcct gtcaccaaga     480
ctgaaaccga tgccagtgcg aaggttgaag agccgaagcc cgcggtggat gatgctaaac     540
cggtggaaag cataggcgtt gctgagccgg tgatgctaa ggtggacgtc gctgcagcta     600
ctgatgtgga ggcgagtgct gctgatgaca gtgaggacaa gaaacctggc cctttggctg     660
ggcctaatgt gatgaatgtc gtcgtggtgg cttctgaatg tgctcctttc tgcaagacag     720
```

-continued

```
gtggccttgg agatgttgtg ggtgctttgc cgaaggcttt ggcgaggaga gggcaccgcg    780
ttatggtcgt gataccaaga tatggagaat atgcagaagc ccgagattta ggtgtgcgga    840
aacgttacag ggtagctgga caggattcag aagttactta ctttcactct tacattgatg    900
gagttgattt tgtattcata gaagccccac ccttccggca ccggcacaat aatatttatg    960
gaggagaaag attggatatt ttgaagcgca tgattttgtt ctgcaaggcc gctgttgagg   1020
ttccatggta tgctccatgt ggcggtaccg tctatggtga tggcaactta gttttcattg   1080
ctaatgattg gcatactgca cttctgccgg tctatctaaa ggcctattac cgggacagtg   1140
gtttgatgca gtatgctcgc tctgtgcttg tgatacacaa cattgctcat cagggtcgtg   1200
gccctgtaga cgacttcgtc aattttgact tgcctgaaca ttacatcgat cacttcaaac   1260
tgtatgacaa tatcggtggc gatcacagca acgttttcgc cgcgggcctg aaggcggcag   1320
accgggtggt gaccgtcagc aatggctacc tgtgggagct gaagacttcg gaaggtgggt   1380
ggggcctcca cggcatcata aaccagaacg actggaagct gcagggcatc gtgaacggca   1440
tcgacatgag cgagtggaac cccgctgtgg acgtgcacct ccactccgac ggctacacca   1500
actacacgtt cgagacgctg gacactggca gcggcagtg caaggccgcc ctgcagcggc   1560
agctcggcct gcaggtccgc gacgacgtgc cactgatcgg gttcatcggt cgcctggatg   1620
gacagaaggg cgtggacctc atcggcgacg cgatccactg gatcgcgggg caggacgtgc   1680
agctggtgat gctgggcacc gggcgccccg acctggagga catgctgcgg cggtgcgagg   1740
cggagcacaa cgacaaggtg cgcgcgtggg tcggtttctc ggttcccctg cgcaccgca   1800
tcacggcggg cgccgacgtc ctgctgatgc cgtcgcggtt cgagccgtgc gggctgaacc   1860
agctctacgc gatggcgtac gggaccgtgc ccgtggtgca cgccgtgggc gggctccggg   1920
acacggtggc gccgttcgac ccgttcaacg acaccgggct cggtggacg ttcgaccgcg   1980
ccgaggcgaa tcggatgatc gacgcgctcc atcactgcct caacacgtac cggaacttca   2040
aggagagctg cgcgcggcctg caggagcgcg gcatggcgca ggacctgagc tgggaccacg   2100
ccgccgtgct gtatgaggac gtgctcgtca aggccaagta ccagtggtga ctggtgagtg   2160
ggtttaactg gcgacgccga cgccctcctg tcgcgggacc tggacgcgtt gggcatgtta   2220
tttcggcggc tcttctcccc tcggctntga tgcgtgcggc gcaattgcgc cgcccgggcg   2280
gagggtgatg gtggttggcc ta                                             2302
```

<210> SEQ ID NO 21
<211> LENGTH: 704
<212> TYPE: PRT
<213> ORGANISM: Sorghum bicolor

<400> SEQUENCE: 21

```
Met Ser Ala Ala Ile Ser Ser Ser Ser Ala Phe Leu Leu Leu Ile
1               5                   10                  15

Ala Ser Ser Pro Arg Arg Arg Arg Gly Arg Val Gly Ala Ala Leu
            20                  25                  30

Arg Ser Tyr Gly Tyr Ser Gly Ala Glu Leu Arg Leu His Trp Ala Arg
        35                  40                  45

Arg Ala Pro Ser Arg Asp Ala Ala Val Val Arg Ala Ala Ala
    50                  55                  60

Ala Pro Ala Gly Gly Glu Glu Gly Glu Glu Ala Ala Ala Gly Met
65                  70                  75                  80

Ser Ser Ser Ser Lys Gly Val Ala Val Gln Gly Ser Lys Ala Lys Ala
                85                  90                  95
```

```
Val Asp Ser Thr Ser Pro Pro Lys Pro Val Thr Ser Ala Thr Lys Gln
            100                 105                 110

Ser Pro Ser Ala Ala Asn Gln Asn Gly Thr Val Gly Ser Ser Ser Ala
            115                 120                 125

Ser Lys Ser Ala Thr Pro Val Ser Glu Leu Lys Ala Glu Thr Ser Ala
130                 135                 140

Pro Val Thr Lys Thr Glu Thr Asp Ala Ser Ala Lys Val Glu Glu Pro
145                 150                 155                 160

Lys Pro Ala Val Asp Asp Ala Lys Pro Val Glu Ser Ile Gly Val Ala
                165                 170                 175

Glu Pro Val Asp Ala Lys Val Asp Val Ala Ala Thr Asp Val Glu
                180                 185                 190

Ala Ser Ala Ala Asp Asp Ser Glu Asp Lys Lys Pro Gly Pro Leu Ala
            195                 200                 205

Gly Pro Asn Val Met Asn Val Val Val Ala Ser Glu Cys Ala Pro
            210                 215                 220

Phe Cys Lys Thr Gly Gly Leu Gly Asp Val Val Gly Ala Leu Pro Lys
225                 230                 235                 240

Ala Leu Ala Arg Arg Gly His Arg Val Met Val Val Ile Pro Arg Tyr
                245                 250                 255

Gly Glu Tyr Ala Glu Ala Arg Asp Leu Gly Val Arg Lys Arg Tyr Arg
            260                 265                 270

Val Ala Gly Gln Asp Ser Glu Val Thr Tyr Phe His Ser Tyr Ile Asp
                275                 280                 285

Gly Val Asp Phe Val Phe Ile Glu Ala Pro Pro Phe Arg His Arg His
            290                 295                 300

Asn Asn Ile Tyr Gly Gly Glu Arg Leu Asp Ile Leu Lys Arg Met Ile
305                 310                 315                 320

Leu Phe Cys Lys Ala Ala Val Glu Val Pro Trp Tyr Ala Pro Cys Gly
                325                 330                 335

Gly Thr Val Tyr Gly Asp Gly Asn Leu Val Phe Ile Ala Asn Asp Trp
            340                 345                 350

His Thr Ala Leu Leu Pro Val Tyr Leu Lys Ala Tyr Tyr Arg Asp Ser
            355                 360                 365

Gly Leu Met Gln Tyr Ala Arg Ser Val Leu Val Ile His Asn Ile Ala
370                 375                 380

His Gln Gly Arg Gly Pro Val Asp Asp Phe Val Asn Phe Asp Leu Pro
385                 390                 395                 400

Glu His Tyr Ile Asp His Phe Lys Leu Tyr Asp Asn Ile Gly Gly Asp
                405                 410                 415

His Ser Asn Val Phe Ala Ala Gly Leu Lys Ala Ala Asp Arg Val Val
            420                 425                 430

Thr Val Ser Asn Gly Tyr Leu Trp Glu Leu Lys Thr Ser Glu Gly Gly
            435                 440                 445

Trp Gly Leu His Gly Ile Ile Asn Gln Asn Asp Trp Lys Leu Gln Gly
            450                 455                 460

Ile Val Asn Gly Ile Asp Met Ser Glu Trp Asn Pro Ala Val Asp Val
465                 470                 475                 480

His Leu His Ser Asp Gly Tyr Thr Asn Tyr Thr Phe Glu Thr Leu Asp
                485                 490                 495

Thr Gly Lys Arg Gln Cys Lys Ala Ala Leu Gln Arg Gln Leu Gly Leu
            500                 505                 510
```

```
Gln Val Arg Asp Asp Val Pro Leu Ile Gly Phe Ile Gly Arg Leu Asp
    515                 520                 525

Gly Gln Lys Gly Val Asp Leu Ile Gly Asp Ala Ile His Trp Ile Ala
530                 535                 540

Gly Gln Asp Val Gln Leu Val Met Leu Gly Thr Gly Arg Pro Asp Leu
545                 550                 555                 560

Glu Asp Met Leu Arg Arg Cys Glu Ala Glu His Asn Asp Lys Val Arg
                565                 570                 575

Ala Trp Val Gly Phe Ser Val Pro Leu Ala His Arg Ile Thr Ala Gly
                580                 585                 590

Ala Asp Val Leu Leu Met Pro Ser Arg Phe Glu Pro Cys Gly Leu Asn
                595                 600                 605

Gln Leu Tyr Ala Met Ala Tyr Gly Thr Val Pro Val Val His Ala Val
    610                 615                 620

Gly Gly Leu Arg Asp Thr Val Ala Pro Phe Asp Pro Phe Asn Asp Thr
625                 630                 635                 640

Gly Leu Gly Trp Thr Phe Asp Arg Ala Glu Ala Asn Arg Met Ile Asp
                645                 650                 655

Ala Leu His His Cys Leu Asn Thr Tyr Arg Asn Phe Lys Glu Ser Trp
                660                 665                 670

Arg Gly Leu Gln Glu Arg Gly Met Ala Gln Asp Leu Ser Trp Asp His
    675                 680                 685

Ala Ala Val Leu Tyr Glu Asp Val Leu Val Lys Ala Lys Tyr Gln Trp
    690                 695                 700

<210> SEQ ID NO 22
<211> LENGTH: 2569
<212> TYPE: DNA
<213> ORGANISM: Zea mays

<400> SEQUENCE: 22
acgctctagg ctctcgtttc ctcgtactgg tacaagcggg acgggagcag cagcagtagc      60
gtgatccatc cccatggcgg gggcaacctc ttcctcgtcc gtgtctttga tcctcatcct     120
cgtcgcgtcc tcctcgccgc ggcgcagccg gggcagggtg gcattgctc tgcgctcgta     180
cggctacagc ggcgccgagc tgcggttgca ttgggcgcgt cggggctcgt ctcgggatgg     240
accggcggta gtgcgcgccg cagcggttcc ggccgggggt gagggcgagg acgccgcggc     300
ggtagggaag agctcctcgt ccaaggcggt cgccgtgcag ggcagcgagt ccaaggctgt     360
atattctact tcacctccca aaactgcgac gtctgcgccg aagcaaaacc agagcgctgc     420
aaagcaaaac ggaacagttg ggagcagcag tgcgagcaaa tccccggcgc ctgcggtatc     480
tgaatccaaa gctgaaccat ctgctcctgt caccaagaca gaaaccgatg ccagtgcgaa     540
ggttgaagag ctgaagccct cagtggatga tgctaaaccc gtagaaagca taggcatccc     600
tgagccggtg gatgctaagg tggacgccgc tgcagctact gatgccgcgg cgagtgctgc     660
tgatgacact gaagacaagg aacatggccc tttggctggg cctaatgtga tgaatgtcgt     720
cgtggtggct tctgaatgcg ctcctttctg caagacaggt ggccttggag atgttgtggg     780
tgctttgccc aaggctttgg cgaggagagg acaccgtgtt atggtcgtga taccaagata     840
tggagagtat gcagaagccc gggatttagg tgtaaggaga cgttacaggg tggctggaca     900
ggattcagaa gttacttatt ttcactctta cattgatggc gttgattttg tattcataga     960
agcccctccc ttccggcacc ggcacaatga tatttatgga ggagaaagat cggatgtttt    1020
gaagcgcata attttgttct gcaaggccgc tgttgaggtt ccatggtacg ctccatgtgg    1080
```

```
tggtaccgtc tatggtgatg gcaatttagt tttcattgct aatgattggc atacggcact   1140
tcttccggtc tacctaaaag cctactaccg ggacaatggt ttgatgcagt atgctcgctc   1200
agtgcttgtg atacacaaca ttgctcatca gggtcgtggc cctgtagacg acttcgtcaa   1260
ctttgacttg cctgaacatt acatcgatca cttcaaactg tacgacaata tcggtggcga   1320
gcactgcaac gttttgccg cagggctgaa gatggcagac caggtggtga ccgtcagtaa   1380
tggataccta tgggagctga ggacatcgga aggtgggtgg ggcctccacg acatcataaa   1440
ccagaacgac tggaagctgc agggcatcgt gaacggcatc gacatgagcg agtggaaccc   1500
cgctgtggac gtgcacctcc actccgacga atacaccaac tacacgttcg agacgctgga   1560
cacgggcaag cggcagtgca aggctgccct gcagcggcag ctcggcctgc aggtccgcga   1620
cgacgtgcca ctaatcgggt tcatcgggcg gctggaccac cagaagggcg tggacatcat   1680
cgccgacgcg atccactgga tcgcgggaca ggacgtgcag cttgtgatgc tgggcacggg   1740
gcgccccgac ctggaggaca tgctgcggcg gtgcgaggcg gagcacagcg acaaggtgcg   1800
cgcgtgggtg gggttctcgg tgcccttggc gcaccgcatc acggcgggcg cggacgtcct   1860
gctgatgccg tcgcggttcg agccgtgcgg gctgaaccag ctctacgcga tggcgtacgg   1920
gaccgtgccc gtggtgcacg ccgtgggcgg gctccgggac acggtggcgc cgttcgaccc   1980
gttcaacgac accgggctgg ggtggacgtt cgaccgcgcg gaggcgaatc ggatgatcga   2040
cgcgctctcg cactgcctca cacgttccg gaactacaag gagagctggc gcggcctgga   2100
ggcgcgcggc atggcgcagg acctcagctg ggaccacgcc gccgtgctgt atgaggacgt   2160
gctcgtcaag gccaagtacc agtggtaagt gagttacgcc gacgcccttc atgtcgcggg   2220
acagtcctgg acgccctggg cactgcgtgc tcttctcacg cggctttgct gcgtgcggcg   2280
catttgctca attggcgcgg ggcgatggtg gttggcctac gtcggcttcg gctaggtgcc   2340
ttcggatttt cagcttctta ccaccaaaac accaaaagct gctgcggact attaaacgct   2400
cagtttttca gttagcttct ataaaaatcg atcgtaaaaa tcatctataa tcaacataaa   2460 cataatgg acgagtact tttaataata gaaatctatc gctttgtaga tcttacccta   2520
tggacacctt catcttgaaa attgtttggt tgaaataaca gtgagttgt              2569
```

<210> SEQ ID NO 23
<211> LENGTH: 704
<212> TYPE: PRT
<213> ORGANISM: Zea mays

<400> SEQUENCE: 23

```
Met Ala Gly Ala Thr Ser Ser Ser Val Ser Leu Ile Leu Ile Leu
1               5                   10                  15

Val Ala Ser Ser Ser Pro Arg Arg Ser Arg Gly Arg Val Gly Ile Ala
                20                  25                  30

Leu Arg Ser Tyr Gly Tyr Ser Gly Ala Glu Leu Arg Leu His Trp Ala
            35                  40                  45

Arg Arg Gly Ser Ser Arg Asp Gly Pro Ala Val Val Arg Ala Ala Ala
        50                  55                  60

Val Pro Ala Gly Gly Glu Gly Glu Asp Ala Ala Ala Val Gly Lys Ser
65                  70                  75                  80

Ser Ser Ser Lys Ala Val Ala Val Gln Gly Ser Glu Ser Lys Ala Val
                85                  90                  95

Tyr Ser Thr Ser Pro Pro Lys Thr Ala Thr Ser Ala Pro Lys Gln Asn
            100                 105                 110
```

Gln Ser Ala Ala Lys Gln Asn Gly Thr Val Gly Ser Ser Ala Ser
            115                 120                 125

Lys Ser Pro Ala Pro Ala Val Ser Glu Ser Lys Ala Glu Pro Ser Ala
    130                 135                 140

Pro Val Thr Lys Thr Glu Thr Asp Ala Ser Ala Lys Val Glu Glu Leu
145                 150                 155                 160

Lys Pro Ser Val Asp Asp Ala Lys Pro Val Glu Ser Ile Gly Ile Pro
                165                 170                 175

Glu Pro Val Asp Ala Lys Val Asp Ala Ala Ala Thr Asp Ala Ala
            180                 185                 190

Ala Ser Ala Ala Asp Asp Thr Glu Asp Lys Glu His Gly Pro Leu Ala
        195                 200                 205

Gly Pro Asn Val Met Asn Val Val Val Ala Ser Glu Cys Ala Pro
            210                 215                 220

Phe Cys Lys Thr Gly Gly Leu Gly Asp Val Val Gly Ala Leu Pro Lys
225                 230                 235                 240

Ala Leu Ala Arg Arg Gly His Arg Val Met Val Ile Pro Arg Tyr
                245                 250                 255

Gly Glu Tyr Ala Glu Ala Arg Asp Leu Gly Val Arg Arg Tyr Arg
            260                 265                 270

Val Ala Gly Gln Asp Ser Glu Val Thr Tyr Phe His Ser Tyr Ile Asp
        275                 280                 285

Gly Val Asp Phe Val Phe Ile Glu Ala Pro Pro Phe Arg His Arg His
        290                 295                 300

Asn Asp Ile Tyr Gly Gly Glu Arg Ser Asp Val Leu Lys Arg Ile Ile
305                 310                 315                 320

Leu Phe Cys Lys Ala Ala Val Glu Val Pro Trp Tyr Ala Pro Cys Gly
                325                 330                 335

Gly Thr Val Tyr Gly Asp Gly Asn Leu Val Phe Ile Ala Asn Asp Trp
            340                 345                 350

His Thr Ala Leu Leu Pro Val Tyr Leu Lys Ala Tyr Tyr Arg Asp Asn
        355                 360                 365

Gly Leu Met Gln Tyr Ala Arg Ser Val Leu Val Ile His Asn Ile Ala
    370                 375                 380

His Gln Gly Arg Gly Pro Val Asp Asp Phe Val Asn Phe Asp Leu Pro
385                 390                 395                 400

Glu His Tyr Ile Asp His Phe Lys Leu Tyr Asp Asn Ile Gly Gly Glu
                405                 410                 415

His Cys Asn Val Phe Ala Ala Gly Leu Lys Met Ala Asp Gln Val Val
            420                 425                 430

Thr Val Ser Asn Gly Tyr Leu Trp Glu Leu Arg Thr Ser Glu Gly Gly
        435                 440                 445

Trp Gly Leu His Asp Ile Ile Asn Gln Asn Asp Trp Lys Leu Gln Gly
    450                 455                 460

Ile Val Asn Gly Ile Asp Met Ser Glu Trp Asn Pro Ala Val Asp Val
465                 470                 475                 480

His Leu His Ser Asp Glu Tyr Thr Asn Tyr Thr Phe Glu Thr Leu Asp
                485                 490                 495

Thr Gly Lys Arg Gln Cys Lys Ala Ala Leu Gln Arg Gln Leu Gly Leu
            500                 505                 510

Gln Val Arg Asp Asp Val Pro Leu Ile Gly Phe Ile Gly Arg Leu Asp
        515                 520                 525

```
His Gln Lys Gly Val Asp Ile Ile Ala Asp Ala Ile His Trp Ile Ala
    530             535             540
Gly Gln Asp Val Gln Leu Val Met Leu Gly Thr Gly Arg Pro Asp Leu
545             550             555             560
Glu Asp Met Leu Arg Arg Cys Glu Ala Glu His Ser Asp Lys Val Arg
            565             570             575
Ala Trp Val Gly Phe Ser Val Pro Leu Ala His Arg Ile Thr Ala Gly
        580             585             590
Ala Asp Val Leu Leu Met Pro Ser Arg Phe Glu Pro Cys Gly Leu Asn
    595             600             605
Gln Leu Tyr Ala Met Ala Tyr Gly Thr Val Pro Val Val His Ala Val
610             615             620
Gly Gly Leu Arg Asp Thr Val Ala Pro Phe Asp Pro Phe Asn Asp Thr
625             630             635             640
Gly Leu Gly Trp Thr Phe Asp Arg Ala Glu Ala Asn Arg Met Ile Asp
            645             650             655
Ala Leu Ser His Cys Leu Asn Thr Phe Arg Asn Tyr Lys Glu Ser Trp
            660             665             670
Arg Gly Leu Glu Ala Arg Gly Met Ala Gln Asp Leu Ser Trp Asp His
        675             680             685
Ala Ala Val Leu Tyr Glu Asp Val Leu Val Lys Ala Lys Tyr Gln Trp
        690             695             700
```